United States Patent
Capano et al.

(10) Patent No.: US 12,097,211 B2
(45) Date of Patent: Sep. 24, 2024

(54) METHODS OF TREATING ESTROGEN SENSITIVE DISEASES WITH CANNABIS EXTRACT

(71) Applicants: Ecofibre USA Inc., Georgetown, KY (US); The University of Newcastle, Callaghan (AU)

(72) Inventors: Alexandra M. Capano, Philadelphia, PA (US); Pradeep Singh Tanwar, Fletcher (AU)

(73) Assignees: Ecofibre USA Inc., Georgetown, KY (US); The University of Newcastle, Callaghan (AU)

( * ) Notice: Subject to any disclaimer, the term of this patent is extended or adjusted under 35 U.S.C. 154(b) by 0 days.

(21) Appl. No.: 18/493,968

(22) Filed: Oct. 25, 2023

(65) Prior Publication Data
US 2024/0139218 A1 May 2, 2024

Related U.S. Application Data

(60) Provisional application No. 63/381,017, filed on Oct. 26, 2022.

(51) Int. Cl.
| | | |
|---|---|---|
| *A61K 31/565* | (2006.01) | |
| *A61K 31/00* | (2006.01) | |
| *A61K 31/282* | (2006.01) | |
| *A61K 31/337* | (2006.01) | |
| *A61K 36/185* | (2006.01) | |
| *A61P 35/00* | (2006.01) | |

(52) U.S. Cl.
CPC .......... *A61K 31/658* (2023.05); *A61K 31/282* (2013.01); *A61K 31/337* (2013.01); *A61K 31/565* (2013.01); *A61K 36/185* (2013.01); *A61P 35/00* (2018.01)

(58) Field of Classification Search
CPC .... A61K 31/05; A61K 31/192; A61K 31/352; A61K 31/565; A61K 31/658
See application file for complete search history.

(56) References Cited

U.S. PATENT DOCUMENTS

| | | |
|---|---|---|
| 10,098,867 B2 | 10/2018 | Javid et al. |
| 11,123,308 B2 | 9/2021 | Yu et al. |
| 2010/0273895 A1 | 10/2010 | Stinchcomb et al. |
| 2011/0086113 A1 | 4/2011 | Velasco Diez et al. |
| 2015/0086653 A1 | 3/2015 | Parolaro et al. |
| 2016/0136128 A1 | 5/2016 | Javid et al. |
| 2019/0282513 A1 | 9/2019 | Yerike |
| 2020/0253919 A1 | 8/2020 | Raz et al. |
| 2020/0408740 A1 | 12/2020 | Ballan et al. |
| 2021/0052512 A1 | 2/2021 | Guy et al. |
| 2021/0068444 A1 | 3/2021 | Alarcon et al. |
| 2021/0069608 A1 | 3/2021 | Galyuk |
| 2021/0085638 A1 | 3/2021 | Hospodor |
| 2021/0128521 A1 | 5/2021 | Palaio |
| 2021/0145764 A1* | 5/2021 | Lephart ................ A61K 31/728 |
| 2022/0000774 A1 | 1/2022 | Dely |
| 2022/0054429 A1 | 2/2022 | Nathan et al. |
| 2022/0062224 A1 | 3/2022 | Gubler et al. |
| 2022/0202765 A1 | 6/2022 | Altman et al. |
| 2022/0253919 A1 | 8/2022 | Denner |
| 2022/0331287 A1 | 10/2022 | Morgan et al. |
| 2023/0015268 A1 | 1/2023 | Altman et al. |
| 2023/0127098 A1 | 4/2023 | Capano et al. |
| 2023/0132189 A1 | 4/2023 | Capano et al. |
| 2023/0248747 A1 | 8/2023 | Altman et al. |
| 2023/0355645 A1 | 11/2023 | Storch et al. |

FOREIGN PATENT DOCUMENTS

| | | |
|---|---|---|
| CN | 108433880 A | 8/2018 |
| CN | 110063953 A | 7/2019 |
| EP | 3368024 A1 | 9/2018 |
| EP | 3449992 A1 | 3/2019 |
| EP | 3544598 A1 | 10/2019 |
| EP | 3915550 A1 | 12/2021 |
| EP | 3937914 A1 | 1/2022 |
| GB | 2516335 A | 1/2015 |
| RU | 2745687 C1 | 3/2021 |
| WO | WO/2013/165251 A1 | 11/2013 |
| WO | WO/2014/057067 A1 | 4/2014 |
| WO | WO/2016/187679 A1 | 12/2016 |
| WO | WO/2018/167038 A1 | 9/2018 |
| WO | WO/2019/003163 A2 | 1/2019 |
| WO | WO/2019/034113 A1 | 2/2019 |
| WO | WO/2019/106652 A1 | 6/2019 |

(Continued)

OTHER PUBLICATIONS

Olivas-Aguirre et al. J. Mol. Sci. 2021, 22, 8688, p. 1-14 (Year: 2021).*
Soltamox® Product Label (Midatech Pharma US Inc., Revised Apr. 2019, 38 pages) (Year: 2019).*
International Search Report issued in International Application No. PCT/US2023/077704 dated Feb. 28, 2024.
Hazekamp, et al., "Preparative Isolation of Cannabinoids from Cannabis sativa by Centrifugal Partition Chromatography", Journal of Liquid Chromatography & Related Technologies, vol. 27, No. 15, 2004, 2421-2439.

(Continued)

*Primary Examiner* — James D. Anderson
(74) *Attorney, Agent, or Firm* — Vos-IP, LLC

(57) ABSTRACT

Disclosed herein are methods for treating estrogen sensitive disease, specifically toward endometrial cancers, and compositions used to treat the estrogen sensitive disease. Methods for treating estrogen sensitive diseases comprise administering to a patient an effective amount of a *cannabis* extract in the presence of an elevated level of estrogen wherein the estrogen is endogenous estrogen or further comprises exogenous estrogen and wherein the methods may further comprise the addition of a chemotherapeutic agent.

2 Claims, 37 Drawing Sheets

(56) References Cited

FOREIGN PATENT DOCUMENTS

| WO | WO/2019/145552 A1 | 8/2019 |
| --- | --- | --- |
| WO | WO/2019/195943 A1 | 10/2019 |
| WO | WO/2019/222459 A1 | 11/2019 |
| WO | WO/2020/036655 A9 | 2/2020 |
| WO | WO/2020/163775 A1 | 8/2020 |
| WO | WO/2020/165878 A1 | 8/2020 |
| WO | WO/2020/183455 A1 | 9/2020 |
| WO | WO/2020/194237 A1 | 10/2020 |
| WO | WO/2020/209902 A1 | 10/2020 |
| WO | WO/2021/011790 A1 | 1/2021 |
| WO | WO/2021/016718 A1 | 2/2021 |
| WO | WO/2021/028646 A1 | 2/2021 |
| WO | WO/2021/099792 A1 | 5/2021 |
| WO | WO/2021/130728 A1 | 7/2021 |
| WO | WO/2021/158251 A1 | 8/2021 |
| WO | WO/2021/235977 A1 | 11/2021 |
| WO | WO/2021/240510 A1 | 12/2021 |
| WO | WO/2021/245522 A1 | 12/2021 |
| WO | WO/2022/013854 A1 | 1/2022 |
| WO | WO/2022/016160 A1 | 1/2022 |
| WO | WO/2022/018708 A1 | 1/2022 |
| WO | WO/2022/105952 A1 | 5/2022 |
| WO | WO/2022/118303 A1 | 6/2022 |
| WO | WO/2022/144878 A1 | 7/2022 |
| WO | WO/2022/165349 A1 | 8/2022 |
| WO | WO/2022/165439 A1 | 8/2022 |
| WO | WO/2022/215071 A1 | 10/2022 |
| WO | WO/2022/225658 A1 | 10/2022 |
| WO | WO/2023/287742 A1 | 1/2023 |
| WO | WO/2023/014818 A2 | 2/2023 |
| WO | WO/2023/062634 A1 | 4/2023 |

OTHER PUBLICATIONS

Jaidee, et al., "Kinetics of CBD, $\Delta^9$-THC Degradation and Cannabinol Formation in Cannabis Resin at Various Temperature and pH Conditions", Cannabis and Cannabinoid Research, vol. 7, No. 4, Aug. 9, 2022, 1-11.

Jin, et al., "Identification of Chemotypic Markers in Three Chemotype Categories of Cannabis Using Secondary Metabolites Profiled in Inflorescences, Leaves, Stem Bark, and Roots", Frontiers in Plant Science, vol. 12, Jul. 1, 2021, 1-16.

Armour, et al., "Self-Management Strategies Amongst Australian Women With Endometriosis: A National Online Survey", BMC Complementary and Alternative Medicine, vol. 19, No. 1, Jan. 15, 2019, 1-8.

Escudero-Lara, et al., "Disease-Modifying Effects of Natural $\Delta^9$-Tetrahydrocannabinol in Endometriosis-Associated Pain", eLife, vol. 9, Jan. 14, 2020, https://elifesciences.org/articles/50356.

Fonseca, et al., "Cannabinoid-Induced Cell Death in Endometrial Cancer Cells: Involvement of TRPV1 Receptors in Apoptosis", Journal of Physiology and Biochemistry, vol. 74, No. 2, Feb. 13, 2018, 261-272.

Fraguas-Sánchez, et al., "Enhancing Ovarian Cancer Conventional Chemotherapy Through the Combination With Cannabidiol Loaded Microparticles", European Journal of Pharmaceutics and Biopharmaceutics, vol. 154, Jul. 17, 2020, 246-258.

Go, et al., "Cannabidiol Enhances Cytotoxicity of Anti-Cancer Drugs in Human Head and Neck Squamous Cell Carcinoma", Scientific Reports, vol. 10, No. 1, Nov. 26, 2020, 1-11.

Griffiths, et al., "Cannabidiol Suppresses 3-Dimensional Ovarian Cancer Growth and May Enhance Potency of Classic and Epigenetic Therapies", Gynecologic Oncology, vol. 162, suppl. 1, Abstracts for the 2021 Society of Gynecologic Oncology 52nd Annual Meeting on Women's Cancer, Aug. 18, 2021, S102-S103.

Kenyon, et al., "Report of Objective Clinical Responses of Cancer Patients to Pharmaceutical-Grade Synthetic Cannabidiol", Anticancer Research, vol. 38, No. 10, Oct. 1, 2018, 5831-5835.

Lazarjani, et al., "Processing and Extraction Methods of Medicinal Cannabis: A Narrative Review", Journal of Cannabis Research, vol. 3, Jul. 19, 2021, 1-15.

Marinelli, et al., "The Effects of Cannabidiol and Prognostic Role of TRPV2 in Human Endometrial Cancer", International Journal of Molecular Sciences, vol. 21, No. 15, Jul. 29, 2020, 1-22.

Marinotti, et al., "Differentiating Full-Spectrum Hemp Extracts from CBD Isolates: Implications for Policy, Safety and Science", Journal of Dietary Supplements, vol. 17, No. 5, Jun. 16, 2020, 517-526.

Ökten, et al., "Cannabidiol as a Potential Novel Treatment for Endometriosis by Its Anti-Inflammatory and Anti-Oxidative Effects in an Experimental Rat Model", Human Reproduction, vol. 37, issue supp. 1, Jun. 30, 2022, i111.

Rais, et al., "Phytochemicals in the Treatment of Ovarian Cancer", Frontiers in Bioscience-Elite, vol. 9, No. 1, Jan. 1, 2017, 67-75.

Rush, et al., "Cannabidiol: Assessing Activity in Ovarian and Endometrial Carcinoma Cell Lines", Abstracts for the 2021 Society of Gynecologic Oncology 52nd Annual Meeting on Women's Cancer, Featured Posters 188—Poster Session, vol. 162, suppl. 1, Aug. 1, 2021, https://doi.org/10.1016/S0090-8258(21)00839-8.

Sumanasekera, et al., "Hemp Extract With Specific Anti-Cancer Properties Against Ovarian Cancer", The FASEB Journal Special Issue: Experimental Biology 2021 Meeting Abstracts, vol. 35, No. S1, May 14, 2021, https://doi.org/10.1096/fasebj.2021.35.S1.02877.

Van Weelden, et al., "Anti-Estrogen Treatment in Endometrial Cancer: A Systematic Review", Frontiers in Oncology, vol. 9, May 7, 2019, 1-12.

\* cited by examiner

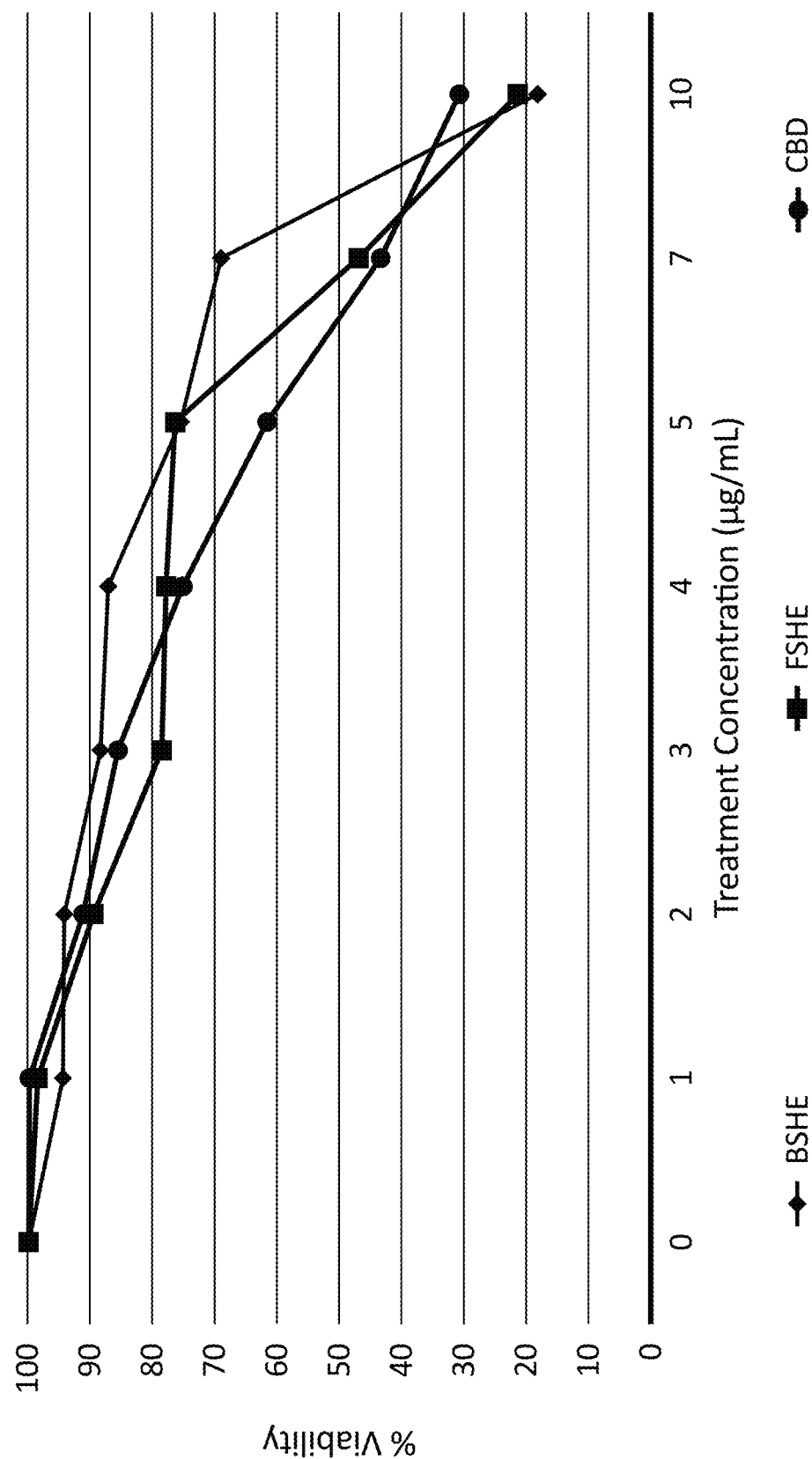

Cannabinoid Effect on the Inhibition of Endometrial Cancer PDX Tumor Volume

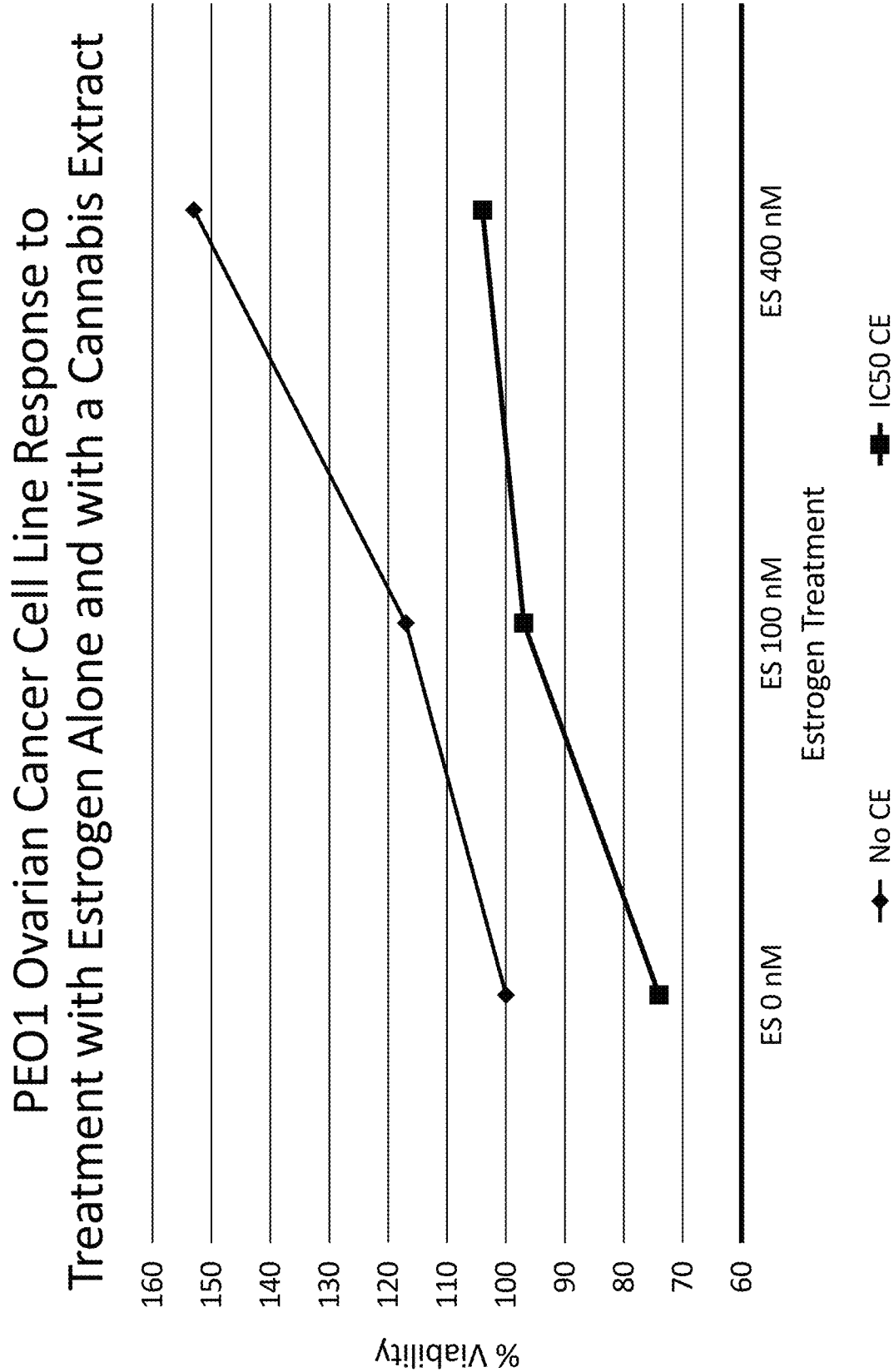

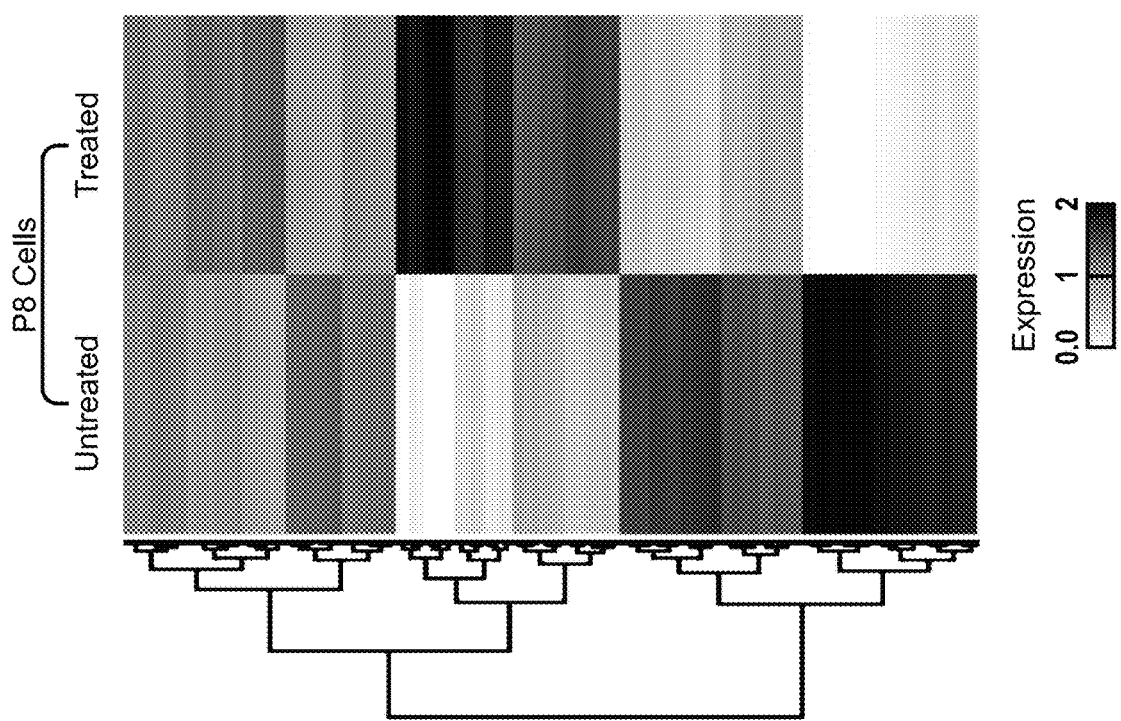
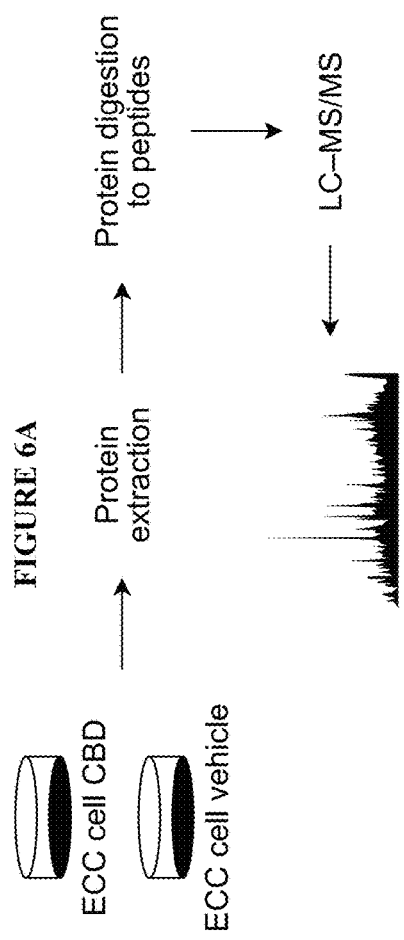
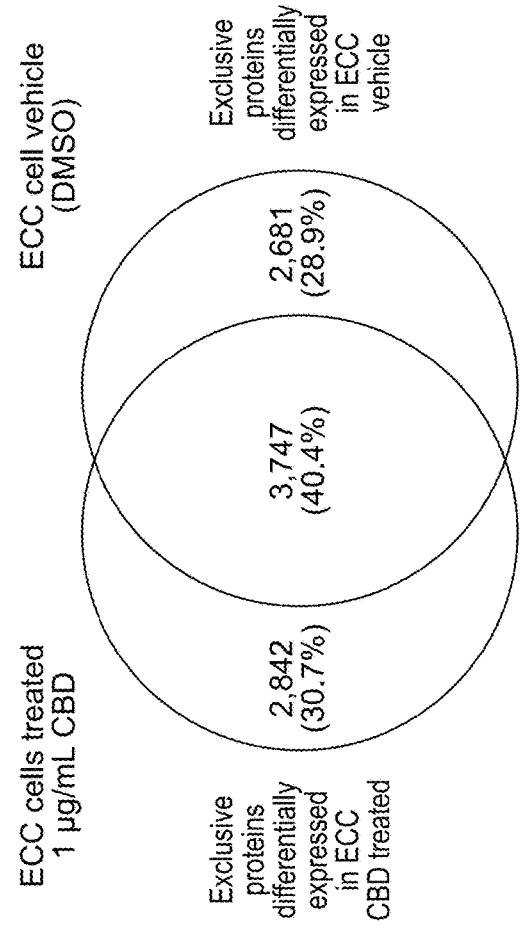
FIGURE 6A
FIGURE 6B
FIGURE 6C

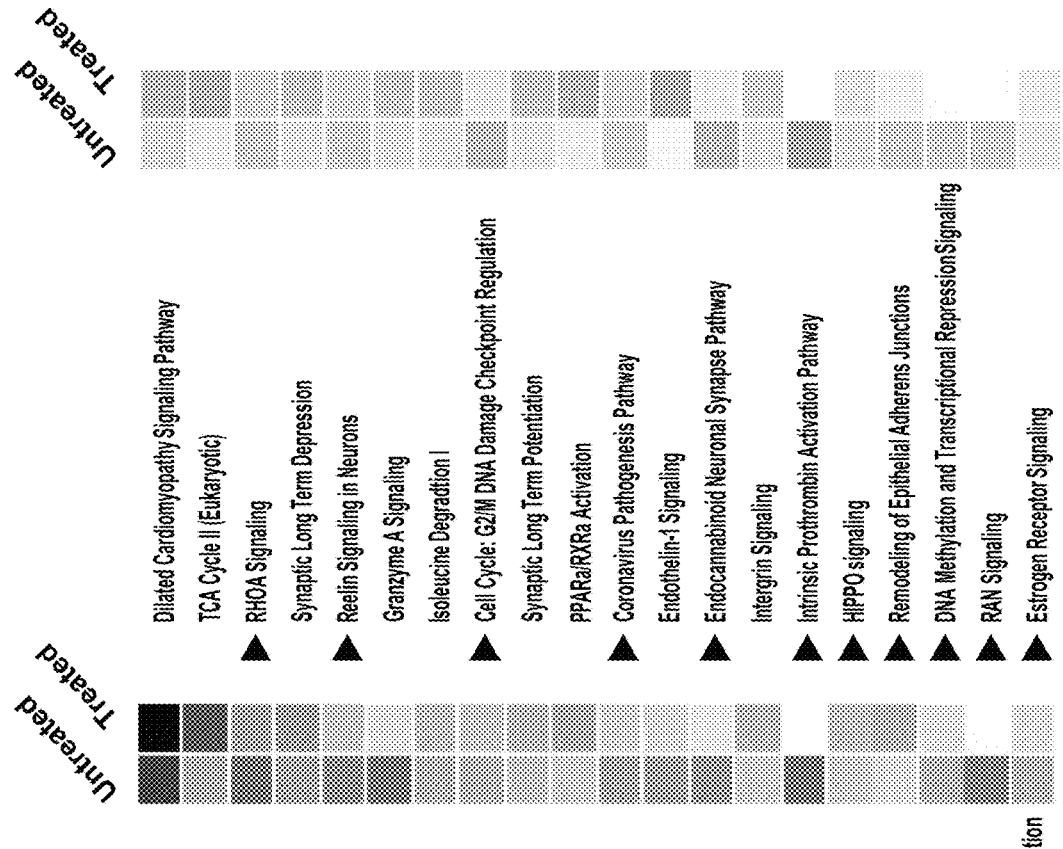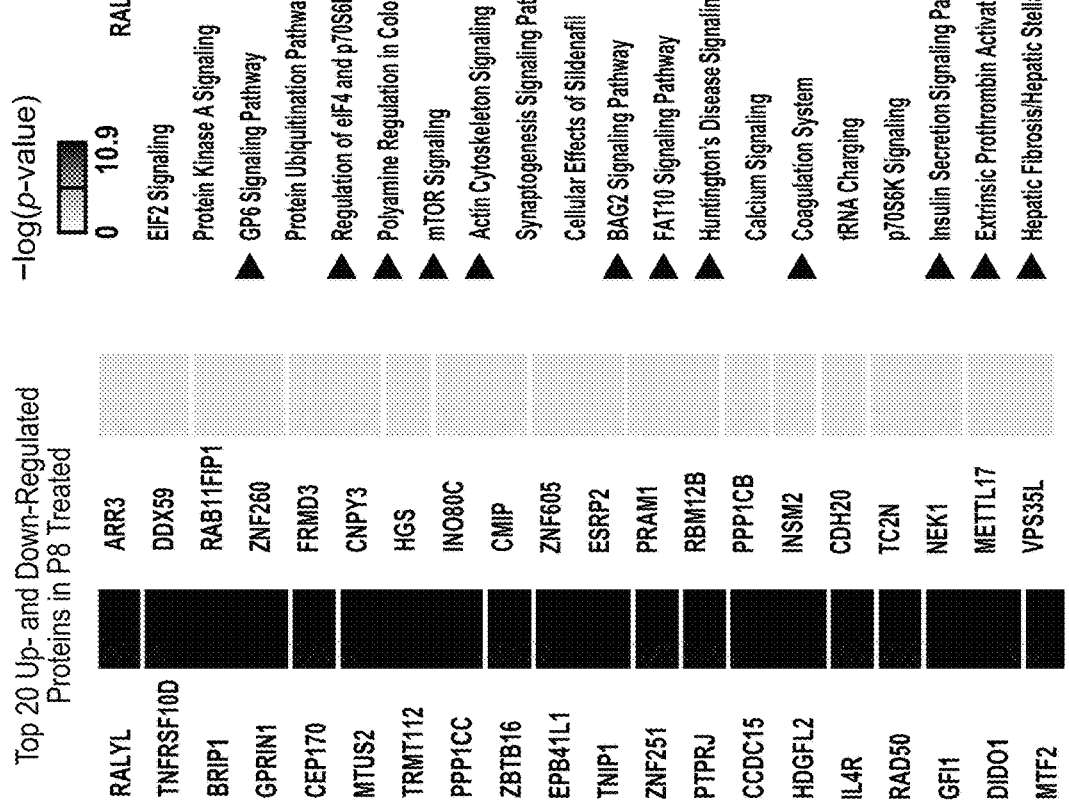

Cannabinoid Receptor 2 Protein Expression in Endometrial Cancer Patient Samples

Endometrial Cancer (Endometrioid Type)

Cannabinoid Receptor 1 Protein Expression in Endometrial Cancer Patient Samples

Endometrial Cancer (Endometrioid Type)

Effects of Paclitaxel and Cannabis Extracts (IC50) + Paclitaxel on Grade 2 Endometrial Cancer Organoids

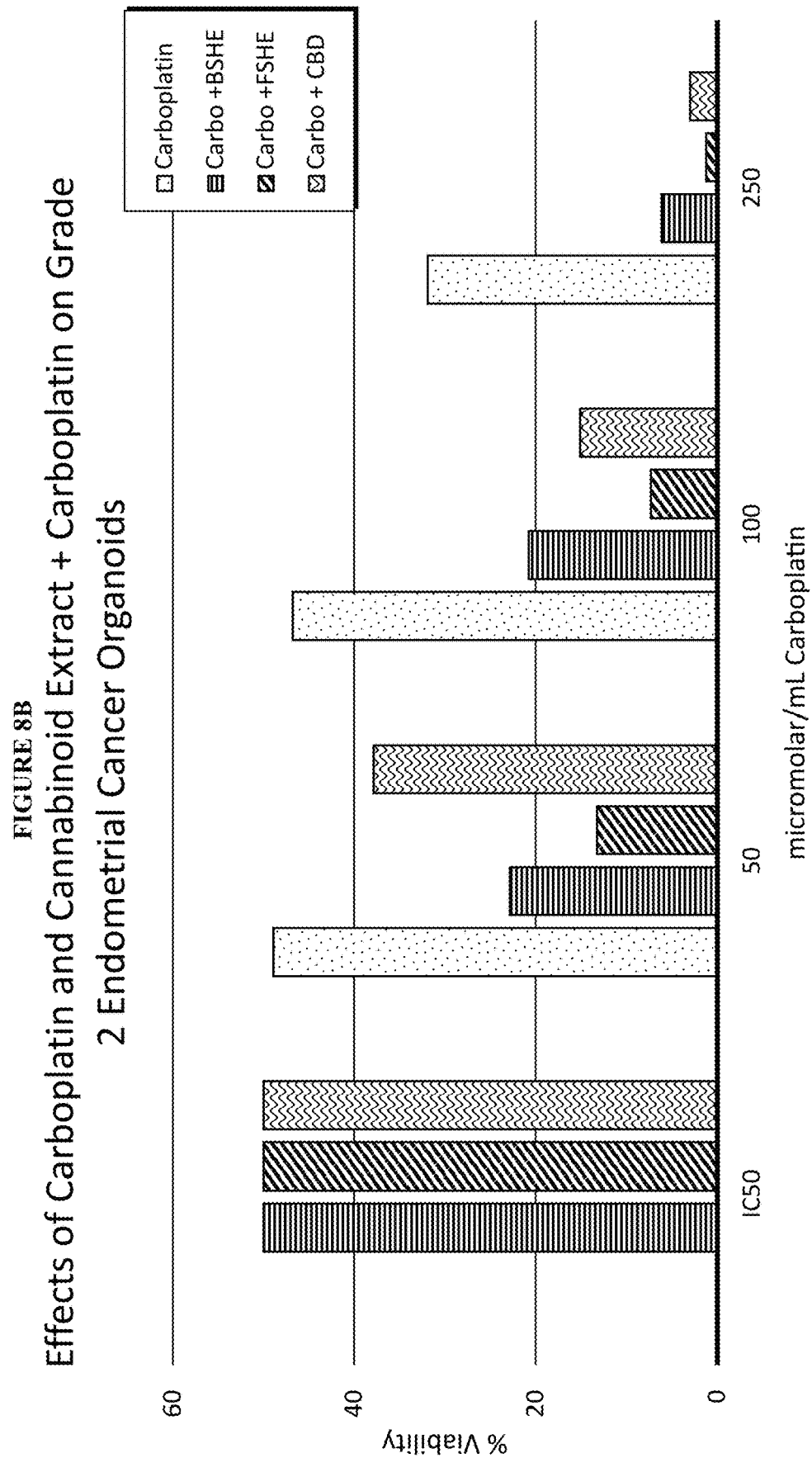

Effects of Paclitaxel and Paclitaxel + Cannabis Extract (IC50) on Grade 3 Endometrial Cancer Tumor Cells

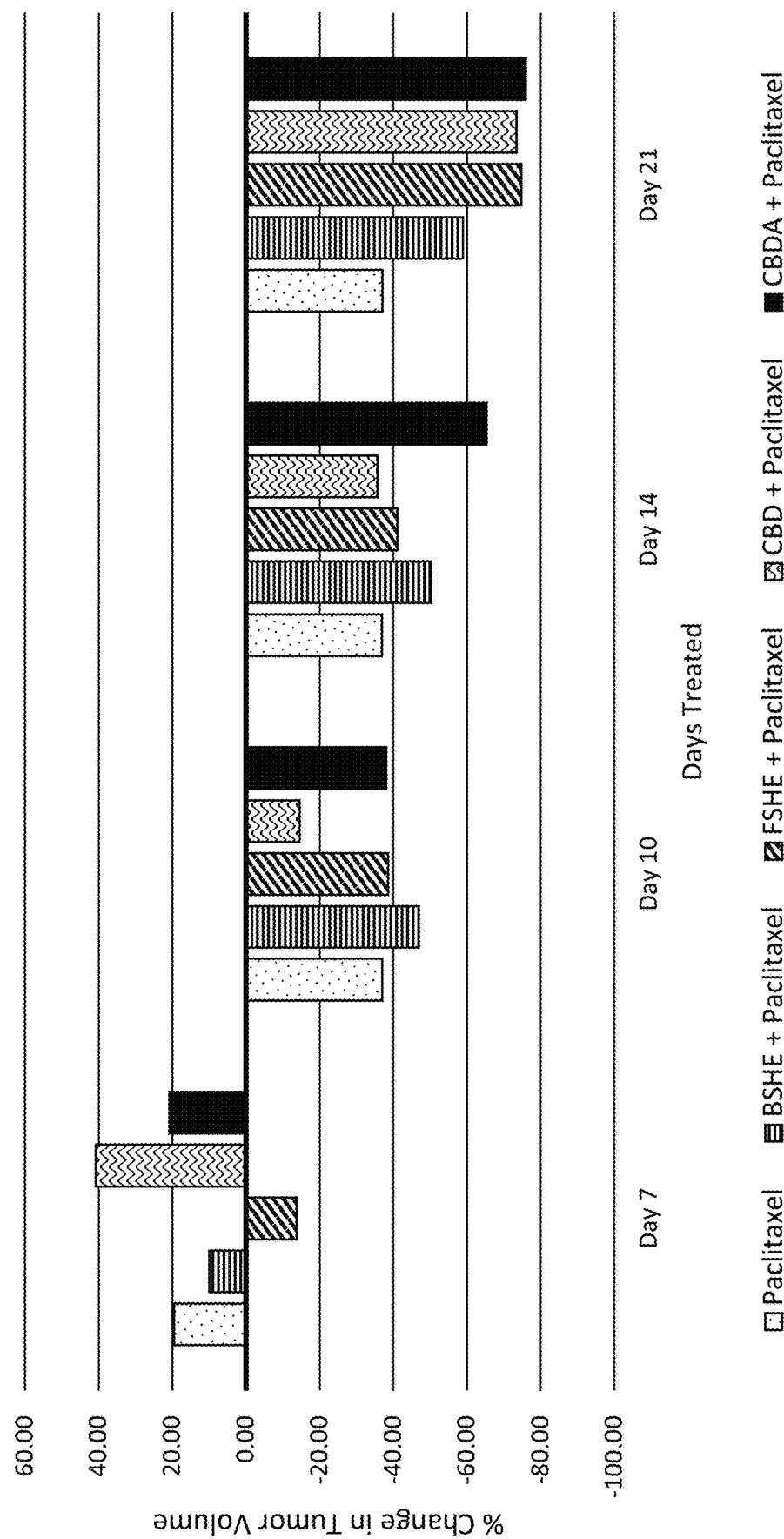

Effects pH and Cannabinoid Extract (10 μg/mL) on Ovarian Cancer Organoid Viability

METHODS OF TREATING ESTROGEN SENSITIVE DISEASES WITH CANNABIS EXTRACT

CROSS-REFERENCE TO RELATED APPLICATIONS

This application claims the benefit of U.S. Provisional Patent Application No. 63/381,017 filed on Oct. 26, 2022, with the United States Patent and Trademark Office, the contents of which are incorporated herein by reference in their entirety.

FIELD OF THE INVENTION

The inventions disclosed herein are related to compositions and therapeutic treatments of estrogen sensitive diseases through administration of an effective amount of *cannabis* extracts alone, in combination with estrogen, and/or with a chemotherapeutic agent. The *cannabis* extracts comprise one or more cannabinoids, and specifically therapeutic amounts of cannabidiol (CBD) and often include one or more additional cannabinoid, terpene, and/or other molecules within the *cannabis* extract.

BACKGROUND OF THE INVENTION

Estrogens are endogenously produced to regulate physiological processes in cells sensitive to estrogen, such as endometrial layers lining the uterus. Other cells are not estrogen sensitive and as such their physiology is not necessarily influenced by estrogen. In a healthy environment, the body responds to estrogens as it should, and physiological processes are modulated accordingly. When a change in estrogen concentration and/or signaling occurs, however, a body may exhibit one or more diseases/disorders such as various forms of cancer (e.g., breast, ovarian, prostrate), osteoporosis, cardiac disease, and vascular disease, to name a few examples. Many of these diseases are believed to be due to abnormal estrogen receptor (ER) signaling as ERs mediate many physiological and pathophysiological processes, not just reproductive processes. In turn, amounts of estrogens available to the body can also affect ER signaling as estrogens can bind to ER receptors. There are several types of ERs and ER/estrogen mediated processes are varied and widespread. Universal physiological/pathophysiologic outcomes due to estrogen-, estrogen receptor-, and/or non-estrogen receptor-mediated processes are not a given. For example, estrogen, via one type of estrogen receptor (e.g., ERα) may promote disease whereas, via the same or different receptor (e.g., ERβ, G-protein coupled estrogen receptor), may inhibit the same disease/produce a different physiological outcome.

Under normal conditions, estrogens can mediate physiological effects via "genomic" and "nongenomic" signaling. Generally, ER genomic signaling refers to the production or inhibition of certain mRNAs/proteins by complex interactions with ES promoter regions on DNA. In turn, the produced/inhibited mRNAs/proteins can regulate processes such as proliferation, autophagy, survival, apoptosis, differentiation, immunity, and more. Nongenomic ER effects can still affect gene transcription; albeit via different mechanisms. Other nongenomic ER effects include influencing ion channels and/or certain enzymes. In a disease state, however, any one of these or other estrogen-mediated effects can go wrong. Thus, estrogen mediated effects, whether normal physiological or pathophysiological are complex, fascinating, and have been and will continue to be the subject of many lifetimes of study.

As estrogen is a sex hormone, it plays a role in normal reproductive function. It has been, however, linked to reproductive diseases/disorders such as endometriosis, polycystic ovarian syndrome, and several types of cancers. The complexity of how estrogens may exert their effects in any one of these diseases/disorders can be appreciated from the above-mentioned generalizations. Even with all we do know, women still suffer from estrogen-mediated disease, and treatments are still inadequate. For example, there are many types of breast cancers, some of which are estrogen receptor positive (ER+), meaning that one or more estrogen receptors are expressed/overexpressed and hence may stimulate tumor growth. Since most breast cancers are ER+, the treatment of choice is to alter the estrogen-receptor interaction such as via a selective estrogen receptor modulators (SERMs), which suppress/inhibit estrogens from acting at the receptors in susceptible breast tissues. Patients, however, can develop a resistance to SERMS and/or suffer from side effects. Further, treating breast cancer with certain anti-estrogens has been associated with an increase in endometrial cancer as some anti-estrogen can act as an estrogen-like ligand in endometrial tissue rather than block estrogen effects.

Certain ovarian and endometrial cancers have also been associated with increased estrogen exposure. Again, estrogen action via one or more receptors has been implicated in these diseases. For example, certain ovarian cancers have been associated with higher than normal expression of certain types of estrogen receptors, and certain estrogen receptor/estrogens have been associated with cell growth and migration. Similarly, Type I endometrial cancers are thought to be hormone (e.g., estrogen) driven and can be associated with high levels of certain estrogen receptor expression. Again, treatment of these cancers can include anti-hormone therapy such as by using a SERM, progestins, and/or aromatase inhibitors. Although not a cancer, endometriosis, including ovarian endometrioma, and deep endometriosis, has been categorized as an estrogen-dependent condition. That is, excess estrogen is believed to promote the development and progression of endometriosis lesions via ER activation. In each of these cases, anti-hormone therapy is recommended, especially in patients that still want to have children and those who are not candidates for surgery. Hormone therapy can block the production of estrogen, act at one or more estrogen receptors, counter estrogen dominance (e.g., progestins), or combinations thereof. Nonetheless, surgery to remove cancerous tumors is typical with estrogen-mediated disease and cancers. The extent to which cancerous tissue is, or can be, removed may depend on the grade and/or stage of the particular cancer. Further, certain estrogen mediated cancers may include chemotherapy as first line therapy or an adjuvant therapy. In other estrogen-mediated cancers chemotherapy is contraindicated.

Cannabinoids have been found to be beneficial in treating various diseases such as certain types of epilepsy. Cannabinoids are also being tested for anti-cancer properties. Examples of work done in this area follow.

WO 2020/163775 ("Alugupalli") teaches a nanoemulsion with a mean particle diameter size of up to 900 nm. The nanoemulsion included 6% CBD. Tumors, however, continued to grow when treated with the nanoemulsion. Moreover, Alugupalli expressly excludes using the nanoemulsion to treat estrogen-receptor positive cancers, and if estrogen receptors are present, he teaches selectively binding/inhibiting the estrogen receptors.

A further reference, entitled Cannabidiol enhances cytotoxicity of anti-cancer drugs in human head and neck squamos cell carcinoma, to Go, suggests cytotoxic effects of CBD. However, Go shows that CBD in treatment is only suitable to reduce the rate of growth. Go does not actually teach that the tumor volume of mice is reduced. Further, as Go is interested in head and neck squamous cell carcinoma he does not even mention estrogen or estrogen mediated effects on estrogen sensitive cancers.

Neither the prior art nor our previous work specifically addresses the relevance of estrogen-mediated effects in treating cancers or other diseases/disorders. As such we were interested in determining the efficacy of *cannabis* extracts in environments that emulated estrogen dominance, unopposed estrogen, and/or excess estrogen, and extrapolating our finding to provide methods of treating cancers that are sensitive to estrogens. Our results were extremely unexpected and provides a new treatment paradigm that provides unexpectedly superior clinical responses than the prior art.

SUMMARY OF THE INVENTION

In a preferred embodiment, a *cannabis* extract for use in a method of treating estrogen sensitive disease comprising: (a) an effect amount of *cannabis* extract (CE) comprising from about 50% to about 99.9% by weight cannabidiol (CBD); and (b) an amount of estrogen comprising from about 0.25 mg to about 25 mg of estrone, 17β-estradiol, estriol, estetrol, estradiol, genistein, zearalenone, ethinylestradiol, estradiol valerate, mestranol, estropipate, tamoxifen, or combinations thereof.

In a further embodiment, the *cannabis* extract wherein the *cannabis* extract is administered orally, intravaginally, rectally, intravenously, intramuscularly, in a pellet, in an intrauterine device, mucosally, nasally, transdermally, or combinations thereof.

In a further embodiment, the *cannabis* extract for use in an estrogen sensitive disease selected from the group consisting of: type 1 cancer, grade 1 cancer, grade 2 cancer, an estrogen receptor positive cancer, an estrogen sensitive endometrial cancer, and estrogen receptor positive endometrial cancer, a type 1 endometrial cancer, a grade 1 endometrial cancer, a grade 2 endometrial cancer, or an endometrial cancer comprising a PTEN, TP53, POLE, or PIK3R1 mutation.

In a further embodiment, the *cannabis* extract for use wherein said *cannabis* extract is selected from a full spectrum hemp extract (FSHE), a broad spectrum hemp extract (BSHE), a CBD isolate, and cannabidiolic acid (CBDA), optionally wherein the BSHE or FSHE comprises (i) from 50% to 99% by weight of CBD, (ii) at least one other cannabinoid selected from Δ-9-tetrahydrocannabinol (Δ9-THC), tetrahydrocannabinolic acid (THCA), tetrahydrocannabivarin (THCV), Δ-8-tetrahydrocannabinol (Δ8-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), or (iii) combinations thereof.

In a preferred embodiment, a *cannabis* extract for use wherein said *cannabis* extract comprises between 10 mg and 500 mg CBD per dose.

In a further embodiment, the *cannabis* extract further comprising administering an effective amount of chemotherapy to the patient, buffering the CE to a pH of between 2 and 6, or both.

In a preferred embodiment, a mucosal composition for use in a method of treating estrogen sensitive cancer in a patient wherein said mucosal composition comprises a *cannabis* extract and a pharmaceutically acceptable excipient.

In a preferred embodiment, a mucosal composition for use wherein the composition comprises (i) an oil or fat as a carrier and/or (ii) at least one terpene, at least one polyphenol, at least one essential fatty acid, at least one phytonutrient, or a combination thereof, optionally wherein the at least one terpene, at least one polyphenol, at least one essential fatty acid, at least one phytonutrient, or combination thereof make up between 1% and 50% by weight of the total weight of the composition, further optionally wherein: (a) the terpene is selected from β-myrcene, β-caryophyllene, linalool, α-pinene, citral, D-limonene, eucalyptol, and combinations thereof; and/or (b) the polyphenol is selected from a catechin, quercetin, cannflavin A/B/C, rutin, chlorogenic acid, and combinations thereof, and/or (c) the essential fatty acid is selected from an omega 3 acid, an omega 6 acid, an omega 9 acid, and combinations thereof, and/or (d) the phytonutrient is selected from a sterol, carotene, an aliphatic alcohol, a mineral, and combinations thereof.

In a preferred embodiment, a mucosal composition for use wherein: (a) the mucosal composition comprises a dose of between 25 mg and 4,250 mg CBD and the method comprises administering the composition to the patient via insertion to a mucosal surface selected from oral mucosa, rectum, vagina, or nasal passages; and/or (b) the method comprises administering at least two doses of the mucosal composition to the patient per day, wherein each dose of the mucosal composition comprises between 10 mg and 2,125 mg *cannabis* extract; and/or (c) the mucosal composition has an acidic pH, preferably a pH between 3.5 and 6.

In a further embodiment, a *cannabis* extract for use wherein said method is a method for treating estrogen sensitive cancer and the method comprises administering the *cannabis* extract to the patient concomitantly via a mucosal formulation, preferably wherein the *cannabis* extract is a full spectrum hemp extract (FSHE) or a broad spectrum hemp extract (BSHE).

In a preferred embodiment, a pharmaceutical composition for use in a method of treating an estrogen sensitive cancer wherein said pharmaceutical composition comprises a *cannabis* extract comprising an effective amount of CBD and administering the pharmaceutical composition to a patient that is estrogen is estrogen positive.

In a further embodiment, a pharmaceutical composition for use wherein the composition further comprises: (a) a carrier; and/or (b) at least one additional cannabinoid selected from CBDV, THC, CBG, CBN, CBC, CBDA, and combinations thereof, and/or (c) at least one terpene, preferably wherein the terpene is selected from β-myrcene, β-caryophyllene, linalool, α-pinene, citral, D-limonene, eucalyptol, and combinations thereof, and/or (d) at least one polyphenol, preferably wherein the polyphenol is selected from a catechin, quercetin, cannflavin A/B/C, rutin, chlorogenic acid, and combinations thereof, and/or (e) an essential fatty acid, preferably wherein the essential fatty acid is selected from an omega 3 acid, an omega 6 acid, an omega 9 acid, and combinations thereof, and/or (f) a phytonutrient, preferably wherein the phytonutrient is selected from a tocopherol, a sterol, carotene, an aliphatic alcohol, a mineral, and combinations thereof, and/or (g) an estrogen selected from one or more of estrone, 17β-estradiol, estriol, estetrol, estradiol, genistein, zearalenone, ethinylestradiol, estradiol valerate, mestranol, estropipate, tamoxifen.

In a further embodiment, the pharmaceutical composition wherein the estrogen comprises an amount of from about 0.25 mg to about 25 mg.

In a further embodiment, the pharmaceutical composition wherein the composition is administered via an oral form, oral mucosal form, intravaginal form, nasal mucosal form, rectal form, injectable form, a pellet form, a transdermal form, or combinations thereof.

In a further embodiment, the pharmaceutical composition wherein the effective amount of the *cannabis* extract comprises between 10 mg and 4,250 mg of CBD per day.

In a further embodiment, the pharmaceutical composition wherein administration of the CE is a dose given at least once a day, at least twice a day, or at least three times a day.

In a further embodiment, the pharmaceutical composition wherein the estrogen mediated cancer is a grade 1, grade 2, or grade 3 endometrial cancer.

In a further embodiment, the pharmaceutical composition further comprising an effective amount of a chemotherapeutic agent.

In a further embodiment, the pharmaceutical composition wherein the *cannabis* extract comprises CBDA at a concentration of between 0.1% and 10%.

In a preferred embodiment, a method of treating an estrogen sensitive cancer comprising: (a) administering to a subject an effect amount of *cannabis* extract (CE) comprising from about 50% to about 99.9% by weight cannabidiol (CBD); and (b) either (i) administering an effective amount of estrogen to said patient, (ii) administering an amount of estrogen to said patient to bring the total estrogen within the patient to an effective amount, or (iii) determining that the patient is producing an effective amount of estrogen.

In a further embodiment, the method wherein the effective amount of estrogen is a serum level of greater than or equal to 300 pg/mL. In a further embodiment, the method wherein administering an effective amount of estrogen or administering an amount of estrogen comprises administering estrogen orally, intravaginally, rectally, intravenously, intramuscularly, in a pellet, in an intrauterine device, mucosally, nasally, transdermally, or combinations thereof. In a further embodiment, the method wherein administering an amount of estrogen further comprises administering the amount of estrogen in a composition comprising the CE.

In a further embodiment, the method wherein the effective amount of estrogen is a serum level of between about 600 pg/mL and 150,000 pg/mL.

In a further embodiment, the method wherein the estrogen sensitive cancer is selected from the group consisting of: type 1 cancer, grade 1 cancer, grade 2 cancer, an estrogen receptor positive cancer, an estrogen sensitive endometrial cancer, and estrogen receptor positive endometrial cancer, a type 1 endometrial cancer, a grade 1 endometrial cancer, a grade 2 endometrial cancer, or an endometrial cancer comprising a PTEN, TP53, POLE, or PIK3R1 mutation.

In a further embodiment, the method wherein administering to the subject an effective amount of the CE comprises: (i) administering an amount of CE that upregulates proteins associated with endometrial cancer signaling, mitochondrial dysfunction, or remodeling of epithelial adherens junctions, or combinations thereof, (ii) administering an amount of CE that modulates expression of one or more proteins that are part of estrogen receptor signaling processes, modulate estrogen-mediated protein transcription and/or translation, or both; (iii) administering an amount of CE that modulates estrogen-mediated protein transcription and/or translation in response to estrogen receptor alpha activation; or (iv) administering an amount of CE that induces downregulation of MYC, ESRα, BRCA1, ERBB2, VEGF, or combinations thereof.

In a further embodiment, the method wherein administering an effective amount of an estrogen, administering an amount of estrogen, or determining that the patient is producing an effective amount of endogenous estrogen further comprises, ensuring that the effective amount of estrogen is not adversely affected by an anti-estrogen therapy.

In a further embodiment, the method further comprising administering an effective amount of chemotherapy to the patient, or buffering the CE to a pH of between 2 and 6, or both.

In a preferred embodiment, a method for treating an estrogen sensitive cancer comprising administering to patient producing an effective amount of endogenous estrogen or being treated with an amount of exogenous estrogen to reach in vivo amount of estrogen that is therapeutically acceptable, a therapeutically effective amount of a *cannabis* extract comprising cannabidiol (CBD) and at least one other cannabinoid in a by weight ratio of from about 70:40 to about 99.9:0.1 CBD:other cannabinoid, wherein the at least one other cannabinoid is selected from the group consisting of: Δ-9-tetrahydrocannabinol ($Δ^9$-THC), tetrahydrocannabinolic acid (THCA), tetrahydrocannabivarin (THCV), Δ-8-tetrahydrocannabinol ($Δ^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

In a further embodiment, the method wherein an effective amount of endogenous estrogen, exogenous estrogen, or combination thereof is an amount that synergistically augments CE induced cancer cell apoptosis. In a further embodiment, the method wherein the *cannabis* extract is combined with an excipient, a buffer to adjust the pH of the formulation to between about 3.5 and about 6.5, or an effective or other amount of estrogen, or combinations thereof.

In a further embodiment, the method wherein the estrogen is present in or administered to the patient in an amount that synergistically acts with the *cannabis* extract to reduce the presence of cancerous cells, the metabolic activity of the cancerous cells, or both, wherein the presence of cancerous cells, the metabolic activity of the cancerous cells or both are determined before treating the patient with *cannabis* extract.

In a further embodiment, the method wherein the effective amount of endogenous estrogen, exogenous estrogen, or both is a serum level from between about 30 pg/mL to about 20,000 pg/mL. In a further embodiment, the method wherein the *cannabis* extract and the exogenous estrogen are administered by different routes.

In a further embodiment, the method wherein the estrogen sensitive cancer is selected from the group consisting of a grade 1 endometrial cancer, a grade 2 endometrial cancer, or a type 1 endometrial cancer.

In a preferred embodiment, a composition comprising a *cannabis* extract and an estrogen; wherein the *cannabis* extract comprises between 50 and 100% by weight of cannabidiol; and wherein the estrogen is provided as estrone, 17β-estradiol, estriol, estetrol, estradiol, genistein, zearalenone, ethinylestradiol, estradiol valerate, mestranol, estropipate, tamoxifen or combinations thereof.

In a further embodiment, the composition wherein said composition is for use in a method of treating an estrogen sensitive disease. In a further embodiment, the composition wherein the estrogen-sensitive disease is selected from the group consisting of: an endometrial cancer, a grade 1 endometrial cancer, a grade 2 endometrial cancer, or a type 1 endometrial cancer.

In a preferred embodiment, a *cannabis* extract for use in a method of treating estrogen sensitive cancer in a patient wherein said *cannabis* extract comprises between about 50% and 100% by weight cannabidiol (CBD) and wherein the method of treating the estrogen sensitive cancer comprises: (a) administering between 0.025 mg and 25 mg of estrogen to the patient; and/or (b) determining that the patient is producing at least about 30 pg/mL to about 300 pg/mL estrogen; and/or (c) administering an effective amount *cannabis* extract together with an effective amount of estrogen; and/or (d) administering an effective amount of *cannabis* extract separate from an effective amount of estrogen.

In a further embodiment, a *cannabis* extract for use wherein said *cannabis* extract is selected from a full spectrum hemp extract (FSHE), a broad spectrum hemp extract (BSHE), a CBD isolate, and cannabidiolic acid (CBDA), optionally wherein the BSHE or FSHE comprises (i) from 50% to 99% by weight of CBD, (ii) at least one other cannabinoid selected from Δ-9-tetrahydrocannabinol (Δ9-THC), tetrahydrocannabinolic acid (THCA), tetrahydrocannabivarin (THCV), Δ-8-tetrahydrocannabinol (Δ8-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), or (iii) combinations thereof.

In a further embodiment, a *cannabis* extract for use wherein said *cannabis* extract comprises between 10 mg and 500 mg CBD per dose.

In a preferred embodiment, a *cannabis* extract for use wherein: (a) the method comprises administering the *cannabis* extract to the patient via an oral dose, oral mucosal dose, intravaginal dose, or combinations thereof, and/or (b) the method comprises administering a dose of the *cannabis* extract to the patient at least once every three days, preferably at least once a day, at least twice a day, or at least three times a day; and/or (c) the method comprises administering an amount of the *cannabis* extract sufficient to generate a concentration of at least 10 μg/mL of the *cannabis* extract at a target tissue in the patient, preferably wherein the target tissue is an estrogen sensitive uterine cancerous tissue; and/or (d) the method comprises administering an amount of the *cannabis* extract sufficient to reach an effective therapeutic level as measured through systemic plasma levels of CBD; and/or (e) the method comprises administering between 20 mg and 4,250 mg of CBD to the patient per day; and/or (f) the *cannabis* extract is formulated at an acidic pH, preferably at a pH between 3.5 and 6.

In a further embodiment, a *cannabis* extract for use wherein: (a) the estrogen sensitive cancer has metastasized; and/or (b) the estrogen sensitive cancer is a chemoresistant cancer; and/or (c) the estrogen sensitive cancer is chemonaïve.

In a further embodiment, a *cannabis* extract for use wherein said *cannabis* extract comprises between 50% and 100% by weight CBD and wherein the method comprises administering the *cannabis* extract to the patient via intravaginal administration, preferably wherein: (a) the *cannabis* extract is selected from a full spectrum hemp extract (FSHE), a broad spectrum hemp extract (BSHE), and a CBD isolate; and/or (b) the *cannabis* extract comprises CBDA.

In a preferred embodiment, a mucosal composition for use in a method of treating estrogen sensitive cancer in a patient wherein said mucosal composition comprises a *cannabis* extract and a pharmaceutically acceptable excipient.

In a preferred embodiment, a mucosal composition for use wherein the composition comprises (i) an oil or fat as a carrier and/or (ii) at least one terpene, at least one polyphenol, at least one essential fatty acid, at least one phytonutrient, or a combination thereof, optionally wherein the at least one terpene, at least one polyphenol, at least one essential fatty acid, at least one phytonutrient, or combination thereof make up between 1% and 50% by weight of the total weight of the composition, further optionally wherein: (a) the terpene is selected from β-myrcene, β-caryophyllene, linalool, α-pinene, citral, D-limonene, eucalyptol, and combinations thereof; and/or (b) the polyphenol is selected from a catechin, quercetin, cannflavin A/B/C, rutin, chlorogenic acid, and combinations thereof, and/or (c) the essential fatty acid is selected from an omega 3 acid, an omega 6 acid, an omega 9 acid, and combinations thereof, and/or (d) the phytonutrient is selected from a sterol, carotene, an aliphatic alcohol, a mineral, and combinations thereof.

In a preferred embodiment, a mucosal composition for use wherein: (a) the mucosal composition comprises a dose of between 25 mg and 4,250 mg CBD and the method comprises administering the composition to the patient via insertion to a mucosal surface selected from oral mucosa, rectum, vagina, or nasal passages; and/or (b) the method comprises administering at least two doses of the mucosal composition to the patient per day, wherein each dose of the mucosal composition comprises between 10 mg and 2,125 mg *cannabis* extract; and/or (c) the mucosal composition has an acidic pH, preferably a pH between 3.5 and 6.

In a further embodiment, a *cannabis* extract for use wherein said method is a method for treating estrogen sensitive cancer and the method comprises administering the *cannabis* extract to the patient concomitantly via a mucosal formulation, preferably wherein the *cannabis* extract is a full spectrum hemp extract (FSHE) or a broad spectrum hemp extract (BSHE).

In a further embodiment, a *cannabis* extract for use wherein said method comprises coadministering to a patient, within an estrogen rich environment, an effective amount of said *cannabis* extract and an effective amount of a chemotherapeutic agent.

In a preferred embodiment, a chemotherapeutic agent for use in a method of treating estrogen sensitive cancer wherein said method comprises coadministering to a patient an effective amount of said chemotherapeutic agent and an effective amount of a *cannabis* extract.

In a further embodiment, a *cannabis* extract for use or a chemotherapeutic agent for use wherein: (a) the chemotherapeutic agent is selected from paclitaxel, carboplatin, doxorubicin, cisplatin, docetaxel, fluorouracil, methotrexate, cetuximab, and combinations thereof; and/or (b) the estrogen sensitive cancer is a chemoresistant cancer; and/or (c) the method comprises a first step of determining estrogen sensitivity of a cancerous tissue in a patient and a subsequent step of administering to the patient an effective amount of the *cannabis* extract, within an estrogen rich environment, and an effective amount of the chemotherapeutic agent upon confirmation of estrogen sensitivity; and/or (d) the effective amount of the chemotherapeutic agent is at least 50% less than an indicated dose of the chemotherapeutic agent when administered in the absence of the *cannabis* extract; and/or (e) the method comprises administering the *cannabis* extract to the patient in an amount of between 20 mg and 4,250 mg per day; and/or (f) administering estrogen to the patient to create the estrogen rich environment or in the absence of an antiestrogen treatment to allow for endogenous estrogen production.

In a preferred embodiment, a pharmaceutical composition for use in a method of treating an estrogen sensitive cancer wherein said pharmaceutical composition comprises a *cannabis* extract comprising an effective amount of CBD and administering the pharmaceutical composition in an environment where estrogen is not suppressed or inhibited.

In a further embodiment, a pharmaceutical composition for use wherein the composition further comprises: (a) a carrier; and/or (b) at least one additional cannabinoid selected from CBDV, THC, CBG, CBN, CBC, CBDA, and combinations thereof, and/or (c) at least one terpene, preferably wherein the terpene is selected from β-myrcene, β-caryophyllene, linalool, α-pinene, citral, D-limonene, eucalyptol, and combinations thereof, and/or (d) at least one polyphenol, preferably wherein the polyphenol is selected from a catechin, quercetin, cannflavin A/B/C, rutin, chlorogenic acid, and combinations thereof, and/or (e) an essential fatty acid, preferably wherein the essential fatty acid is selected from an omega 3 acid, an omega 6 acid, an omega 9 acid, and combinations thereof, and/or (f) a phytonutrient, preferably wherein the phytonutrient is selected from a sterol, carotene, an aliphatic alcohol, a mineral, and combinations thereof.

In a preferred embodiment, a method for treating estrogen sensitive cancer comprising: administering to a patient an effective amount of a composition comprising a *cannabis* extract (CE) in an estrogen positive environment.

In a further embodiment, the method wherein the CE comprises between 50% and 99.9% by weight cannabidiol (CBD).

In a further embodiment, the method wherein the CE is selected from the group consisting of: a full spectrum hemp extract (FSHE), a broad spectrum hemp extract (BSHE), a CBD isolate, and a cannabidiolic acid (CBDA) isolate.

In a further embodiment, the method wherein the CE is administered via an oral form, oral mucosal form, intravaginal form, nasal mucosal form, rectal form, injectable form, or combinations thereof.

In a further embodiment, the method wherein the effective amount of the *cannabis* extract comprising CBD comprises between 10 mg and 4,250 mg of CBD per day.

In a further embodiment, the method wherein administration of the CE is a dose given at least once a day, at least twice a day, or at least three times a day.

In a further embodiment, the method wherein the estrogen mediated cancer is a grade 1, grade 2, or grade 3 cancer.

In a further embodiment, the method wherein the estrogen mediated cancer is a chemoresistant estrogen mediated cancer.

In a further embodiment, the method wherein the CE comprises CBDA at a concentration of between 0.1% and 10%.

In a further embodiment, the method wherein the CE is a BSHE or FSHE and wherein each of the BSHE or FSHE comprises 50% to 99% by weight of CBD and at least one other cannabinoid at a concentration of 0.1% to 10% wherein the at least one other cannabinoid is selected from the group consisting of: $\Delta^9$-THC, THCA, THCV, $\Delta^8$-THC, CBC, CBCA, CBG, CBGA, CBDA, CBDV, CBN, CBL, and combinations thereof.

In a further embodiment, the method wherein the CE comprises CBD at a concentration of between 60% and 99%, and at least one other cannabinoid at a concentration of 0.1% to 10% wherein the at least one other cannabinoid is selected from the group consisting of: $\Delta^9$-THC, THCA, THCV, $\Delta^8$-THC, CBC, CBCA, CBG, CBGA, CBDA, CBDV, CBN, CBL, and combinations thereof, and wherein the CE comprises a total concentration of cannabinoids of between 65% and 99%.

In a further embodiment, the method wherein the composition comprises at least one additional compound selected from the group consisting of: a terpene, a polyphenol, an essential fatty acid, a phytonutrient, and combinations thereof, and wherein the at least one additional compound makes up between 0.1% and 50% of the total weight of the composition.

In a further embodiment, the method wherein the composition comprises an oil or a fat as a carrier.

In a further embodiment, the method wherein the effective amount of the composition is an amount sufficient to reach an effective therapeutic level of CBD as measured through systemic plasma levels.

In a further embodiment, the method wherein the composition is administered at an acidic pH. In a further embodiment, the method wherein the acidic pH is between 3.5 and 6.

In a preferred embodiment, a method of treatment of estrogen mediated cancer comprising administering to a patient an effective amount of a chemotherapeutic agent and coadministering an effective amount of a *cannabis* extract (CE).

In a further embodiment, the method wherein the chemotherapeutic agent and the CE are administered as one composition or as two different compositions.

In a further embodiment, the method wherein the chemotherapeutic agent is selected from the group consisting of: paclitaxel, carboplatin, doxorubicin, cisplatin, docetaxel, fluorouracil, methotrexate, cetuximab, and combinations thereof.

In a further embodiment, the method wherein the composition comprising the CE is a composition for oral, rectal, intravaginal, oromucosal, or nasal delivery.

In a further embodiment, the method wherein the effective amount of the composition is sufficient to reach an effective therapeutic level as measured through systemic plasma levels of CBD.

In a further embodiment, the method wherein the estrogen mediated cancer is a chemoresistant cancer.

In a further embodiment, the method wherein the effective amount of a chemotherapeutic agent is at least 50% less than an indicated individual dose and wherein the CE is administered at between 20 mg and 4,250 mg per day.

In a further embodiment, the method wherein the *cannabis* extract is administered in a composition at an acidic pH. In a further embodiment, the method wherein the acidic pH is between 3.5 and 6.

In a further embodiment, the method comprising a first step of determining chemoresistance of a cancerous tissue from said patient and administering to the patient an effective amount of the CE upon confirmation of chemoresistance.

In a further embodiment, the method wherein the CE comprises a cannabinoid selected from the group consisting of $\Delta^9$-THC, THCA, THCV, $\Delta^8$-THC, CBC, CBCA, CBG, CBGA, CBDA, CBDV, CBN, CBL, and combinations thereof.

In a further embodiment, the method further comprising at least one terpene. In a further embodiment, the method wherein the terpene is selected from the group consisting of β-myrcene, β-caryophyllene, linalool, α-pinene, citral, D-limonene, eucalyptol, and combinations thereof.

The method further comprising at least one polyphenol.

In a further embodiment, the method further comprising an essential fatty acid selected from the group consisting of an omega 3, an omega 6, an omega 9, and combinations thereof.

In a further embodiment, the method further comprising a phytonutrient. In a further embodiment, the method wherein the phytonutrient is selected from the group consisting of a sterol, carotene, an aliphatic alcohol, a mineral, and combinations thereof.

In a further embodiment, the method wherein the CBD is derived from a phytocannabinoid derived from a *cannabis* extract.

In a preferred embodiment, a method of treating estrogen mediated cancer comprising: (a) taking a cancerous cell from a patient and forming an organoid from the cancerous cell; (b) performing a screen on the organoid to determine a chemotherapeutic drug capable of reducing the percent of viable organoids by 50% with an IC50 dose of the chemotherapeutic drug; and (c) administering to the patient the chemotherapeutic drug with an effective amount of a composition comprising a *cannabis* extract (CE) having between 50% and 99.9% CBD, and concurrently administering an exogenous estrogen between 0.5 mg and 25 mg.

In a preferred embodiment, a method of treating estrogen mediated cancer comprising: (a) taking a squamous cell from the head, neck, face, or nose from a patient and forming at least one organoid from the squamous cell; (b) performing a screen on the at least one organoid to determine a chemotherapeutic drug responsive to the patient's organoid; and (c) administering to the patient the chemotherapeutic drug with an effective amount of a composition comprising a *cannabis* extract (CE) having between 50% and 99.9% CBD.

In a further embodiment, the method wherein the CE is administered to the patient as an oral form, oromucosal form, nasal form, rectal form, intravaginal form, injectable form, or combinations thereof. In a further embodiment, the method wherein the CE is administered oromucosally and intravaginally.

In a preferred embodiment, a composition for use in a method of treating estrogen mediated cancer wherein the composition comprises between 1% and 99% by weight of a *cannabis* extract (CE), and an exogenous estrogen source, sufficient to raise estrogen in a patient above premenopausal levels.

In a preferred embodiment, a method of treating estrogen sensitive cancer, comprising administering to an estrogen positive subject an effective amount of a *cannabis* extract (CE) comprising from about 50% to about 99.9% by weight of cannabidiol (CBD) and concurrently administering to said patient an effective amount of an exogenous estrogen.

BRIEF DESCRIPTION OF THE FIGURES

FIGS. 1A, 1B, 1C, 1D, 1E, 1F detail the effect of CE on grade 1 endometrial cancer organoids. FIGS. 1A-1D plot endometrial organoid response (e.g., % of viable treated organoids to untreated viable organoids) to increased concentrations of Broad Spectrum Hemp Extract, CBD isolate, Full Spectrum Hemp Extract, and CBDA, respectively for patient 1 (P1) and patient 2 (P2). FIGS. 1E and 1F show the same for P1 and P2, respectively.

FIGS. 2A-2D plot endometrial organoid response to increased concentrations of Broad Spectrum Hemp Extract (BSHE), CBD isolate, Full Spectrum Hemp Extract (FSHE), and CBDA, respectively for patient 4 (P4), patient 5 (P5), patient 7 (P7), and patient 9 (P9). FIGS. 2E-2H show the same for P4, P5, P7, and P9.

FIGS. 3A-3D plot endometrial organoid response to increased concentrations of Broad Spectrum Hemp Extract (BSHE), CBD isolate, Full Spectrum Hemp Extract (FSHE), and CBDA, respectively for patient 11 (P11) and patient 12 (P12), respectively. FIGS. 3E and 3F show the same for P11 and P12.

FIG. 5C details the effects of estrogen on PEO1 ovarian cancer cell viability alone and in the presence of 100 nM and 400 nM estrogen respectively.

FIGS. 6A through 6E depict endometrial cancer cells being treated with a *cannabis* extract comprising CBD, with FIG. 6A showing a diagram of the process of capturing the data regarding protein expression, FIG. 6B depicting protein differentiation numbers; FIG. 6C depicting upregulated and down regulated cells in the vehicle and with a CE treatment; FIG. 6D depicting the top 20 up and down regulated proteins in ECC treated cells; and FIG. 6E depicting the *cannabis* extract's effects on signaling and trafficking of various physiological and pathophysiological pathways.

FIG. 7A is heatmap generated using Perseus software comparing proteins that were either up or down regulated in the presence of respective CE compared to the same organoids that were untreated; FIGS. 7B through 7 E show the top 10 upregulated pathways per BSHE, FSHE, CBD isolate, and CBDA, respectively; FIG. 7F is another heatmap the differences in estrogen regulated protein expression per CE treatment compared to a vehicle control.

FIGS. 8A through 8D depict combined therapy treatment on patient derived endometrial cancer organoids and patient derived endometrial cancer xenografts; FIGS. 8A and 8B depict a grade 2 organoids treated paclitaxel and carboplatin, respectively; each chemotherapy agent was administered alone or with an IC50 dose of CE; FIG. 8C depicts grade 3 endometrial cancer organoids treated with paclitaxel and IC50 doses of CE; and FIG. 8D depicts tumor volume data for mice administered paclitaxel and a *cannabis* extract; each of FIG. 8A through 8D depicts the synergy related to the combined impact of chemotherapy being combined with the *cannabis* extract.

DETAILED DESCRIPTION OF THE INVENTION

Figure 1A:
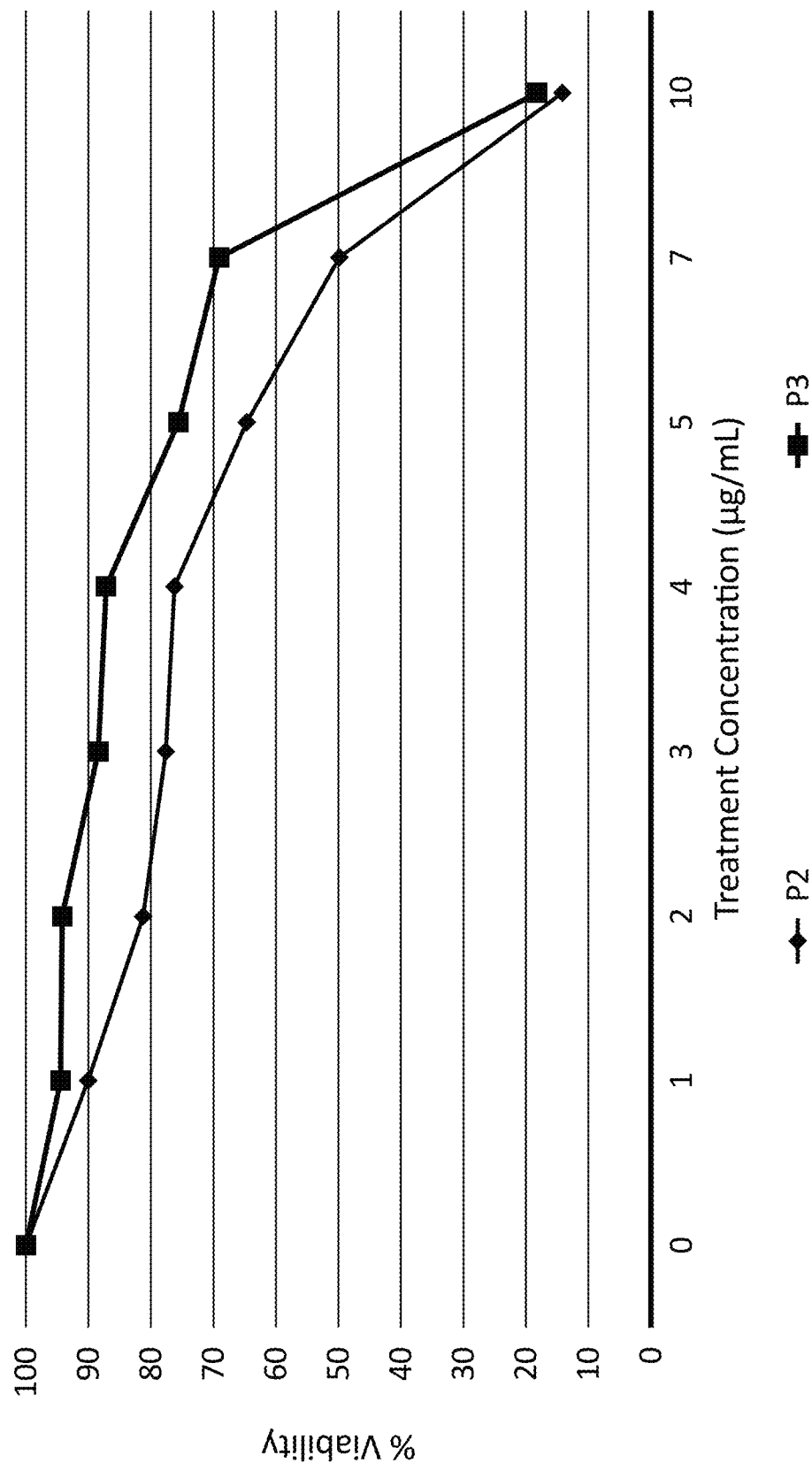
Figure 1B:
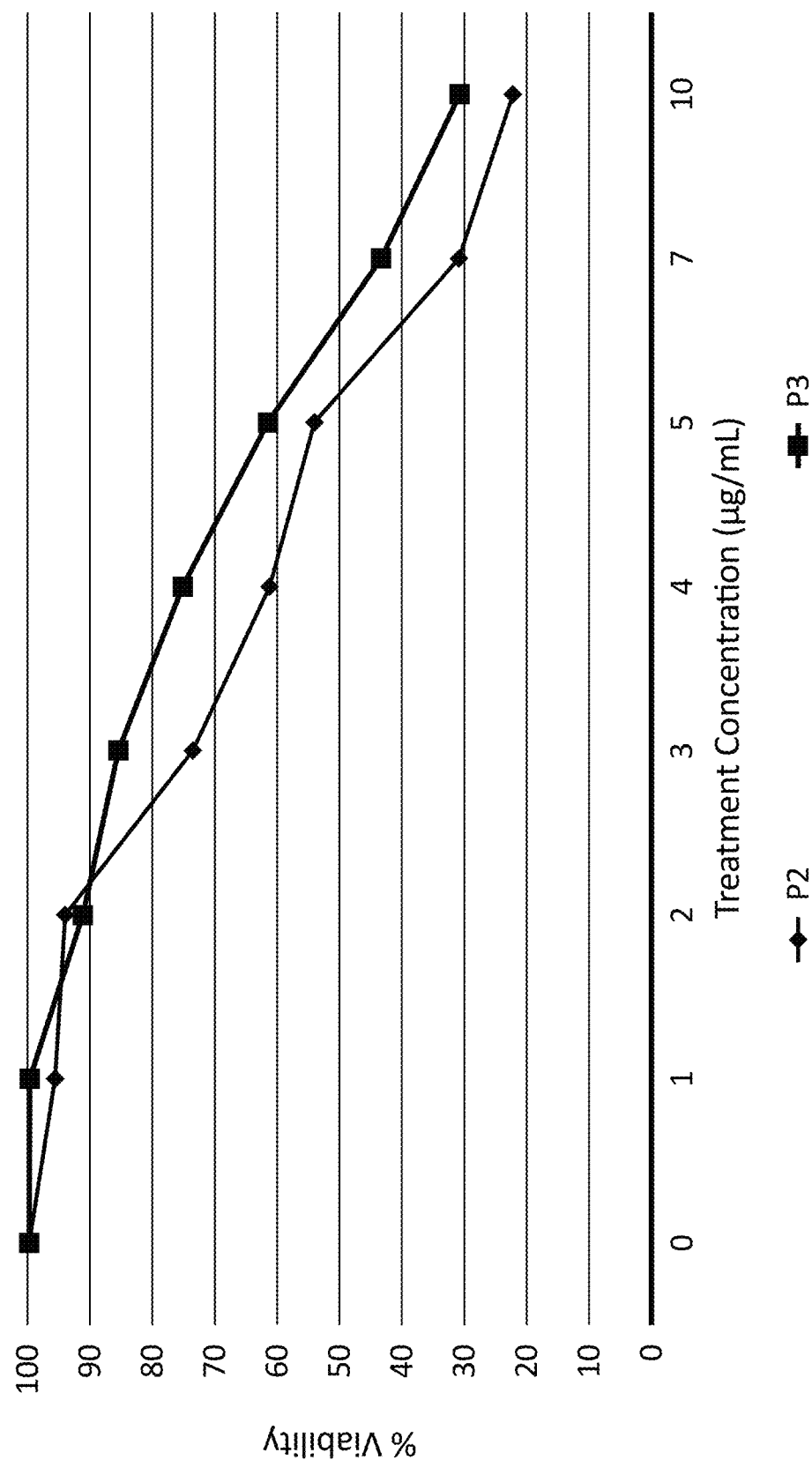

As used herein, the term "about" means plus or minus 5% of the numerical value of the number with which it is being used. Therefore, about 50% means in the range of 47.5%-52.5%, or where an integer is about 100, it would mean 95-105.

"Administering" when used in conjunction with a therapeutic means to administer a therapeutic directly to a subject, whereby the agent positively impacts the target. "Administering" the therapeutic drug or compound may be accomplished by, for example, injection, oral administration, topical administration, mucosal administration and/or in combination with other known techniques. The administering techniques may further include heating, radiation, chemotherapy, ultrasound, and the use of delivery agents. Preferably in the present disclosure the administration is through oral, oral mucosal/sublingual, injectable including but not limited to intravenous and intramuscular, nasal mucosa, rectal, and/or intravaginal dosage forms. Such intravaginal forms are intended to be inserted into the vagina, typically with a carrier, wherein the active ingredients pass through the vaginal mucosal membrane. The active ingredients may also be provided in an oral form, to be swallowed. Another oral form is an oral mucosal application, which is often provided as a sublingual application, which, while it is ultimately swallowed to enter the stomach, is intended to be held in the mouth, for example under the tongue, and the active ingredients at least partially pass through the oral mucosal membrane before being swallowed or passed into the stomach by salivary action or active swallowing of the materials or both. When inserted into the nasal mucosa, the material is simply inserted or administered into the nasal passages to allow the therapeutic agents to permeate the nasal mucosa. When provided intramuscularly, the therapeutic is injected into a muscle, or surrounding tissues.

By "pharmaceutically acceptable," it is meant that the components including, but not limited to the carrier, diluent, adjuvant, or excipient must be compatible with the other ingredients of the formulation and not deleterious to the recipient thereof.

As used here, the term "composition" is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s) and the inert ingredient(s) that make up the carrier, as well as any product which results, directly or indirectly, from combination, complexation, or aggregation of any two or more of the ingredients or from dissociation of one or more of the ingredients, or from other types of reactions or interactions of one or more of the ingredients. Accordingly, the pharmaceutical compositions of the present invention encompass any composition made by admixing a compound or compounds of the present invention and a pharmaceutically acceptable carrier.

As used herein, the terms "agent," "active agent," "therapeutic agent," or "therapeutic" mean a compound or composition utilized to treat, combat, ameliorate, prevent, or improve an unwanted condition or disease of a patient. Furthermore, the terms "agent," "active agent," "therapeutic agent," or "therapeutic" encompass a *cannabis* extract and/or additional agents as described in the present disclosure.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue to achieve the therapeutic response. Specifically, the therapeutic shall be effective in treating cancerous growths related to estrogen sensitive diseases.

The terms "treat," "treated," or "treating" as used herein refer to both therapeutic treatment and prophylactic or preventative measures wherein the object is to prevent or slow down (lessen) an undesired physiological condition, disorder, or disease, or to obtain beneficial or desired clinical results. For the purposes of this disclosure, beneficial or desired results include, but are not limited to, alleviation of symptoms; diminishment of the extent of the condition, disorder, or disease such as a reduction in the size of a tumor; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease.

As used here, the term "*cannabis* extract" (CE) is a composition derived from the *Cannabis* genus of plants (including hemp). A *cannabis* extract contains cannabinoids with the primary cannabinoid by weight being cannabidiol (CBD). In embodiments a CE may comprise, by weight, between about 1 and 100% CBD (being a refined CBD isolate), preferably between about 20 and 99.9% CBD, more preferably between about 50 and 99.9% CBD, even more preferably between about 70 and 99.9% CBD, and most preferably between about 90 and 99.9% CBD. Synthetically derived CBD may make up all or a part of the percentage of CBD within a *cannabis* extract. In addition to CBD, embodiments of CE may include at least one additional cannabinoid, typically selected from the group consisting of Δ9-THC, THCA, THCV, Δ8-THC, CBC, CBCA, CBG, CBGA, CBDA, CBDV, CBN, CBL, and combinations thereof. When present in a CE, the at least one additional cannabinoid, and combinations thereof, comprise by weight between about 0.1 and 40% of the CE. Full spectrum hemp extract, broad spectrum hemp extract, CBD isolate, and CBDA isolate are forms of CE utilized herein, as nonlimiting examples of the CE. Throughout the application, the term CBD is often used interchangeably with CE, to mean the CE product containing the particular amount of CBD. In other instances, which are obvious to the reader, the term "CBD" refers to a CBD isolate, which means the CE was processed to separate CBD from virtually all other components of the CE.

As used herein, the term full spectrum hemp extract (FSHE) is a composition derived from the *Cannabis* genus of plants which contains CBD, and quantities of THC, by weight, above 0, preferably, between 0.01 and 5%, most preferably being between 0.01% and 0.3%. The FSHE may comprise additional cannabinoids, yielding a product that comprises, by weight, at least 50-99.9% CBD, at least 0.01 to 10% THC ($\Delta^9$-THC, THCA, THCV, $\Delta^8$-THC), and total cannabinoids of between 50% and 99.9% of the weight of the CE.

As used herein, the term broad spectrum hemp extract (BSHE) is a composition derived from the *Cannabis* genus of plants which has undergone at least some purification in order to refine the extract. Typically, a BSHE comprises, by weight, between 60 and 99.9% CBD and least one additional cannabinoid, selected from the group consisting of $\Delta^9$-THC, THCA, THCV, $\Delta^8$-THC, CBC, CBCA, CBG, CBGA, CBDA, CBDV, CBN, CBL, and combinations thereof at between 0.1 and 40% by weight of the CE.

As used herein, the term "synthetic CBD" means a cannabidiol that is manufactured in a laboratory.

As used herein the terms "estrogen" and "estrogens" refer to all forms of estrogen or estrogen-like molecules including, without limitation, endogenous estrogens (e.g., estrone, 17β-estradiol, estriol, estetrol, estradiol), phytoestrogens/biosynthetic estrogens (e.g., genistein, zearalenone), and other exogenous estrogens whether or not biosynthetic or synthetic estrogens or stimulatory estrogen receptor ligands (e.g., ethinylestradiol, estradiol valerate, 17β-estradiol, mestranol, estropipate, tamoxifen, etc.)

As used herein, the term "estrogen sensitive" means the physiology and/or pathophysiology of cells, tissues, organs, organ systems, organoids, etc. is stimulated, increased, caused, induced, activated, catalyzed, invoked, etc. by estrogen or in the presence of estrogen. As one nonlimiting example, estrogen-sensitive cancer are cancers that grow, proliferate, show increased cell viability, etc. in the presence of estrogen regardless of whether the cancer has been identified as estrogen receptor positive (ER+) or not.

As used herein the term "estrogen receptor positive" means cells, tissues, or both that have been identified as expressing one or more estrogen receptor types (e.g., ERα, ERβ, G-protein coupled ER), ER receptor type variant, ER receptor type mutation, or combinations thereof.

As used herein, the term "estrogen inhibited" means the physiology and/or pathophysiology of cells, tissues, organs, organ systems, organoids, etc. is decreased, suppressed, restricted, impeded, etc. in the presence of estrogen.

As used herein the term "estrogen positive" refers to a mammalian subject or patient that is actively producing one or more endogenous estrogens, is actively being treated/supplemented with one or more exogenous estrogens, or both, and is not actively lessening amounts of estrogens to a level below an effective amount by use of an estrogen receptor antagonist, selective estrogen receptor mediator (SERM), progesterone or progestogen, aromatase inhibitor, or other anti-estrogen therapeutic.

As used herein the term "effective amount of estrogen" or similar term refers to the amount of estrogen (endogenous, exogenous, or both together) that works with CE to synergistically inhibit growth, proliferation, metabolic activity, and/or viability of susceptible cancer cells; to synergistically improve cancer cell death such as by apoptosis; or both, regardless of the mechanism of action from which the synergistic effects come about. Effective amounts of estrogen may be achieved with amounts of estrogen produced by and/or provided to the human body such as greater than or equal to 30 pg/ml, 300 pg/ml, 500 pg/ml, 20,000 pg/ml or even 100,000 pg/ml; or greater than or equal to 250 pmol/liter, 1000 pmole/liter 17,000 pmol/liter. Effective amounts of estrogen may also be achieved by treating a patient with doses of exogenous estrogen from about 0.025 mg to about 25 mg at least once a day and up to about 4 times per day. In preferred embodiments, the effective amount of estrogen is greater than or equal to the levels of endogenous estrogen in a healthy pre-menopausal woman.

In our previous work, we showed that *cannabis* extracts (CEs) decrease organoid cell viability for endometrial cancer, ovarian cancer, endometriosis, and head and neck cancers. We also showed that CEs in combination with a chemotherapeutic agent synergistically decrease organoid cell viability in endometrial cancer and ovarian cancer. When mice were infected with patient-derived endometrial cancer cells to create patient-derived xenografts (PDX), we showed that treatment with various CE compositions, alone and together with a chemotherapeutic agent, reversed tumor volume such that after 21 days, tumor volume was significantly reduced as compared to the starting tumor volume.

We began this research due to a dual interest in the endocannabinoid system (ECS) and women's health. The ECS makes cannabinoids (endocannabinoids) inside the body; the endocannabinoids foster cellular balance throughout nearly every biological system in the body, including the reproductive system. The ECS is comprised of three main parts: (i) cannabinoid receptors (CB1 and CB2); (ii) endocannabinoids (most notably anandamide and 2-Arachidonoylglycerol [2-AG]); and (iii) enzymes that synthesize endocannabinoids or break down endocannabinoids such as fatty acid amino hydrolase (FAAH) and monoacetylglycerol lipase (MAGL).

Generally, cannabinoid receptors, found on the surface of cells, "listen" to the environment around each cell via chemicals (e.g., cannabinoids) that interact with the receptors/ECS. These receptors can transmit information relating to current external conditions to cell interiors to jump-start the proper cellular response. Properly functioning cannabinoid receptors have the crucial function of creating homeostasis in the body's cells. Cannabinoid receptors belong to a superfamily of G protein-coupled receptors. They are single polypeptides with seven transmembrane α-helices, and have an extracellular, glycosylated N-terminus and intracellular C-terminus. Both CB1 and CB2 cannabinoid receptors are linked to G1/0 proteins.

Endocannabinoid receptors are abundant in female reproductive organs and the central nervous system. Their signaling and trafficking influence multiple physiological and pathophysiological functions of female reproduction, including folliculogenesis, oocyte maturation, cytoskeleton rearrangement, endometrial cell motility, endometrial migration & proliferation, decidualization, plasticity, and peripheral innervation. Thus, cannabinoids exert antiproliferative effects on deep infiltrating endometriosis, and increased cannabinoid signaling may reduce proliferation of endometriotic lesions, the etiology of which shares some genetic basis and pathophysiological overlap with ovarian and endometrial cancers. Cannabinoid receptors in the pelvis, ovaries, endometrium, vulva, and the central and peripheral nervous systems influence inflammation, nociception, and arousal in these therapeutic targets. Cannabinoids trigger localized vasodilation and relaxation of pathological smooth muscle contraction and/or spasticity.

Endocannabinoids can be created from precursors in lipid membranes and released therefrom when needed. Generally, 2-AG has a higher efficacy than anandamide with respect to both CB1 and CB2 receptors. Although the effects of endocannabinoids are primarily mediated via CB1 and CB2 receptors, endocannabinoid effects may be mediated by other receptors, channels, and the like. Although cannabinoid receptors are present in almost every organ and organ system throughout the body (e.g., reproductive system, heart, lungs, brain, blood vessels, GI tract, liver, stomach, etc.), CB1 receptors are abundant in the brain and central nervous system, whereas CB2 receptors are sparse in the central nervous system but are common throughout the periphery, primarily on immune cells.

In addition to endocannabinoids, there are phytocannabinoids and synthetic cannabinoids. Phytocannabinoids are cannabinoids produced by plants. Plants that produce cannabinoids include, but are not limited to: kava, rosemary, liverwort, electric daisy, *echinacea*, cacao, helichrysum, pepper trees, black truffles, *cannabis*, as well as a strain of yeast (*Pichia pastoris*). *Cannabis* plants concentrate phytocannabinoids in a viscous resin produced in glandular structures known as trichomes. The cannabinoid resin is also rich in terpenes, which are largely responsible for the odor of the plants in the *cannabis* family. Cannabinoids, terpenes, and other phytochemicals are also present in additional plant tissues. Uptake of phytocannabinoids within the body is confounded by lipophilic properties. Phytocannabinoids are nearly insoluble in water but are soluble in lipids, alcohol, and nonpolar organic solvents, and can also be suspended in emulsions. Synthetic cannabinoids are not created by plants or animals but are chemically synthesized such as in a lab.

*Cannabis* extracts have only recently begun detailed study into therapeutic effects for treatment of disease. Two molecules typically found in *cannabis* extracts of highest interest are typically cannabidiol (CBD) and Δ-9 tetrahydrocannabidiol (THC). Another name for certain *cannabis* plants is hemp. Hemp is defined in the U.S. as a *cannabis* plant with a delta-9-THC content of 0.3% or less by dried weight, so it is a political definition and not a scientific definition. The byproducts of hemp plants, including cannabinoids, are federally legal as defined in section 7606 of the 2014 Farm Bill and made permanent in the 2018 Farm Bill. Just a few examples of different cannabinoids include Cannabigerol (CBG), Cannabichromene (CBC), cannabidivarin (CBDV), and Cannabinol (CBN).

Unlike THC, which exerts its action by binding to CB1 and CB2, CBD does not readily bind to these receptors and hence has no psychotropic activity. In fact most CBD mediated effects do not directly involve either CB receptor. Rather, CBD may act indirectly to stimulate endogenous cannabinoid signaling by suppressing FAAH, FAAH suppression reduces the breakdown of cannabinoids (e.g., endocannabinoids), which increases the availability of endogenous cannabinoids (i.e., anandamide) by prolonging the half-life. This is especially interesting as anandamide is partially responsible for regulating human reproduction, among its other implications within the body. There is also evidence that CBD stimulates the release of 2-AG, antagonizes and act as a partial allosteric modulator of CB1 receptors, and stimulates 5HT1A/2A/3A serotonin receptors, TRPV1-2 vanilloid receptors, and glycine channels. Therefore, the mechanisms of action for CBD are complex, varied, and still only partially understood.

With respect to inflammation and/or pain, CBD may play a modulatory role. For example, cytokines are signaling proteins synthesized and secreted by immune cells upon stimulation. Accordingly, one of the possible mechanisms of immune control by CBD is by perturbing the balance between cytokines produced by T helper subsets, $T_h1$ and $T_h2$. In certain prior studies, both anti-inflammatory and proinflammatory effects were shown. Suppressing IL-6, a specific cytokine, can decrease tissue injury, which may occur during chronic inflammation. Cannabinoids, including CBD and THC have been shown to decrease IL-6, TNFα, GM-CSF, and IFNγ, all of which are types of cytokines. Accordingly, one or more of CBD or THC may be a necessary component in certain applications when a combined effect is necessary to reduce inflammation and decrease pain. Low doses of THC may be suitable to provide these therapeutic effects in combination with CBD. CBD is also known to stimulate vanilloid pain receptors (TRPV-1 receptor), which are known to mediate pain perception, inflammation, and body temperature. CBD may also impact certain adenosine receptors, which play a significant role in cardiovascular function and broadly impact anti-inflammatory effects throughout the body as well as regulate and decrease anxiety and depression and increase the sense of well-being.

*Cannabis* extracts can be derived from one or more *cannabis* plant strains as a source material, or synthetically derived. Notably, while different strains may produce green material with different proportions of desirable compounds, different growing conditions can impact the precise amounts of each compound even for the same strains. *Cannabis* extracts may include isolates of certain compounds, such as isolated CBD, or may include products that contain a wider variety of cannabinoids and other materials, such as those called a Full spectrum hemp extract (FSHE) and Broad spectrum hemp extract (BSHE), each of which may contain an array of cannabinoids and other phytonutrients such as essential fatty acids, flavonoids, terpenes and essential vitamins and minerals. While different strains and growth conditions may yield green material that has different concentrations, certain extraction processes can be utilized to assist in forming extracts that have small variance between runs to provide overall stability to a final product.

The FSHE and BSHE for therapeutic use in the methods herein, are generated by an extraction process to remove desired materials from the trichomes and other green material from the hemp plant. Representative processes are detailed in U.S. application 2023/0131076 A1. The FSHE and BSHE utilized herein are extracted from *cannabis* strains having high concentrations of CBD, and the products being generated typically are evaluated based on a CBD content in mg. The *cannabis* extracts further, preferably, comprise certain amounts of array of cannabinoids and other phytonutrients such as essential fatty acids, flavonoids, terpenes and essential vitamins and minerals.

A representative, nonlimiting sample of the *cannabis* extract of the present disclosure comprises concentrations of certain compounds within the following ranges:

TABLE 1

CANNABINOID EXTRACT EXAMPLES

| Cannabinoid | BSHE | | FSHE | |
|---|---|---|---|---|
| | mg/g | % | mg/g | % |
| $\Delta^8$-THC | ND | 0-1 | ND | 0-3.0 |
| $\Delta^9$-THC | ND | 0-0.3 | 25 | 0.01-5.0 |
| $\Delta^9$-THCA | ND | 0-0.3 | ND | 0-1.0 |
| THCV | ND | ND | | ND |
| THCVA | ND | ND | | ND |
| CBD | 900 | 70-99 | 800 | 65-98 |
| CBDA | ND | 0-2.5 | | ND |
| CBC | ND | 0-3.5 | 19 | 0-0.35 |
| CBCA | ND | 0-5.0 | | ND |
| CBDV | ND | 0-2.5 | 8 | 0-2.5 |
| CBG | 15 | 0.1-3.5 | 17 | 0.1-3.5 |
| CBGA | ND | 0-3.5 | | ND |
| CBN | 2.0 | 0.01-0.5 | 1.65 | 0-0.5 |
| Total THC | ND | 0-1.5 | 25 | 0.3-5.0 |
| Total CBD | 900 | 70-99 | 800 | 65-98 |
| Total Cannabinoids | 917 | 71-99 | 870.65 | 65-99.9 |
| Sum of additional Cannabinoids | 0 | 0-10 | 0 | 0-10.0 |

The uterus has three primary layers, the outermost serosa, which coats the uterus, the myometrium, which is the muscle layer underneath the serosa, and the endometrium, which is the innermost layer, responsive to hormone fluctuations in a woman's body. The endometrium has two stratum; the stratum functionalis and the stratum basalis. Estrogen causes the endometrium to thicken, and progesterone causes the endometrium to become vascular and glandular. These are normal responses to hormones during a woman's reproductive years to ready a woman's body should an egg become fertilized. If not, the hormonally sensitive stratum funcionalis is shed, and the cycle begins again. Most, if not all of normal tissue response to hormones is via various receptors such as estrogen receptors and progesterone receptors. Unfortunately, certain gene mutations can result in abnormal, cancerous cells, some of which thrive in the presence of estrogens, especially unopposed estrogens, and may have altered estrogen/progesterone receptor profiles compared to normal, noncancerous cells.

Unopposed estrogen or estrogen dominance is associated with several diseases/disorders such as endometriosis, breast cancer, polycystic ovarian syndrome, insulin resistance, ovarian cancer, and uterine cancer/endometrial cancer. While unopposed estrogen may not cause these conditions, it may make them worse. Unopposed estrogen may stem from a variety of factors such as medications (e.g., contraceptives, hormone replacement therapy), obesity, stress, alcohol, liver problems, and xenoestrogens such as bisphenol A (BPA) and phthalates. Historically, type I endometrial cancer is linked to unopposed estrogen.

Endometrial cancer or endometrial carcinoma was historically divided into two types, Type I, which is linked to unopposed estrogen and Type II, which is not. Although estrogen sensitivity is relevant to distinguishing different types of endometrial cancers, there are other ways to categorize endometrial cancers, including molecular characterization, which are discussed below. First, however, it should be noted that endometrial cancer (EC) is one of the most frequently diagnosed gynecological cancers worldwide, and its prevalence has increased by more than 50% over the last two decades. Obesity may be a contributor to this rise as enzymes in adipose tissue help synthesize endogenous estrogens. Since the endometiurn includes glandular epithelial cells, endometrial cancers have been characterized by grade, each grade relating to how much the cancer is organized into glands that look like normal, healthy endometrium. In low-grade endometrial cancers (grades 1 and 2), more of the cancer cells are organized into normal-looking glands. In high-grade endometrial cancers (grade 3), more of the cancer cells are disorganized and do not form glands. Specifically, grade 1 tumors are defined as having 95% or more of the cancer tissue forming glands and grade 2 tumors are defined as having between 50% and 94% of the cancer tissue forming glands. Grades 1 and 2 endometrial cancers are typically estrogen sensitive, Type I cancers that proliferate in unopposed estrogen. Type I endometrial cancers, however, are not very aggressive, and do not spread quickly. Accordingly, endometrial cancers that fall into these two grades are typically deemed to be estrogen mediated diseases. Estrogen mediated EC have been treated with anti-estrogenic drugs, such as selective estrogen receptor modulators (SERM) or down regulators (SERD) and aromatase inhibitors and/or progestins such as progesterone. These drugs work to block the estrogen receptor through which estrogen effects are mediated or prevent the aromatase enzyme from biosynthesizing estradiol.

In contrast to the grades 1 and 2 EC, grade 3 tumors have less than half of the cancer tissue forming glands. Grade 3 cancers tend to be aggressive (they grow and spread fast) and have a worse outlook than lower-grade cancers. However, these cancers are typically not dependent on estrogen from their proliferative growth and tend to be estrogen receptor negative ER(−), and not estrogen mediated/sensitive. Since these endometrial cancers tend to be ER(−) there is no benefit from blocking estrogen receptors/inhibiting estrogen biosynthesis via aromatase.

Endometrial cancers may also be described histologically, based on how the cells look under the microscope. The most common type of endometrial cancer is adenocarcinoma, and most adenocarcinomas (about 75%) are endometrioid adenocarcinomas. These names are descriptive as "adeno" refers to glands and "carcinoma" relates to cancers arising in glandular epithelial cells. Endometrioid indicates that the cancerous epithelial cells arise from and/or look like the endometrium. It is not uncommon, however, for endornetrial adenocarcinomas to also include squamous cells (flat, thin cells) in addition to glandular cells. There are many variants (or sub-types) of endometrioid cancers including: Adenocarcinoma, (with squamous differentiation); Adenoacanthoma; Adenosquamous (or mixed cell); Secretory carcinoma; Ciliated carcinoma; Villoglandular adenocarcinoma. Grade 1 and grade 2 endometrioid cancers are typically type I, estrogen-sensitive endometrial cancers. If however, the endometrioid carcinoma is grade 3 it is more likely to fall into the type 2 category.

Other types of endometrial cancers include Uterine carcinosarcoma or CS; Squamous cell carcinoma; Small cell carcinoma; Transitional carcinoma; and Serous carcinoma. Clear-cell carcinoma, mucinous adenocarcinoma, undifferentiated carcinoma, dedifferentiated carcinoma, and serous adenocarcinoma are less common types of endometrial adenocarcinomas. They tend to grow and spread faster than most types of endometrial cancer. They often have spread outside the uterus by the time they'diagnosed. In addition to grade 3 endometrioid carcinoma, type 2 endometrial cancers include all endometrial carcinomas that are not type I such as papillary serous carcinoma, clear cell carcinoma, and undifferentiated carcinomas.

Interestingly, it is now believed that uterine carcinosarcoma (CS) starts in the endometrium having features of both endometrial carcinoma and sarcoma. Sarcoma refers to a cancer that starts in muscle cells such as the myometrium. In the past, CS was thought to be a uterine sarcoma and not a carcinoma, but it is now thought to be an endometrial carcinoma that is so abnormal it no longer looks much like the cells it came from (it's poorly differentiated). Uterine CS is a type 2 endometrial carcinoma. CS tumors are also known as malignant mixed mesodermal tumors or malignant mixed mullerian tumors (MMMTs). They make up about 3% of uterine cancers.

Due to technological advancements, endometrial cancers can also be characterized by molecular subgroup. There are four molecular subtypes, including copy number high (CNH) which have widespread genomic alterations and most being high grade endometrioid tumors; microsatellite instability (MSI), which are uniformly endometrioid having a high mutation burden with common mutations in PTEN, PIK3CA, and PIK3R1 and account for about 25-30% of tumors; hypermutated cases with POLE mutations, which account for about 7% of tumors, and low copy number (CNL), which do not have an increased mutational burden and uniformly include low grade endometrioid tumors. Some of these subtypes are treated with PD-1/PD-L1 inhibitors or other immune checkpoint inhibitors such as pembrolizumab or other inhibitors such as Lenvatinib. However, these molecules, like first line chemotherapy agents, have high toxicity profiles and thus have significant co-morbidities associated with their use. Furthermore, being targeted, they sometimes miss the heterogeneous nature of the cancer. And despite understanding of major signaling pathways driving the growth and metastasis of endometrial cancer, clinical trials targeting these signals have reported poor outcomes. Again, the heterogeneous nature of endometrial cancer is suspected to be one of the key reasons for the failure of targeted therapies.

In some cases, EC poses few, if any symptoms, and is one of the key reasons why many EC patients only discover the disease at later stages. However, for others some of the symptoms of EC are masked by normal reproductive cycle activity or symptoms of menopause. Accordingly, some women miss early signs of EC due to confounding factors. Some EC patients present with abnormal uterine bleeding, in which case, at least some patients may be diagnosed at an early stage. Once detected, treatment for EC is almost always surgical removal of the cancerous tissue, the entire organ, or the uterus, fallopian tubes, ovaries, and even the cervix. Thereafter patients may receive chemotherapy, and/ or radiation therapy. In some cases, early detection of EC may prevent the need for chemotherapy or radiation therapy, as the cancer is contained only in the uterus. However, EC is quite nefarious, and even a few missed cells, which have migrated from the uterus, then allow for proliferation of the diseased tissues, thus providing evidence for the need for chemotherapy even at early-stage diagnosis after removal of the organs.

The International Federation of Gynecology and Obstetrics (FIGO) uses a staging system for classifying endometrial carcinomas. Loosely, Stage I and Stage II tumors are confined to the uterus and do not extend therebeyond. Stage III tumors have spread locally or regionally, and Stage IV tumors have invaded the bladder or bowel mucosa and or have distant metastasis. For both early stage (Stage I and II EC), and for Stages III and IV EC, first line treatment for EC almost always includes hysterectomy and bilateral salpingo-oophorectomy. In most cases, this is followed by chemotherapy. In view of the significant side effects of chemotherapy, a small portion of stage I and II patients may omit or reduce chemotherapy use as compared to Stages III and IV patients. Chemotherapy is virtually always given to stage III or stage IV EC patients, and often with several rounds of therapy, with the goal of optimizing the risks and the rewards. For Stage III and IV EC, accordingly, organ and tumor removal are typically followed by chemotherapy treatment to capture metastatic disease, as the endometrial cancer cells have often already migrated from the uterus. However, it is well-known that chemotherapy agents are somewhat indiscriminate in their killing, and thus significant secondary impacts occur to the patient leading to diminished quality of life. Indeed, even where the chemotherapy is effective in treating the cancer, the toxic effects of the chemotherapy often prove fatal over time. In virtually all cases, chemotherapy is given in a cycle, meaning a drug or combination of drugs are given for a period of usually 2-6 weeks, and then a rest period, followed by a second or more treatment period. Drugs that are currently utilized for endometrial cancer treatment include but are not limited to: paclitaxel, carboplatin, doxorubicin, cisplatin, docetaxel, and the combined therapy of carboplatin or cisplatin with paclitaxel, and other agents such as, without limitation altretamine, cyclophosphamide, etoposide, gemcitabine, ifosfamide, itinoteca, melphalan, pemetrexed, topotecan, binorelbin, and combinations of these and other agents.

Chemotherapy drugs typically fall into different classes such as alkylating agents, antimetabolites, ant-tumor antibiotics, topoisomerase inhibitors, mitotic inhibitors, DNA repair enzyme inhibitors, plant alkaloids, and antineoplastics. The most common chemotherapy drugs for EC, fall into the following classes as follows: Paclitaxel is an antineoplastic—plant alkaloid; Docetaxel is an antineoplastic—plant alkaloid; Doxorubicin is an antineoplastic—anthracycline antibiotic; Carboplatin is an antineoplastic—alkylating agent and platinum based; and Cisplatin is an antineoplastic—alkylating agent and platinum based. Frequently, paclitaxel is given in combination with one or more of cisplatin or carboplatin. However, while over 60% of EC patients initially respond to platinum-based chemotherapy, the majority relapse, and the term "platinum-resistant" refers to patients with EC that progress within six-months of platinum-based therapy. These patients are at the highest risk for disease related mortality. Even with aggressive treatment and especially when not detected until stage III or IV cancer, EC often metastasizes, leading to low survival rates at 2 and 5 years past initial diagnosis and treatment. Because of the risks associated with chemotherapy, including the toxicity to healthy cells as well as the presence of chemoresistant EC, there is a significant need for new therapeutic treatments including ways to reduce or replace chemotherapy.

Chemoresistance is defined as simply that the cancer cells are resistant to the action of the particular therapeutic agent, such that the disease progresses. Chemoresistant disease may still have some clinical response, but not at sufficient levels to prevent disease progression, or would require such high doses to make the treatment unsuitable. Chemosensitive, therefore being the opposite, wherein the cancer cells in a patient are sensitive to the chemotherapy agent, so that the disease is managed or reduced. However, EC may be, at one point chemosensitive and become chemoresistant as treatment progresses through a typical on/off cycle for chemotherapy.

Indeed, presently, where chemoresistant tumors exist, there are few, if any treatment plans other than palliative care, or additional removal upon the identification of tumors. This later step becomes nearly impossible when tumors metastasize. However, for each of chemonaive (tumors who have not been contacted with chemotherapy), chemosensitive tumors (those which respond to chemotherapy), and chemoresistant tumors (those which are poorly responsive to chemotherapy—wherein the side effects at necessary doses outweighs the treatment), CEs may be a superior treatment for EC, or used as an adjunct or in combination therapies.

Other types of estrogen mediated/sensitive cancers are also known. These include, but are not limited to certain ovarian cancers, colorectal cancers, breast cancers, and others. Estrogen sensitive cancers are frequently treated with chemotherapy and estrogen blockers or inhibitors, so as to limit the growth of the cancer. Applicant, however, has surprisingly identified that a new treatment protocol, one that completely changes the standard of care, may be more effective as a therapeutic treatment for estrogen sensitive cancers such as certain endometrial cancers.

In our previous work we were able to show a dramatic reduction in the average number of endometrial cancer organoids as compared to the vehicle using CE concentrations as low as 2 μg/ml. Therefore, administering CE effectively decreases patient-derived endometrial cancer organoid viability compared to no treatment at all. These organoids, however, were grown in a media that included a small amount of estrogen (2 nM), which is a standard amount we use to grow endometrial cancer organoids.

Generally, growth of grade 1 and grade 2 endometrial cancers, which are typically categorized as type 1 endometrial cancers, is stimulated by unopposed/excess estrogen, and hence are considered to be estrogen sensitive. Most grade 1 and grade 2 endometrial cancers express estrogen receptors, and thus are ER+. In contrast, growth of grade 3 endometrial cancers is not typically stimulated by unopposed/excess estrogen, do not typically express estrogen receptors and as such are not ER+, and are not estrogen sensitive. To better understand the effects of CE on excess/unopposed estrogen on various grades of endometrial cancer organoids, we first determined the efficacy of various CE on grade 1, grade 2, and grade 3 patient derived endometrial cancer organoids grown in our standard growth medium. Specifically, we determined the efficacy of broad spectrum hemp extract (BSHE), full spectrum hemp extract (FSHE), CBD isolate, and CBDA on all three grades of endometrial cancer organoids.

For this set of experiments, tissue samples were obtained from a different set of 12 patients than were used for our initial experiments. Cells from these patients were prepared as described in the Methods section below. Generally, organoids were prepared from patient donors to test the efficacy of BSHE (FIG. 1A), CBD isolate (FIG. 1), and FSHE (FIG. 1C), at 1, 2, 3, 4, 5, 7, and 10 μg/mL, and CBDA (FIG. 1D) at 1, 5, 10, 15, 20, 25, 35, and 50 μg/mL on grade 1 endometrial cancer organoids. CBDA was tested at higher concentrations due to a general lack of sensitivity at lower doses. In these experiments, endometrial cancer organoids were tested in a low estrogen environment provided by the estrogen in the growth media.

Referring to FIG. 1A through 1D, two sets of organoids prepared from grade 1 endometrial cancer tumors (P2 and P3) of unspecified type were established and treated with BSHE, CBD isolate, FSHE, and CBDA respectively. In these graphs, dosages (g/ml) are plotted against a % viability. Generally, % viability is an average across one or more sets of organoids (n=3 or n=4 per set) compared to the average of the one or more sets of untreated organoids (i.e., vehicle) and expressed as % change therefrom. Thus, untreated organoids are set at 100%. All organoid data herein is expressed as a % viability.

Each CE was able to decrease the viability of grade 1 endometrial cancer organoids from both donating patents in a dose dependent manner. Organoids from P2 were more sensitive to BSHE, FSHE, and CBD isolate, whereas organoids from P3 seem to be somewhat more sensitive to CBDA than P2. As shown in FIG. 1 1D, however, 50% viability on the graph is about the same for both sets of organoids when treated with CBDA. In contrast, organoids from P2 show 50% viability (in the graphs) at lower BSHE, FSHE, and CBD isolate concentrations than those from P3.

Figure 1C:
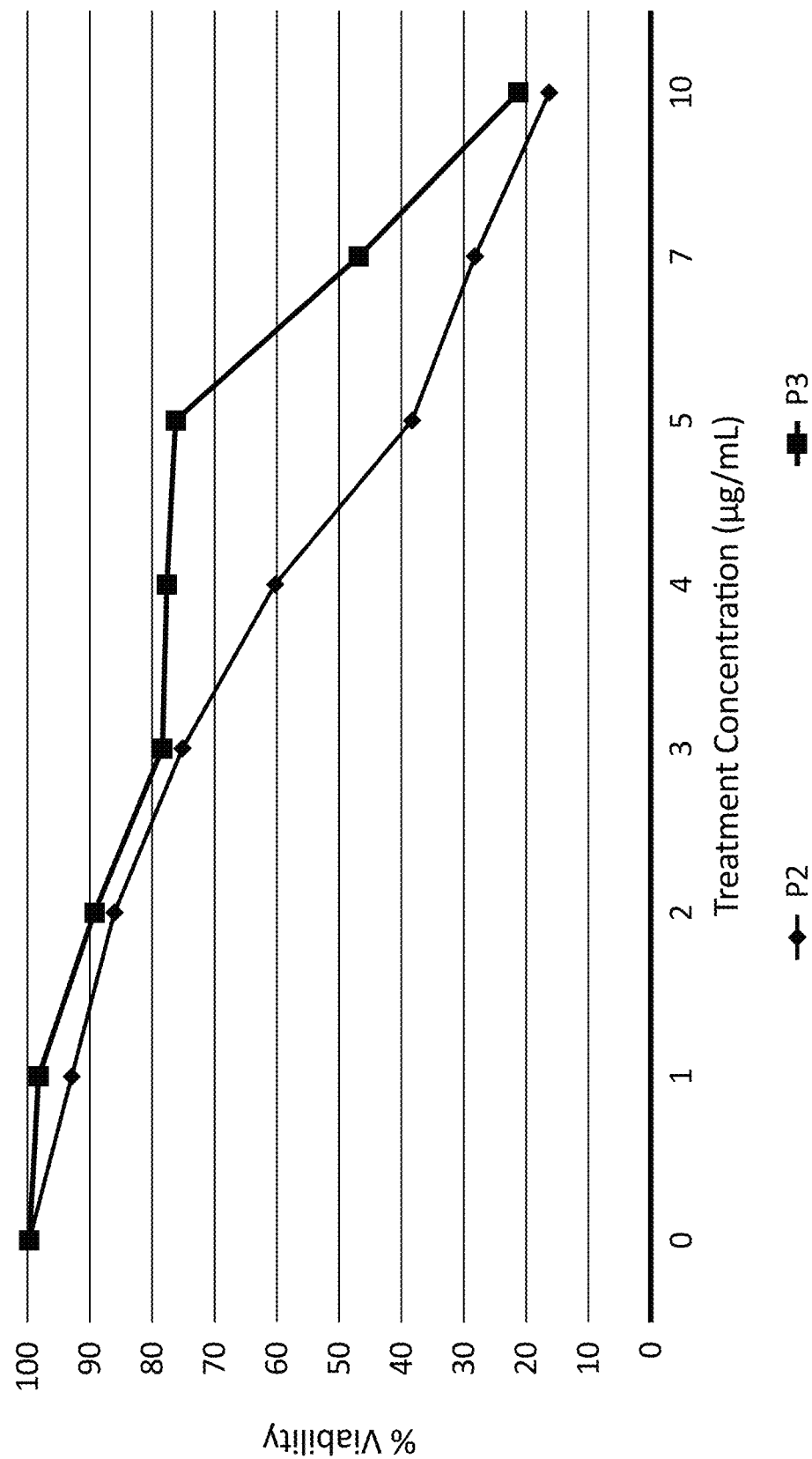
Figure 1D:
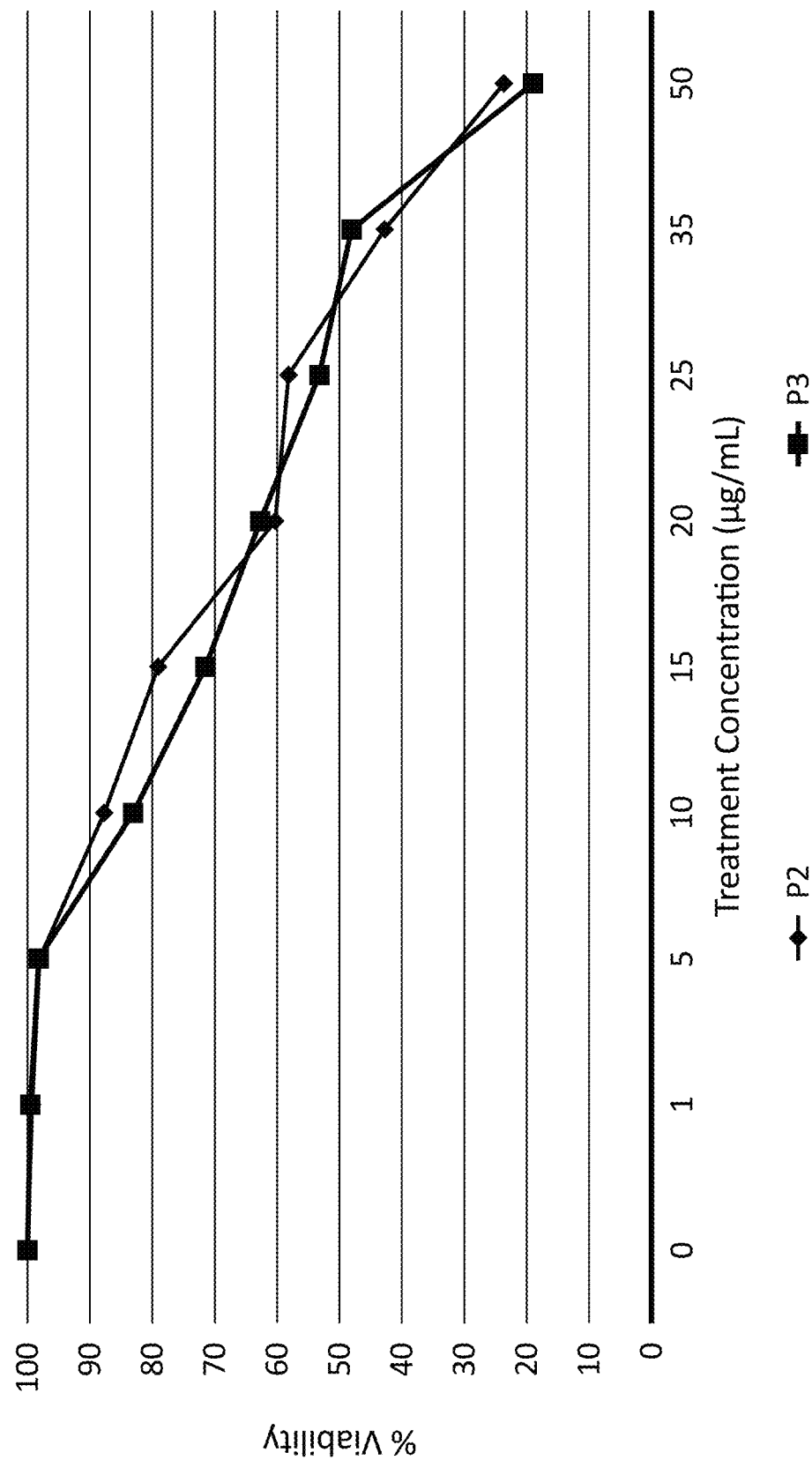
Figure 1E:
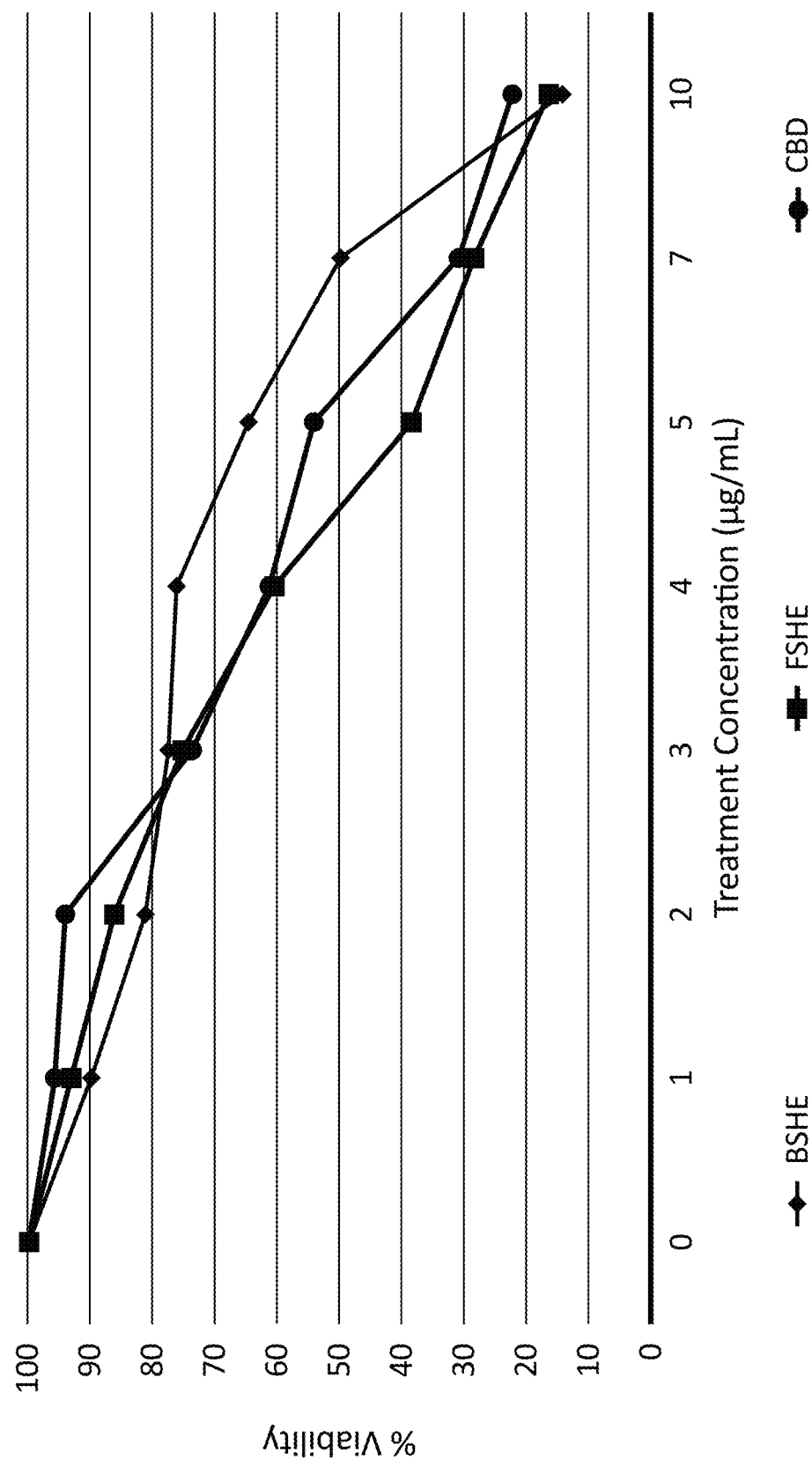

FIGS. 1E and 1F shows grade 1 endometrial cancer organoids response to CE treatment by donor patient. From FIG. 1E, we can see the organoids from P2 are overall more sensitive to FSHE and CBD compared to BSHE. For example, 50% organoid viability per the graph was achieved at a lower dose of FSHE than either CBD or BSHE. Nevertheless, approximate IC50 doses of FSHE, BSHE, and CBD isolate for P2 organoids is between roughly 4 and 7 μg/ml. Of course, actual IC50 dosages are calculated as described in the methods section and the 50% viability determined per the graph is a rough approximation thereof. Like P2, P3 organoids were the least sensitive to BSHE overall where 50% viability based on the graph was at a higher concentration than both CBD isolate and FSHE. Approximate IC50 doses of BSHE, FSHE, and CBD isolate for P3 organoids are also between about 4 and 7 μg/ml. Thus, based on the graphs shown in FIGS. 1A through 1F, all CE are effective at decreasing grade 1 endometrial cancer organoid viability in low estrogen environments, where in each case 10 μg can decrease viability by roughly 70%-90%. We know from our prior work that greater than 10 g/ml CE usually results in a 100% reduction in grade 1 endometrial cancer derived organoid viability, such as by less than or equal to 50 μg/ml. It should be noted though, that less than 10% organoid viability is considered a 95-100% inducement of apoptosis in these experiments due to residual signaling from dead cells and Matrigel.

Turning to FIG. 2A-2H, organoids from four patients having grade 2 endometrial cancer were tested for their response to BSHE, CBD isolate, and FSHE, at 1, 2, 3, 4, 5, 7, and 10 μ/ml, and CBDA at 0, 1, 5, 10, 15, 20, 25, 35, and 50 μg/ml; all organoids were grown in the low estrogen media. Patient 4 was diagnosed with endometrial adenosquamous carcinoma with mutations in ARID1A, HRAS, KMT2D, PTEN, and TP53 genes. Patients 5 and 7 were both diagnosed with endometrial adenocarcinoma with TP53 gene mutations. Patient 5 also had KRAS, MSH6, and PMS2 gene mutations and patient 7 also had PIK3R1, POLE, and PTEN mutations. Patient 9 had unspecified endometrial cancer with unknown gene mutations.

Figure 2A:
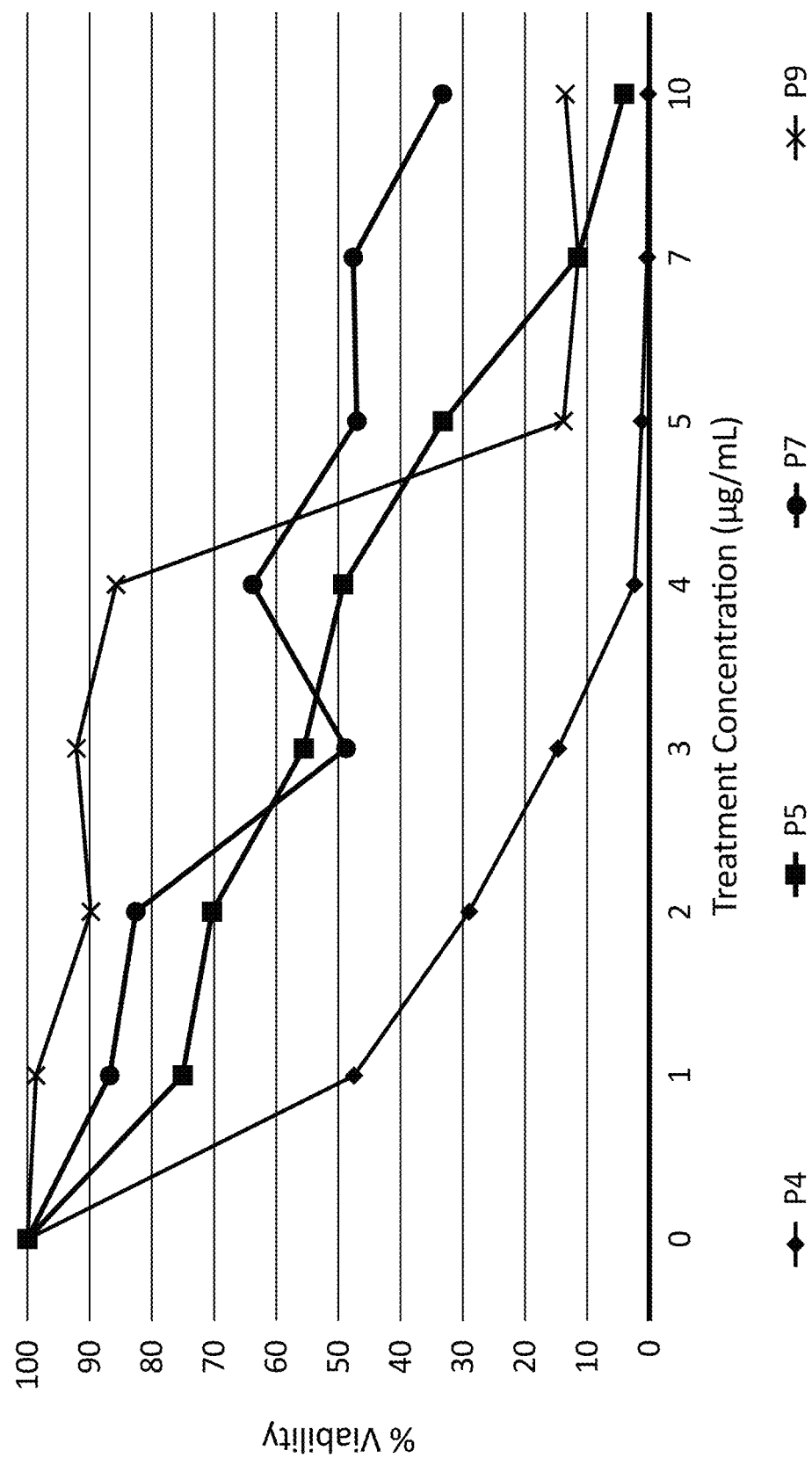
FIGS. 2A, 2B, 2C, 2D, 2E, 2F, 2G, and 2H detail the effect of CE on grade 2 endometrial cancer organoids.

Although all grade 2 organoids were responsive to CE with increasing doses resulting in decreasing organoid viability, as is shown in FIG. 2A, organoids from P4 were the most sensitive to BSHE having a calculated IC50 of about 1 μg/ml and having essential 0% organoid viability at a 4 μg/ml dose. P5 organoids have a calculated BSHE IC50 dose of about 3 μg/ml, with a fairly linear decrease in organoid viability with increase in BSHE dose. At the highest concentration tested, BSHE was able to decrease P5 grade 2 viability by essentially 100%. Organoids from P7 had a somewhat linear decrease in viability but were over all less sensitive to BSHE than the other grade 2 organoids with a maximal decrease in viability of about 70% at 10 g/ml and an approximated BSHE IC50 dose of about 7 μg/ml. P9 organoids seem somewhat resistant to BSHE at lower doses, with a sharp decrease in organoid viability at 5 μg/ml. Thereafter, at 7 μg/ml and 10 μg/ml, BSHE essentially induced 100% apoptosis in P9 organoids, with an estimated IC50 of about 4 μg/ml. Again, our prior work indicated that when treated with BSHE doses greater than 10 μg/ml, endometrial cancer organoids were not at all viable with 100% apoptosis. From the present data an IC50 dose of BSHE for grade 2 endometrial cancer is between about 1 μg/ml and about 5 μg/ml.

Figure 2B:
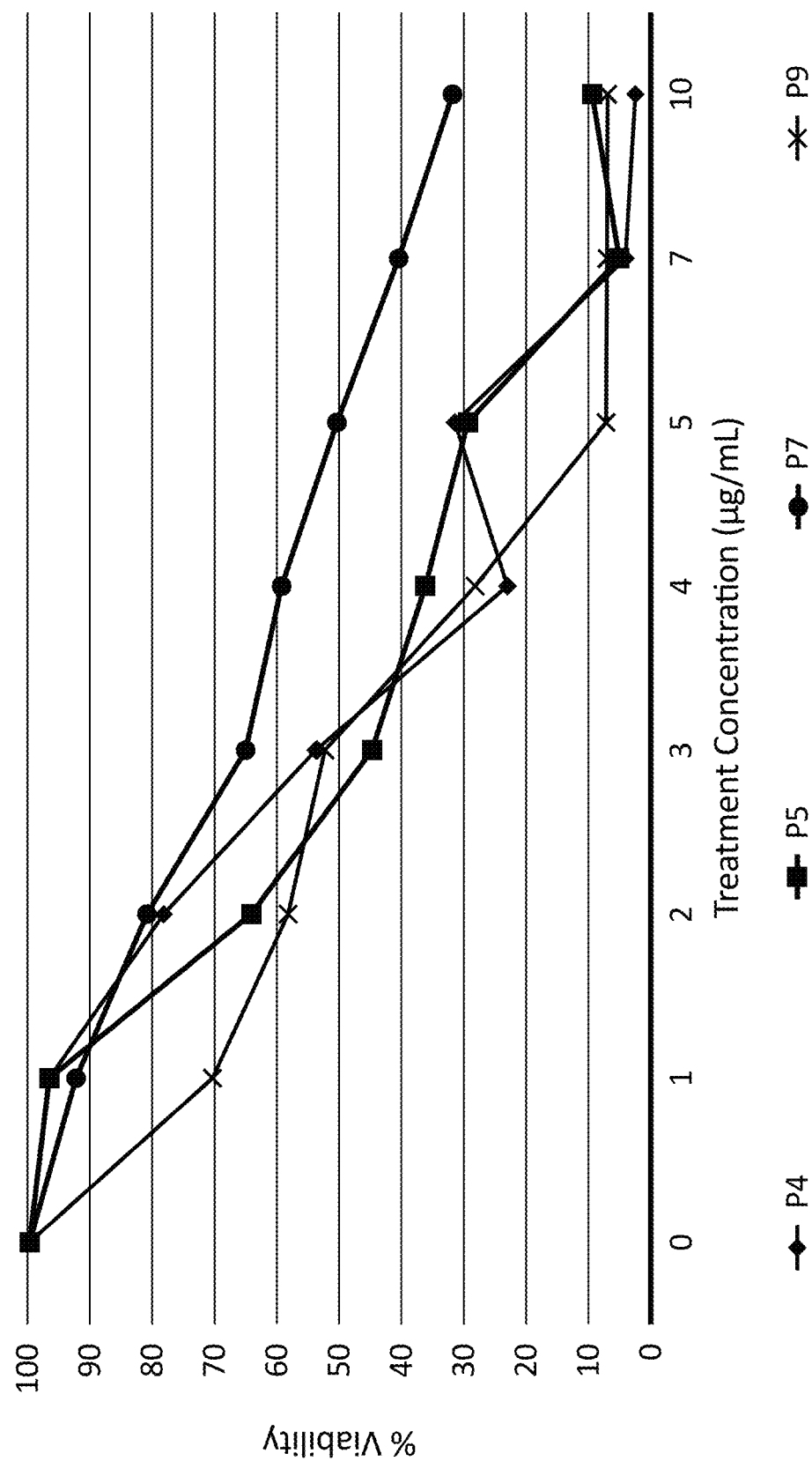
Figure 2C:
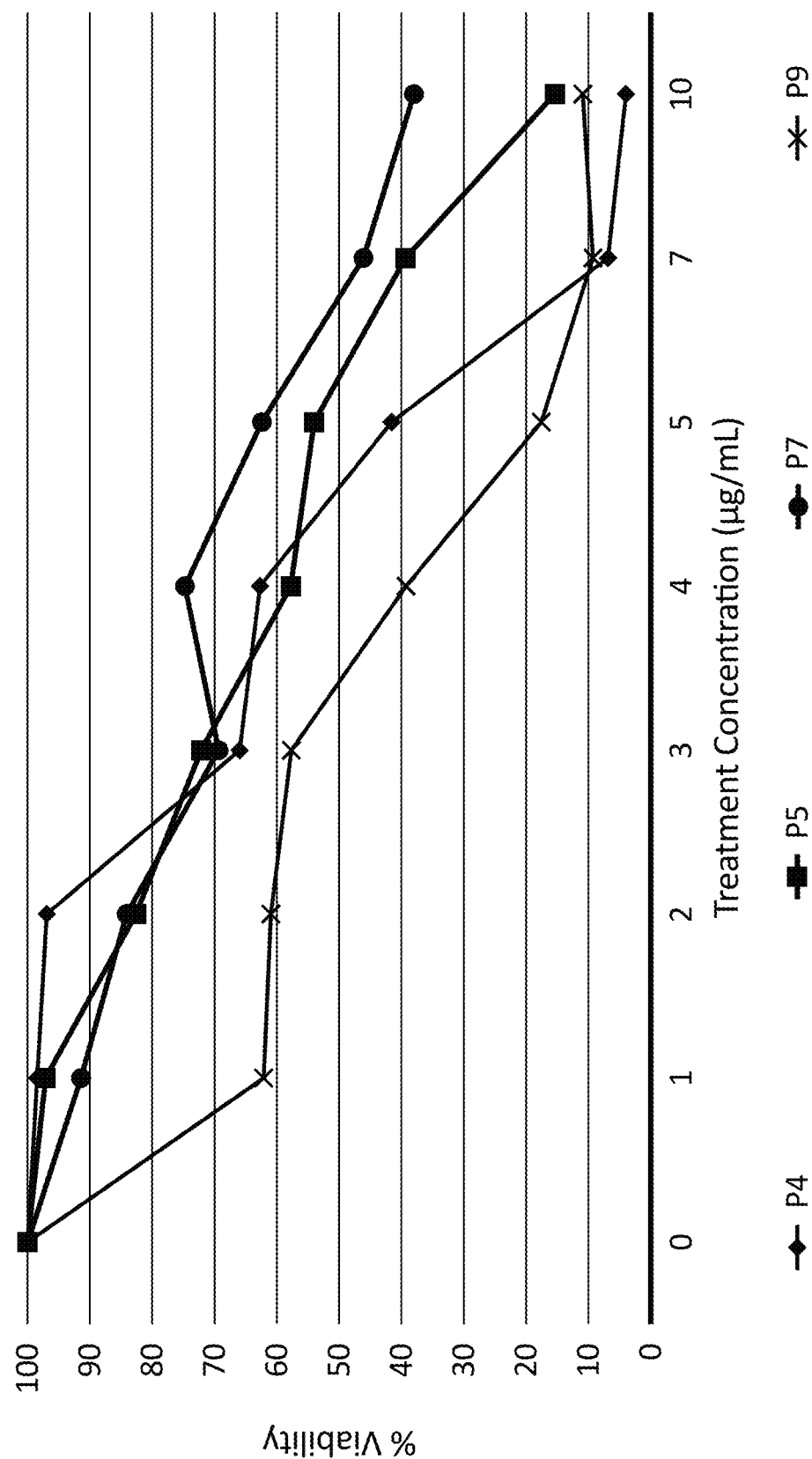
Figure 2D:
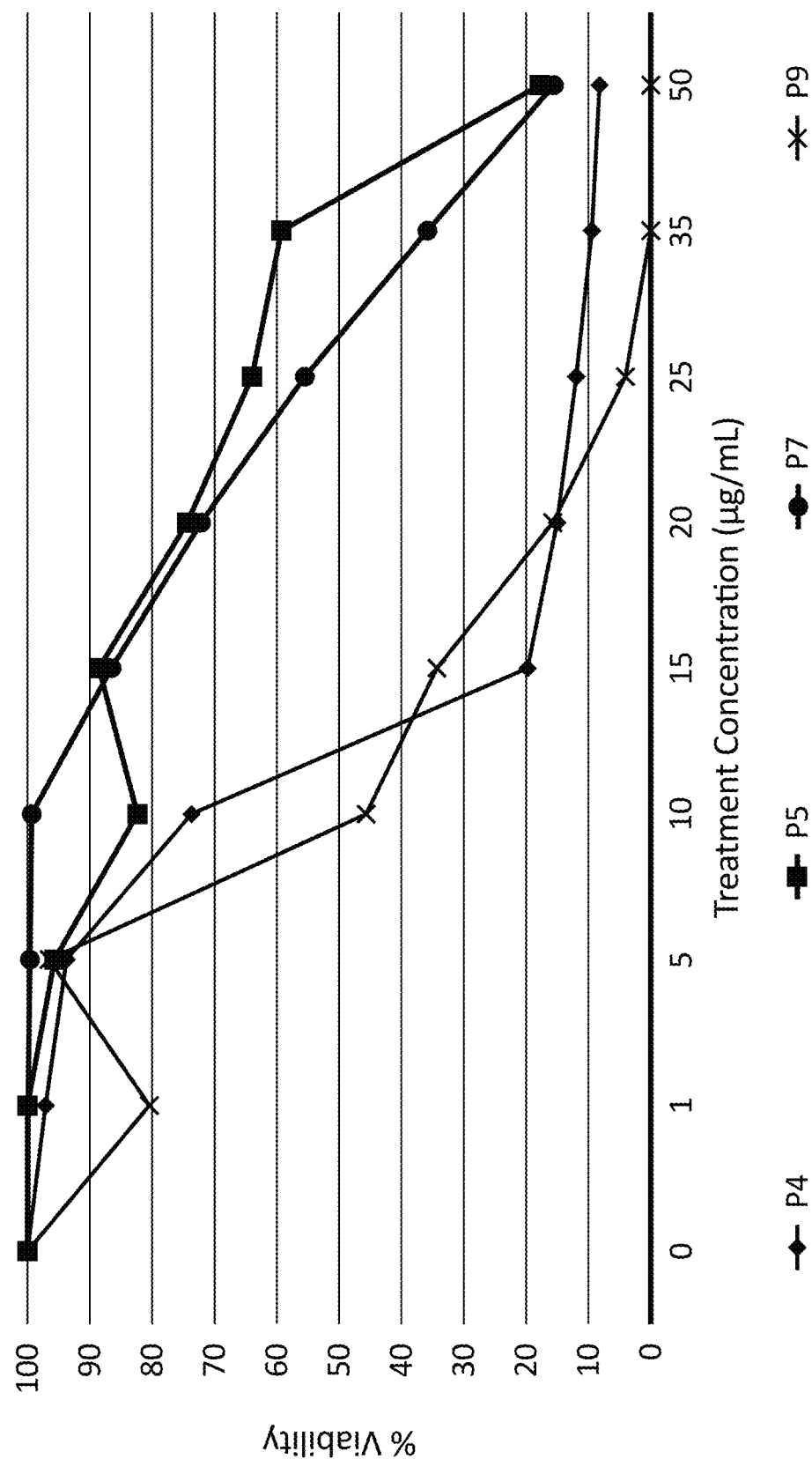

In contrast, all four lines of grade 2 organoids tested responded to CBD isolate and FSHE and in a more-or-less dose dependent manner as is shown in FIGS. 2B and 2C. Referring to FIG. 2C, the calculated FSHE IC50 doses for P4 and P5 are about 4.3 μg/ml and 5.0 μg/ml, respectively. Approximate FSHE IC50 dose for P9 and P7 are about 3.5 μg/ml and 7 μg/ml, respectively. Thus, P9 organoids are the most sensitive to FSHE and P7 organoids are again the least sensitive when grown in a low estrogen environment and FSHE IC50 doses for grade 2 endometrial cancer organoids is from about 3 μg/ml to about 7 μg/ml. Referring to FIG. 2B, P4 and P5 organoids had an increased sensitivity to CBD isolate compared to FSHE, with calculated CBD isolate IC50 doses of about 3.1 μg/ml and about 2.9 μg/ml respectively. Thus, both sets of organoids have very close CBD isolate IC50 doses. The approximate CBD isolate IC50 dose for P9 organoids is also about 3 μg/ml, but for P7 organoids is closer to 5 μg/ml, making these organoids again, the least sensitive to CE.

As with grade 1 endometrial cancer organoids, grade 2 endometrial cancer organoids required higher doses of CBDA than the other CE to induce apoptosis. For example, the calculated CBDA IC50 dose for P4 and P5 are about 12 μg/ml and about 33 μg/ml respectively. The approximate IC50 doses for CBDA in P7 and P9 are about 25 μg/ml and 10 μg/ml, respectively. Thus, although at a higher dose than other CE, P9 organoids are the most sensitive to CBDA and P5 organoids the most resistant. Nevertheless, at 50 μg/ml CBDA, all four sets of organoids were decreased in viability from between about 80% and above 90%, which is still a healthy decrease in viability compared to the control. And, as we already mentioned 50 μg/ml of any CE should have the same or better inhibitory effect on organoid viability.

Figure 2E:
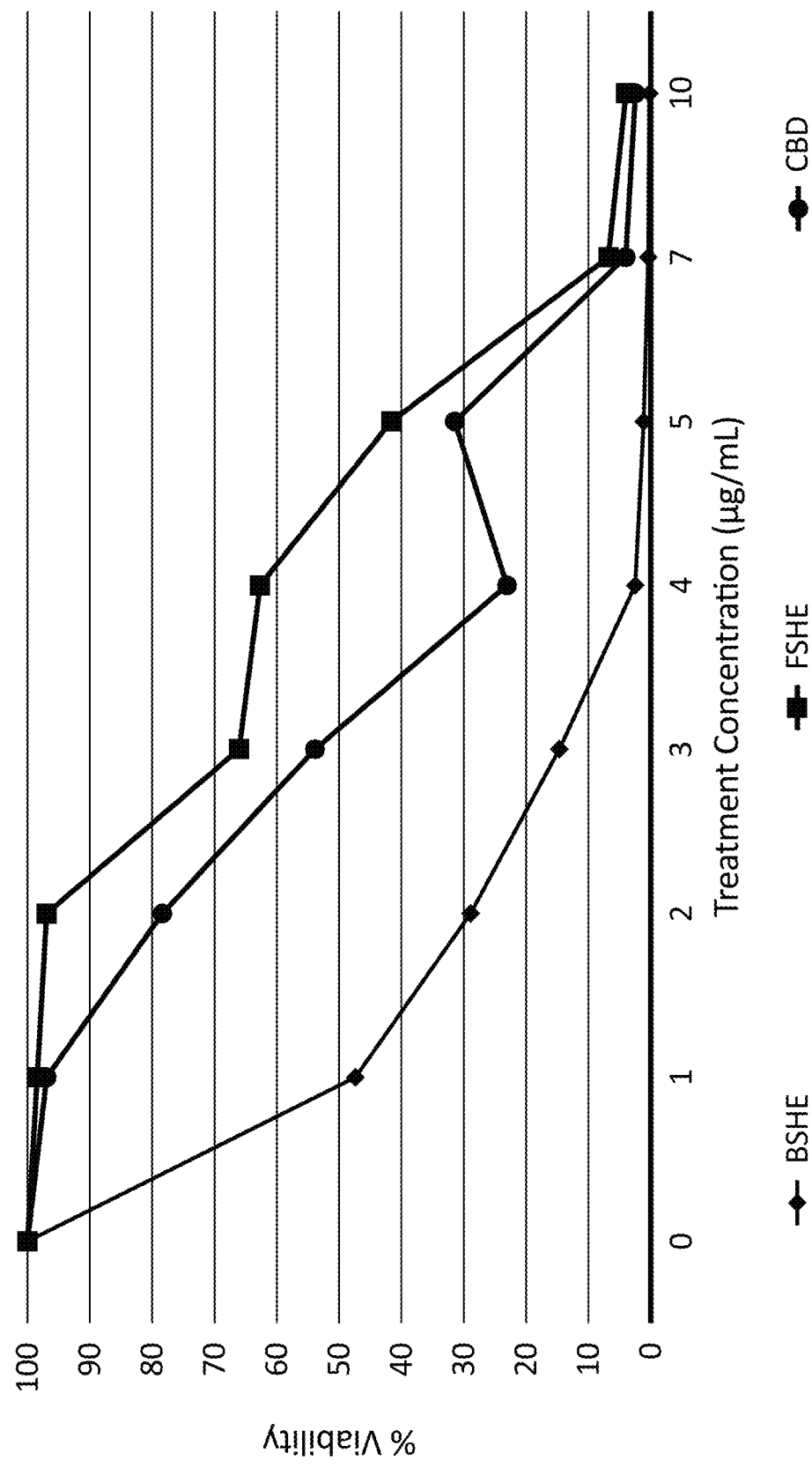
Figure 2F:
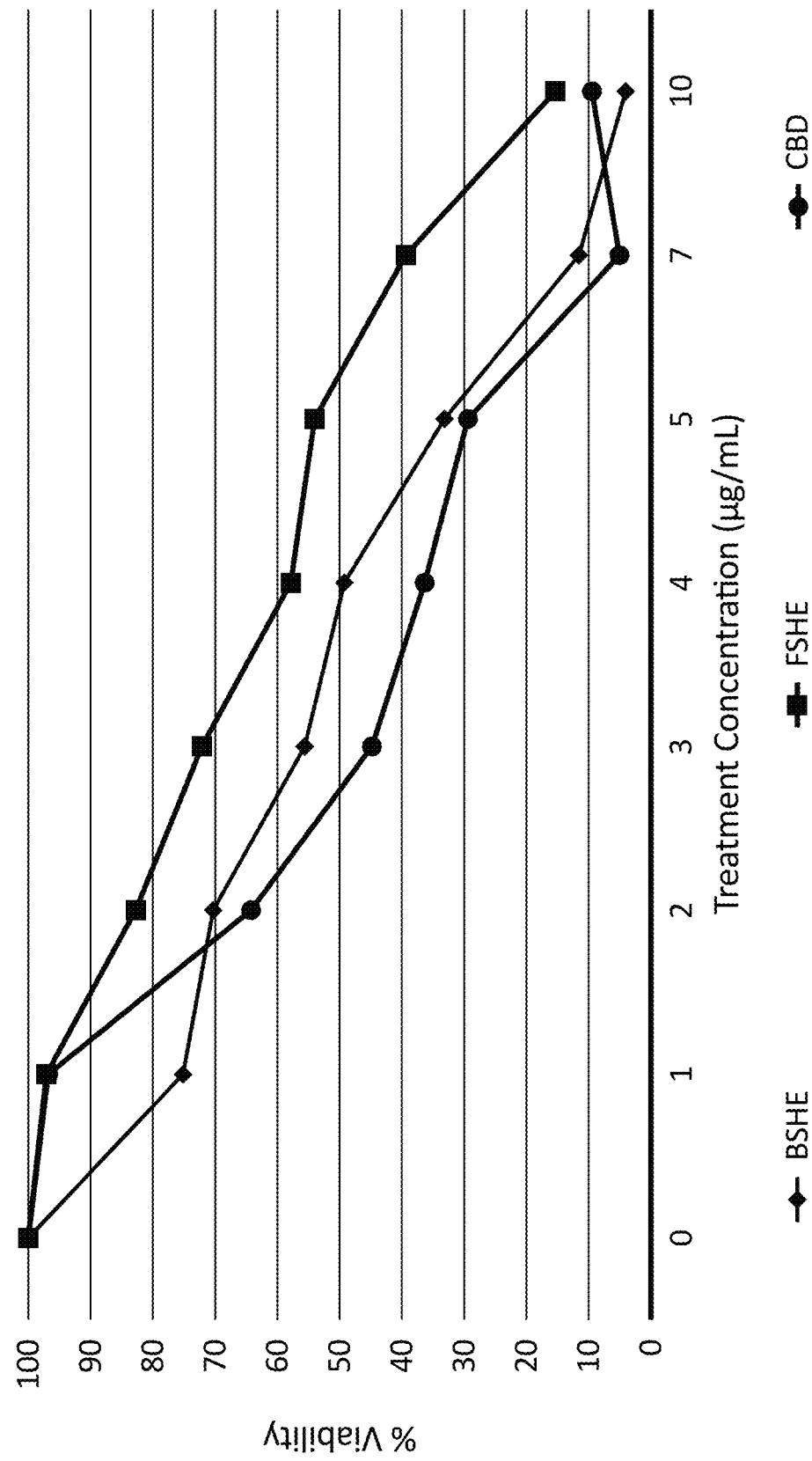
Figure 2G:
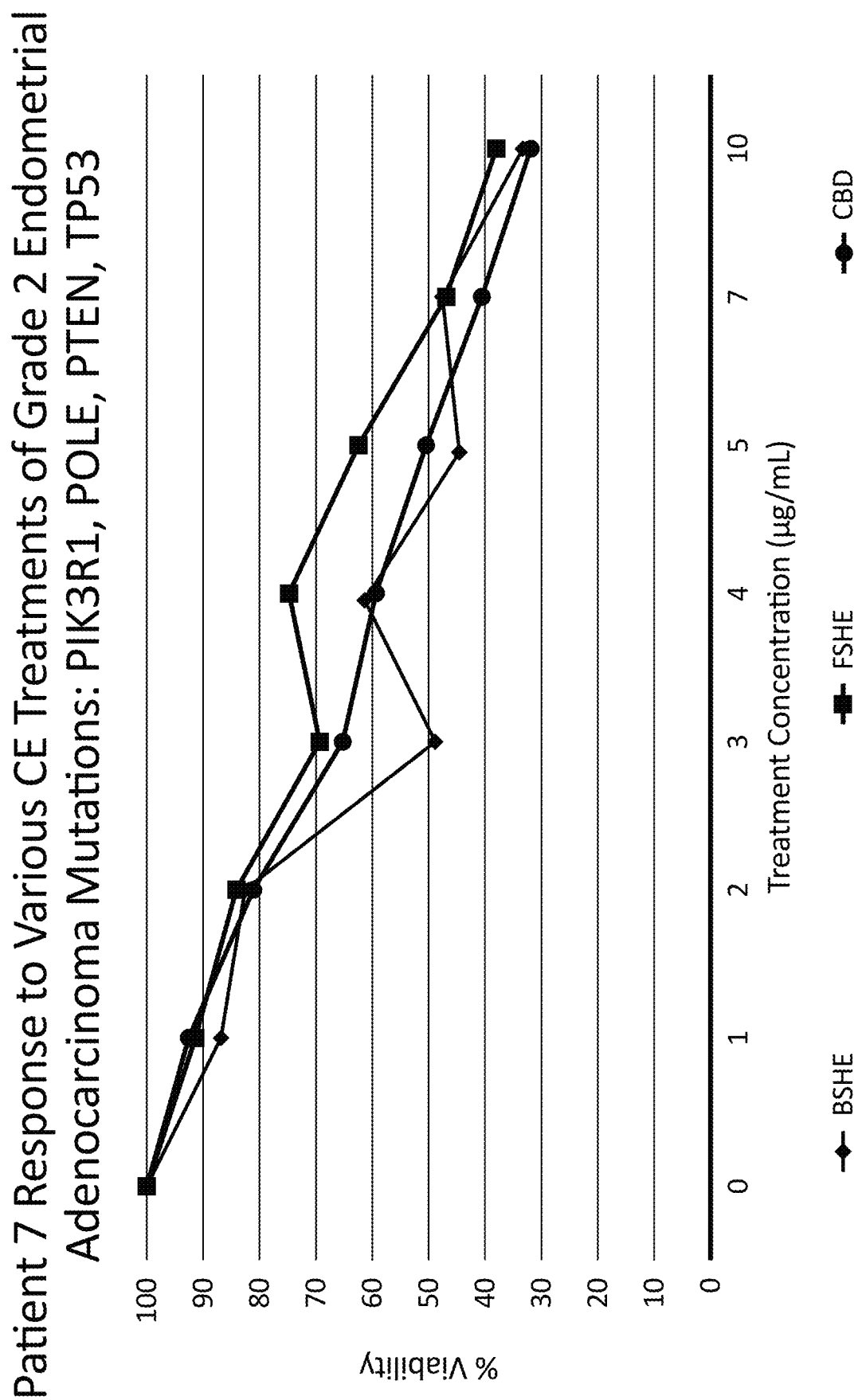
Figure 2H:
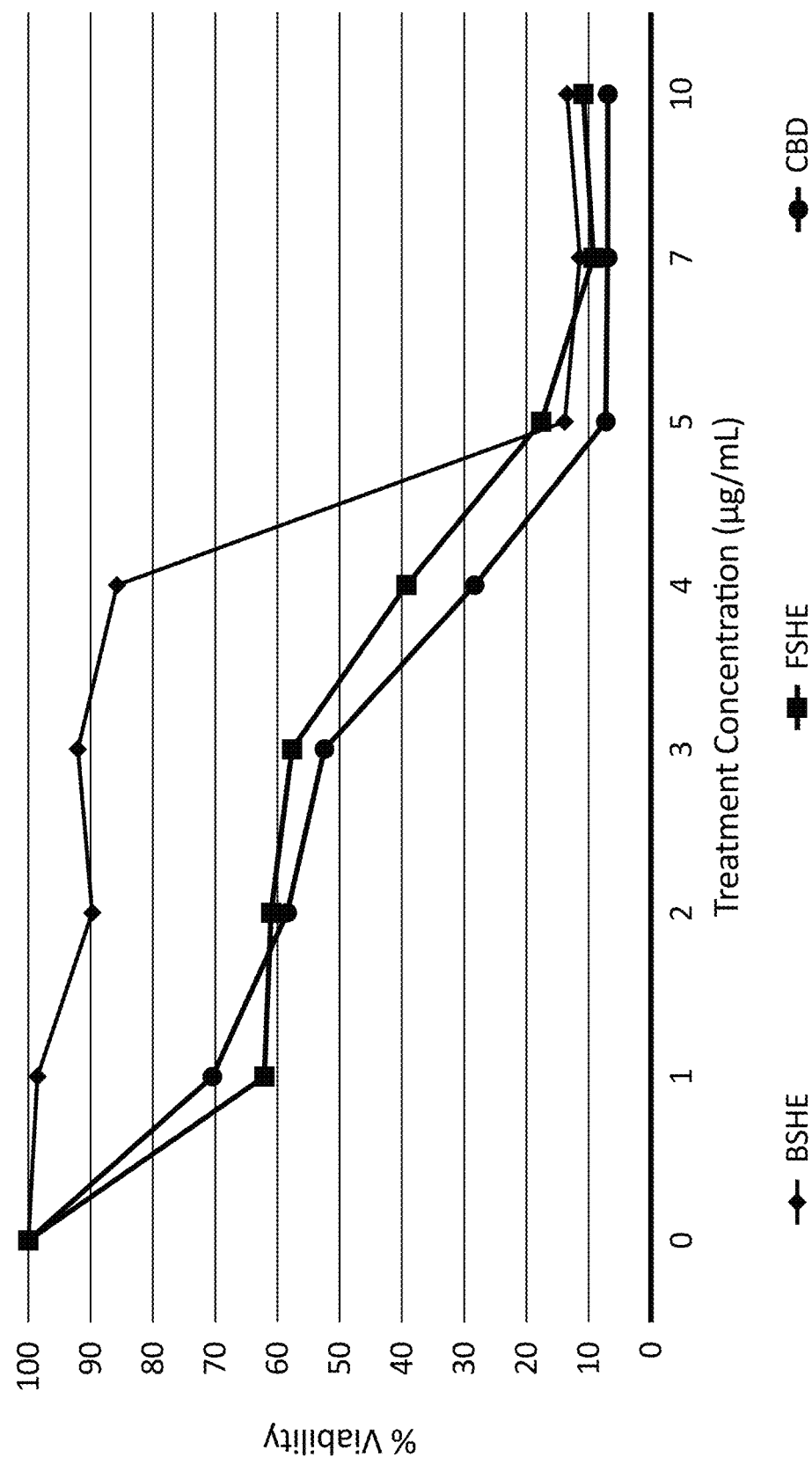
Figure 3A:
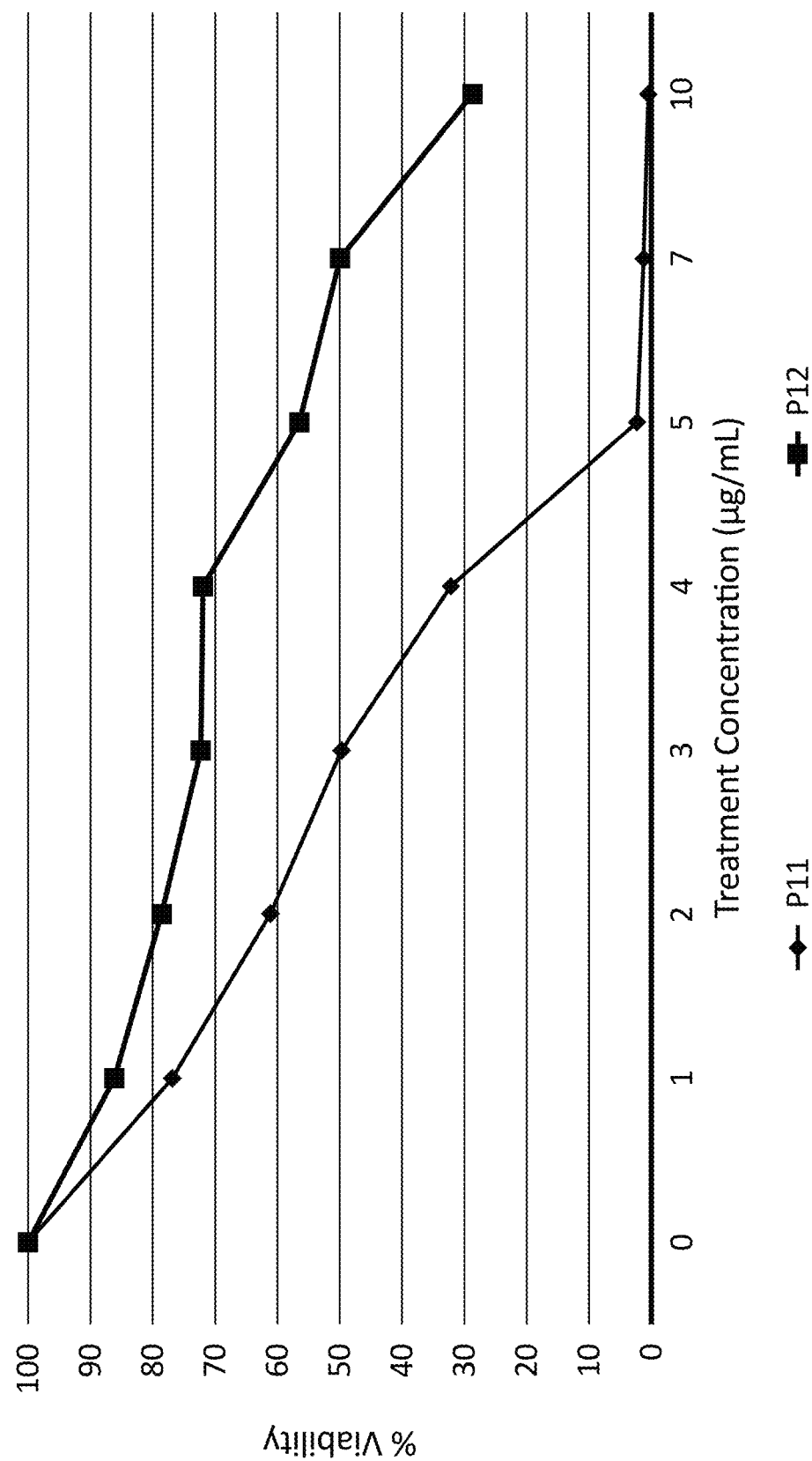
FIGS. 3A, 3B, 3C, 3D, 3E, and 3F detail the effect of CE on grade 3 endometrial cancer organoids.
Figure 3B:
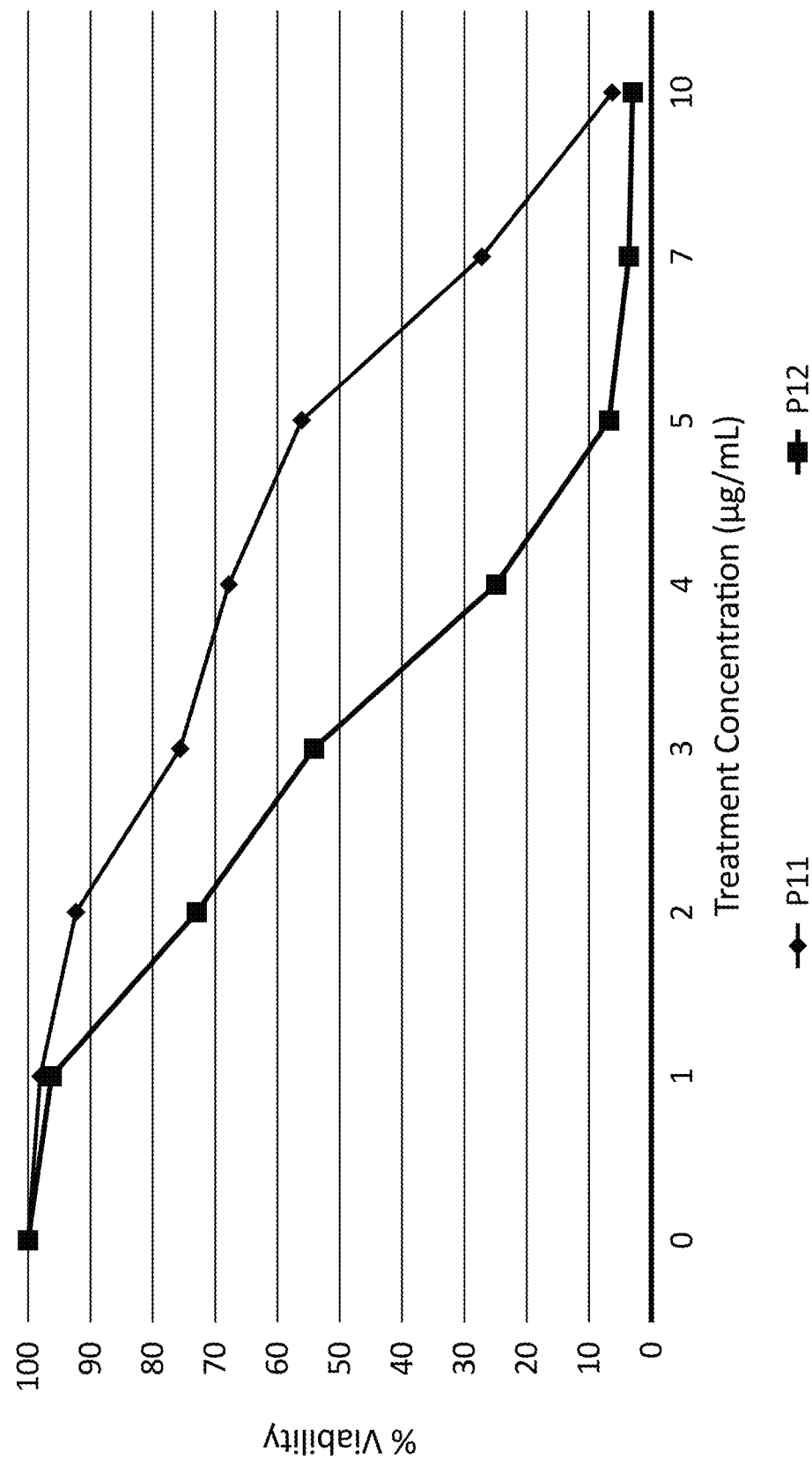
Figure 3C:
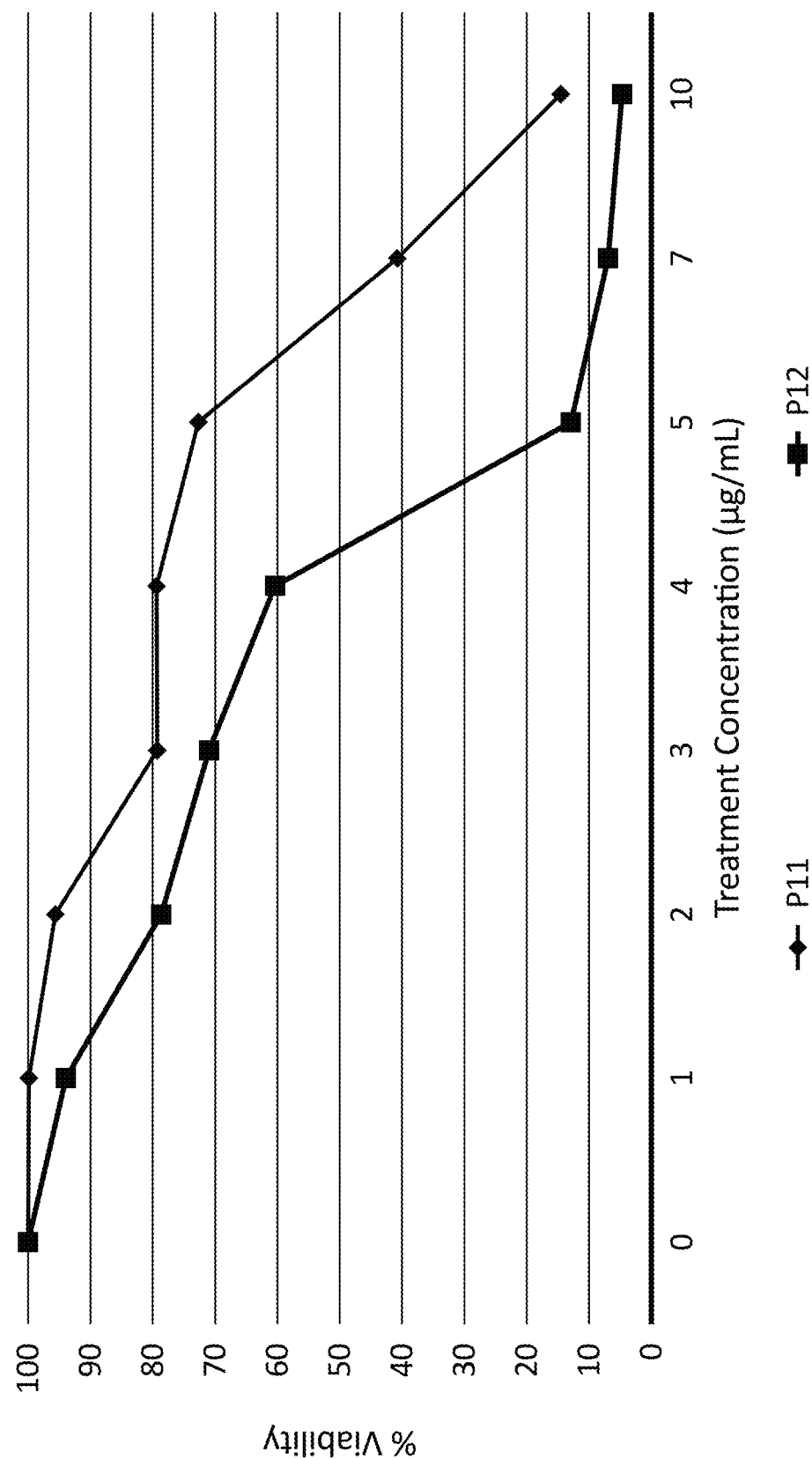
Figure 3D:
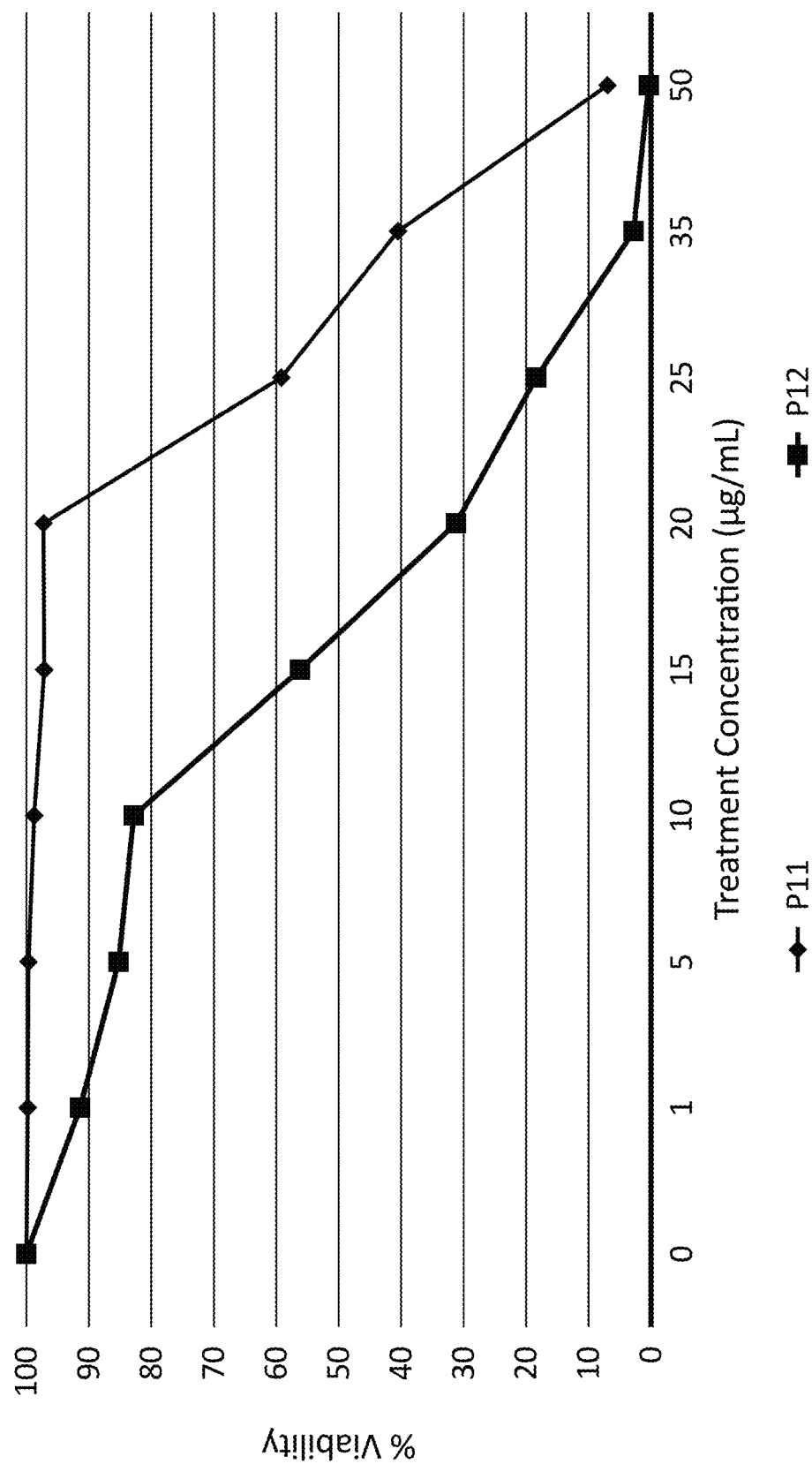
Figure 3E:
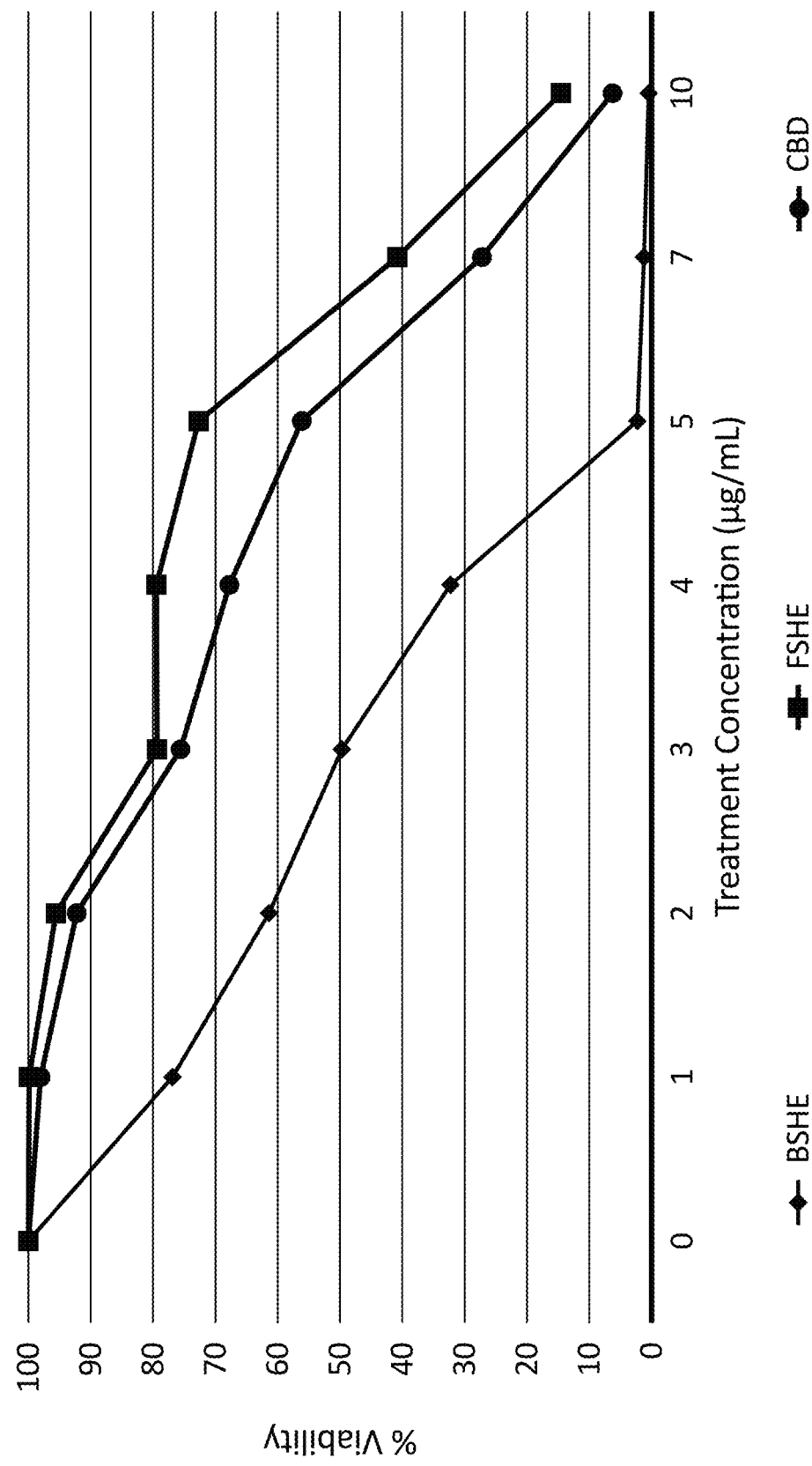
Figure 3F:
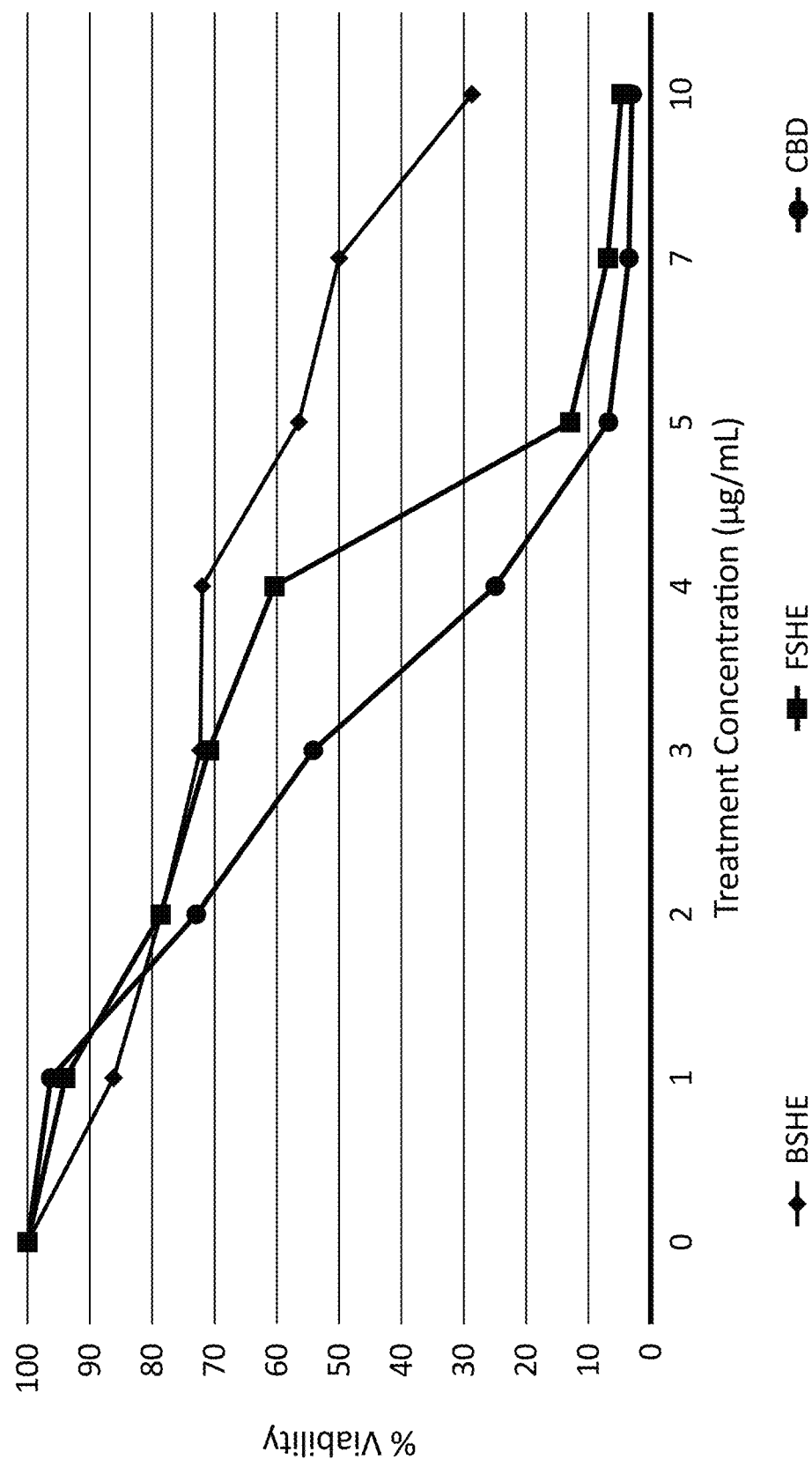

FIGS. 2E through 2H show the same data for BSHE, FSHE, and CBD isolate but is presented as a function of patient donor instead of by CE treatment. CBDA data was omitted from these graphs due to higher concentrations needed to obtain decreases in viability. FIG. 2E shows that P4 organoids were the most sensitive to BSHE having a calculated IC50 of about 1 μg/ml, and the least sensitive to FSHE having a calculated IC50 of about 4.3 μg/ml. Sensitivity to CBD isolate was therebetween, with a calculated IC50 of about 3.1 μg/ml. Thus, at least with CE of BSHE, FSHE, and CBD isolate, a dose of between about 1 μg/ml and 4 μg/ml should decrease P4 organoid viability by about at least 50%, if not more. P5 organoids had a different sensitivity profile being the most sensitive to CBD, then BSHE, and lastly to FSHE (see, e.g., FIG. 2G) with calculated IC50s of about 2.8 μg/ml, 3.1 μg/ml, and 5.0 μg/ml respectively. Thus, treatment with about 3 μg/ml to about 5 μg/ml BSHE, FSHE, or CBD isolate should decrease P5 organoids by about 50%. Interestingly, P7 organoids were generally not as sensitive to CE as the other grade 2 endometrial cancer organoids and were the only ones having a POLE mutation. Generally, POLE mutations are associated with decreased DNA repair and thus, an increase accumulation of errors during DNA replication. Endometrial cancers having POLE mutations are characterized by their own molecular group. P7 organoids had approximate IC50 doses of about 5 μg/ml for each of BSHE and CBD isolate and 7 μg/ml for FSHE. Thus, a slightly higher dose of these CEs may be needed for endometrial cancers having POLE mutations. P9 organoids had yet another CE sensitivity profile-being the most sensitive to CBD, then FSHE, and lastly BSHE with approximated IC50 doses of 3, 3.5, and 4 μg/ml, respectively. As each of the grade 2 organoids differ histologically (or is unknown) molecularly, it is unknown if these differences give rise to the different CE sensitivity profiles.

Referring to FIGS. 3A-3F, the effects of CE in a low estrogen environment are shown. Patient 11 (P11) was diagnosed with endometrial adenocarcinoma having MAPK3, PIK3R1, PTEN, and TP53, gene mutations. Patient 12 (P12) had unspecified endometrial cancer with unknown mutations. As is shown in FIGS. 3A-3D, organoids from P11 were more sensitive to BSHE having an approximated IC50 dose for this CE of about 3.2 μg/ml. The calculated IC50 dose of BSHE for organoids from P12 is about 6 μg/ml. In contrast, organoids from P12 were more sensitive to CBD isolate, FSHE, and CBDA than those from P11. Calculated IC50 doses for CBD isolate, FSHE, and CBDA for P12 organoids are about 3, 4, and 15 μg/ml, respectively. Approximated (from the graph) IC50 doses for P11 organoids are 5 μg/ml (CBD isolate), 6 g/ml (FSHE), and 30 μg/ml (CBDA). When viewing the same data as a function of patient, it is readily apparent that for P11 organoids, BSHE is more effective at inducing apoptosis than CBD isolate and FSHE. Conversely, P12 organoids were more sensitive to CBD than either FSHE or BSHE. Taking the calculated and approximated IC50 values for P11 and P12 organoids, a dosage of any one of CBD isolate, FSHE, and BSHE of between about 3 and 6 μg/ml should decrease organoid viability by about 50%, if not more.

Interestingly, organoids created from grades 1, 2, and 3 endometrial cancer all responded to CE by decreasing organoid viability. In a low estrogen environment, IC50 doses for all grades ranged from about 1 μg/ml to about 7 μg/ml for BSHE, FSHE, and CBD isolate, with many IC50 doses falling between about 3 μg/ml and about 5 μg/ml. Increased amounts of CBDA, however, was required for an IC50 dosing in all three grades of endometrial cancer, with IC50s for CBDA ranging from about 12 μg/ml to about 30-35 μg/ml.

To further our studies on the effects of *cannabis* extracts comprising CBD, Applicant looked at endometrial cancer tumor volume in mice. Generally, EC stem cells from a different patient, P6, were injected into the mice and allowed to grow in vivo, without administering estrogen. That is, hormones present in the mice were endogenous hormones produced by the mice. P6 was diagnosed with endometrial adenocarcinoma having ERBB3, JAK1, PTEN, and TP53 gene mutations. In experiments not shown here, P6 organoids were characterized as being "low responders," generally requiring BSHE, FSHE, and CBD doses of 15 μg/ml or 20 μg/ml to achieve about 100% induced apoptosis in organoids. Interestingly, these organoids did not need greater than 50 μg/ml CBDA to achieve the same. After tumors reached a certain size, mice were either injected (3 times/week) with the extract-delivery vehicle or with particular *cannabis* extract. After the number of days indicated on the x-axis of FIG. 4, tumor size was measured. The details regarding patient-derived xenograft methodology and experimental protocol are provided in the Methods section.

Figure 4:
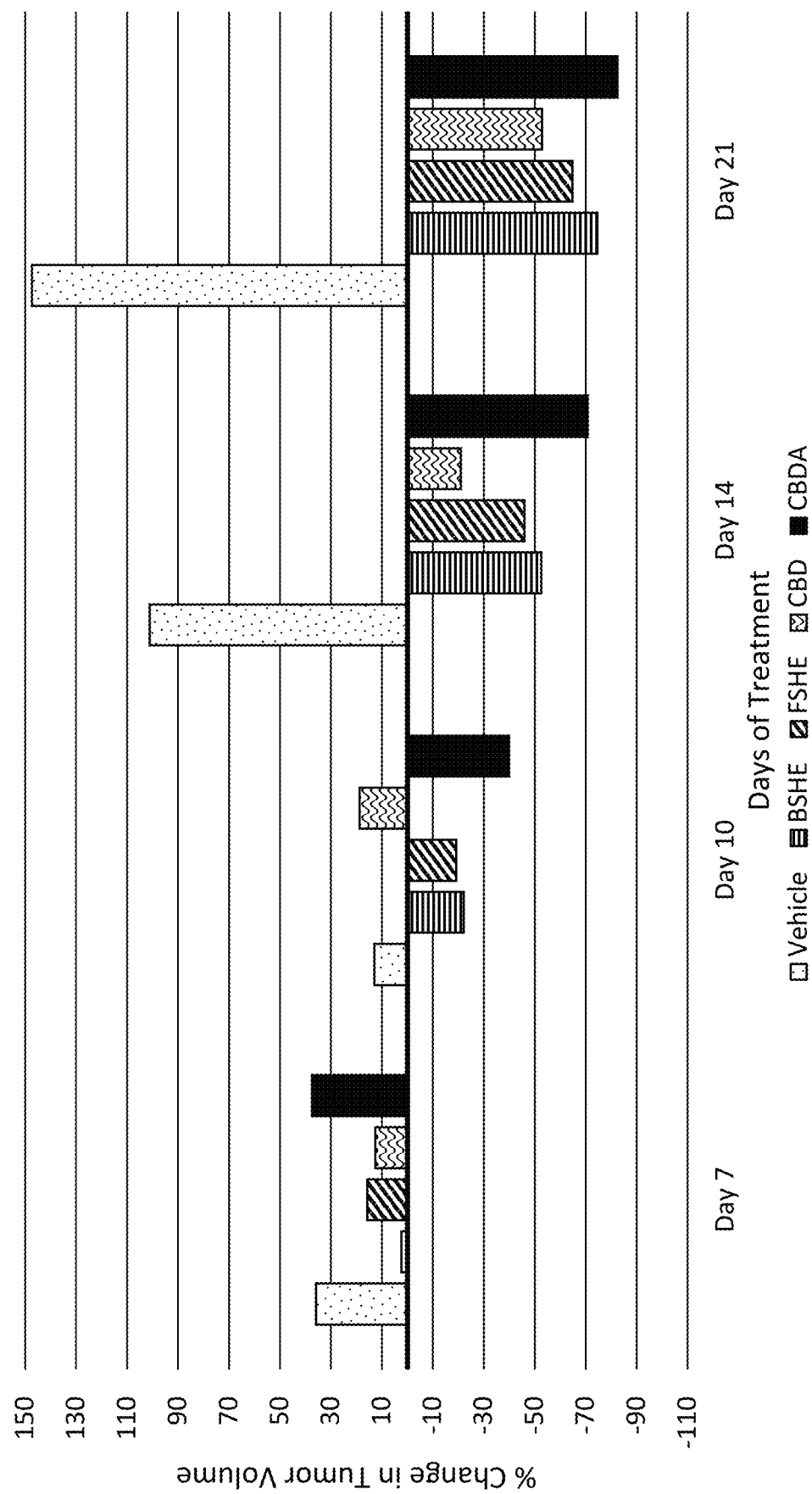
FIG. 4 depicts a graphical chart of endometrial cancer tumor volumes within mice, wherein the mice were injected with patient derived endometrial cancer cells, grade 2 collected from patient 6 (P6). The data shows the change in tumor volume from day 7 to day 21 and depicting the therapeutic efficacy of the various *cannabis* extracts on the tumor volumes.

Referring to FIG. 4, the number of days of treatment is plotted against an % change in tumor volume for each of the vehicle, BSHE, FSHE, CBD isolate, and CBDA. The % change is an average number taken from tumor volumes of three mice compared to the starting average tumor volume on day 0 of treatment. Change can either be positive (tumor increases in size) or negative (tumor decreases in size). As expected, the untreated, control (i.e., vehicle) tumor continuously increased in volume over 21 days with almost a 150% increase from the day treatment started. In contrast, tumors in mice treated with a CE decreased in size. Thus, we have shown that systemic delivery of CE can be used to treat endometrial cancer and specifically grade 2 endometrial cancer, which is categorized as being type 1, which is estrogen sensitive. This is an important verification as it confirms bioavailability of the various CEs used in these studies.

Successful delivery of the various CE is validated by the observed changes in tumor volume. For example, after one week of treatment (i.e., 3 doses of about 30 mg/kg CE) all tumor averages indicate an initial increase in size. By day 10, however, most average tumor volumes began to decrease with the tumors in mice treated with CBDA showing the greatest decrease over the three days of from a little over a 30% increase to a greater than 30% decrease; an overall decrease that is greater than 60% in just three days. Mice treated with BSHE and FSHE showed a similar switch from an increase in average tumor volume to a decrease average tumor volume, but not as dramatic as that observed with CBDA. Interestingly, the tumors in mice treated with CBD isolate were not as responsive as the tumors in mice treated with the other *cannabis* extracts, which is especially surprising as CBDA is a precursor to CBD. Within 2 weeks (14 days-6 doses total), most tumors were at least 50% decreased in volume compared to their starting size, except for those in the mice treated with CBD, which was less than 50%, but still a decrease in average tumor volumes. In contrast, mice treated with CBDA showed an average decrease in tumor volume of 70% compared to starting tumor volume averages. By day 21, only three weeks of treatment, 9 doses total, average tumor volume in each of the treatment groups decreased by at least 50%, with those treated with CBDA approaching 100% resolution. What is even more amazing is that when left untreated, the average tumor volume was slightly less than a 150% increase. Thus, the CEs not only prevented endometrial tumor volume from increasing, but they also reversed tumor volume, in some cases almost completely. These results confirm what was observed in the organoid experiments and what was observed in the human patient that was treated with BSHE, which is detailed later in this specification.

Notably, the concentrations of CBD used in the mouse model experiments are on the low end of what would be considered a therapeutic dose for administering to a human patient or a mouse. For example, the 30 mg/kg given to the mice translates to about 170 mg for a human of average size. Recall that a CBD isolate is currently prescribed in the US at a concentration of 5-50 mg/kg daily. We intentionally used low doses to treat mice to show the impact of various CEs at these low doses on tumor volume over time rather than forcing the data to zero, by using double, triple, or higher of the dose as administered to the mice, each of which would be appropriate human equivalent doses. Furthermore, even with the lower dosing, within 3 weeks of treatment, virtually all of the tumor volumes were progressing toward zero, especially those treated with CBDA. Therefore, when comparing dosages used in mice to those applied to the organoids, we saw that each sample in the mice retained the efficacy from the organoid data. In other words, endometrial cancer cells obtained from the same patient were responsive to CE in both an organoid form and patient-derived xenograft form. As such, administering higher doses of CE will yield a greater reduction in tumor volume in the mouse model. From all of these experiments taken in total, it is quite clear that, administering CE is effective in greatly decreasing the volume of endometrial cancer tumors, which not only slows the growth of endometrial cancer tumors, but may eradicate tumor cells altogether, as is demonstrated in our mouse models.

Having firmly established that grades 1, 2, and 3, endometrial cancer are inhibited, and even reversed, by treatment with various CEs we wanted to determine if sensitivity to CEs would be altered by the presence of excess estrogen, which is the typical hormone state for pre-menopausal women with endometrial cancer. Notably, the prior art teaches that blocking of estrogen is a critical first line treatment for estrogen sensitive cancers. Since grades 1 and 2 endometrial cancers fall under type 1, estrogen sensitive cancer, it was with great surprise that we found that administering CE to organoids in the presence of high amounts of estrogen markedly improved the inhibitory effect of CE compared to that observed when treated with the CEs grown in standard media estrogen levels. Generally, grade 1 and grade 2 endometrial cancer organoids were grown under normal conditions. Thereafter, we added IC50 doses of CE, specifically BSHE, and/or a specific concentration of estrogen solution to the media. After treatment, organoid viability was determined as described in the Methods section. The two different concentrations of estrogen (i.e., a water soluble form of β-estradiol from SIGMA-ALDRICH, product number E4389) used in these experiments were 100 nM and 400 nM.

Figure 5A:
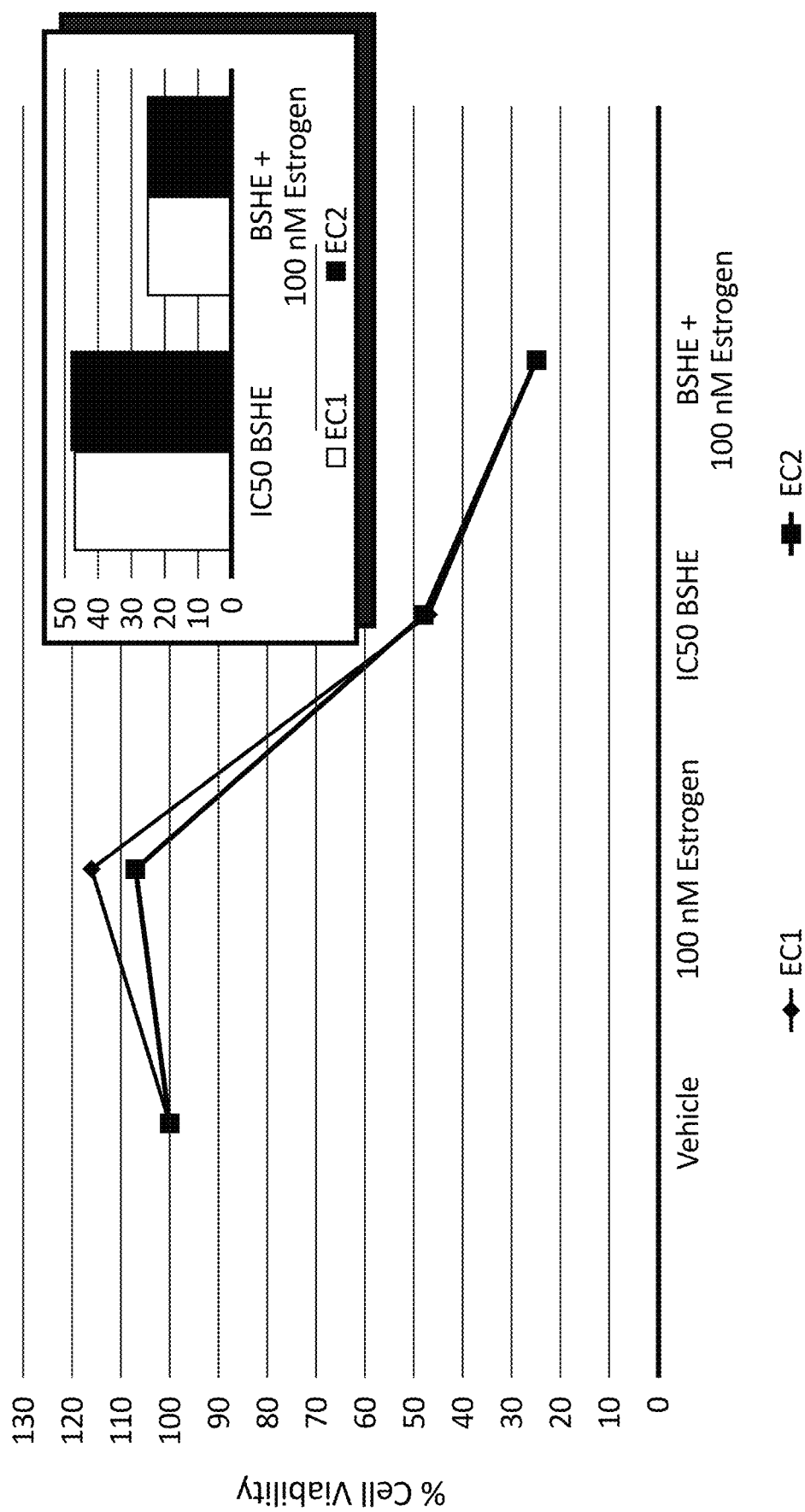
FIGS. 5A and 5B detail the effects of estrogen on endometrial cancer organoid viability alone and in the presence of 100 nM and 400 nM estrogen respectively. Inserts detail the difference in organoid viability when treated with an IC50 dose of CE in a low estrogen/estrogen free environment and the corresponding high estrogen environments.
Figure 5B:
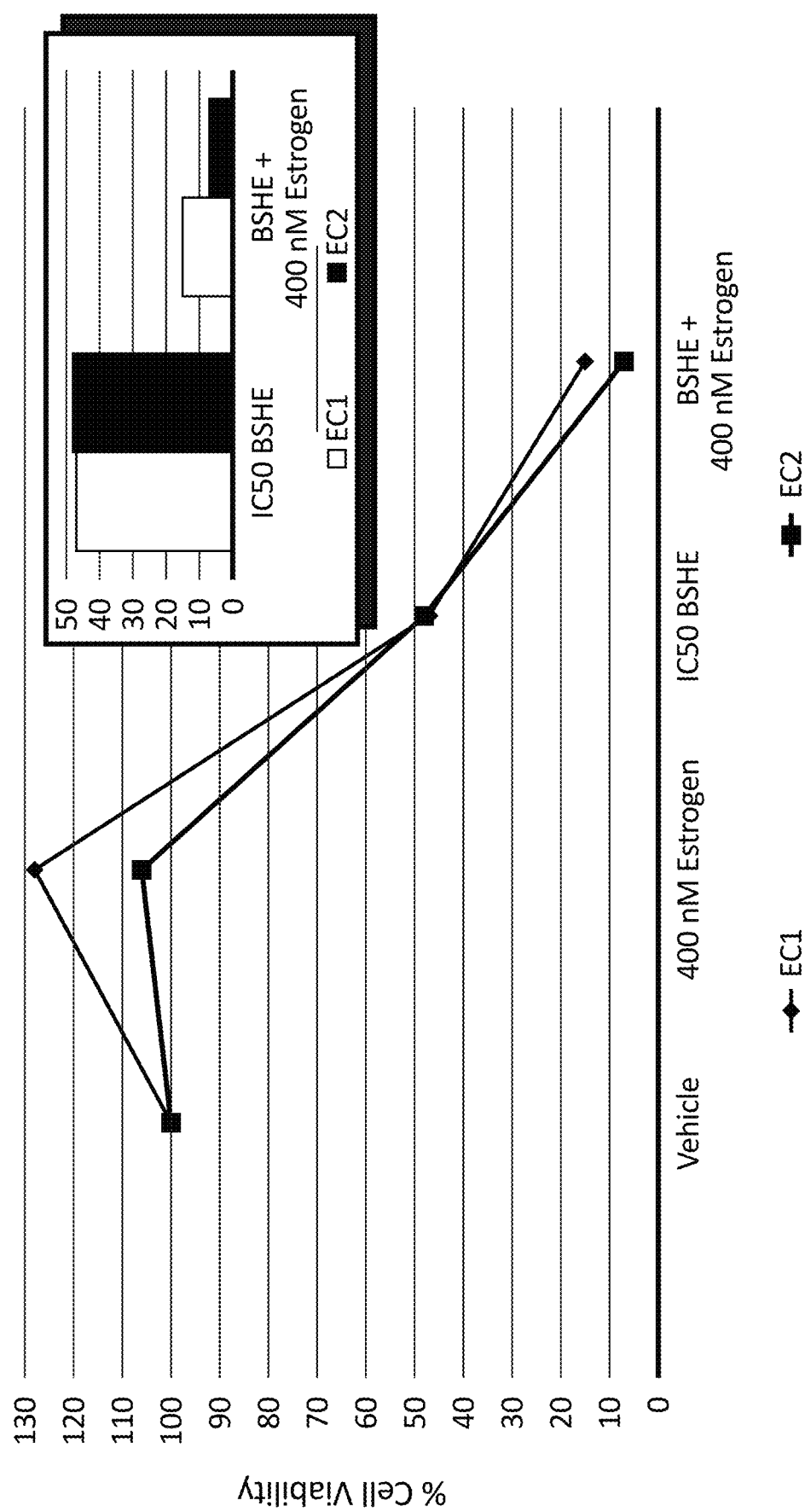

Referring to FIGS. 5A and 5B, when grades 1 and 2 endometrial cancer (EC) organoids were respectively treated with 100 nM and 400 nM estrogen alone, percent viability unsurprisingly increased. The increase in percent viability of grade 1 EC organoids was greater than that of the grade 2 EC organoids when treated with both 100 nM and 400 nM estrogen. Further, as expected, IC50 doses of BSHE determined for both grade 1 and grade 2 organoids reduced organoid viability by about 50% in normal media. The IC50 doses of BSHE for these organoids is 3.1 µg/ml (grade 1 EC) and 4.5 µg/ml 1 (grade 2 EC), which is within the range of IC50 doses expected in growth media, as we demonstrated above. Surprisingly, when the IC50 doses of CE were administered with 100 nM estrogen, the percentage of viable cells decreased to about 25% for both grades of EC cancer. This is roughly a 50% improvement over the IC50 dose of BSHE determined in standard growth media. Thus, CE (e.g., BSHE) was even more effective in inducing grade 1 and grade 2 EC organoid apoptosis in the presences of increased amounts of estrogen than with the standard amount (2 nM) of estrogen present in growth media. This result was completely contrary to what we expected. That is, current views in literature indicate that unopposed estrogen will promote proliferation of grades 1 and 2 EC, which we observed, and is shown in FIGS. 5A and 5B. Thus, we believed that adding a high amount of estrogen to the organoid environment would inhibit CE induced apoptosis, or at best have no effect on CE induced apoptosis at all. In other words, we expected the IC50 doses of BSHE to have the same effect (e.g., decrease viability by 50%) as in a regular media estrogen or to be less than 50% effective in decreasing organoid viability. We did not anticipate that adding a high amount of estrogen to the organoid environment would synergistically augment the inhibitory effect of an IC50 dose of BSHE. As is shown in FIG. 5A, an IC50 dose of BSHE inhibited EC grade 1 and grade 2 organoid viability in a low estrogen environment by about 50%. However, when the same organoids were treated with the same amounts of CE and 100 nM estrogen, organoid viability was at about 25% of the vehicle for both grades of EC. And organoid viability calculated as a % of organoids treated with 100 nM estrogen, was 21% and 23% for grade 1 and grade 2 EC, respectively when treated with an IC50 dose of BSHE and the 100 nM estrogen. Thus, grade 1 and grade 2 endometrial cancer organoids respond to treatment with 100 nM estrogen alone by slightly increasing the percentage of viable cells, but when also treated with an IC50 dose of CE the total percentage of viable cells remaining after treatment is about 25% compared to the control organoids, which is a synergistically better response than with the IC50 dose of CE alone. And when compared to treatment with 100 nM estrogen, organoid viability was decreased by greater than 75%. This is an unexpectedly synergistic effect that at least doubles the efficacy of an IC50 dose of CE.

Increasing the treatment amount of estrogen did not counter the unexpected synergistic effect observed in FIG. 5A. Rather, an even greater synergy was observed. Referring to FIG. 5B, the effects of treating grade 1 and grade 2 endometrial cancer organoids with 400 nM estrogen are shown. Again, when EC grades 1 and 2 were treated with just estrogen, their viability increased when compared to the vehicle. However, when also treated with the IC50 doses of BSHE established for these organoids, organoid viability decreased to 15% and 7% compared to the vehicle respectively for grade 1 and grade 2 EC organoids. Recall that anything less than 10% viability is tantamount to 0% viability due to background interference. When looking at the results as a % of viability when treated with 400 nM estrogen, the decreases in organoid viability were an amazing 113% and 99% for grade 1 and grade 2 EC organoids, respectively. And as compared to the inhibitory effect observed with an IC50 dose BSHE alone, cell viability dropped by 32% and 41%, for grade 1 and grade 2 EC organoids respectively, which is a greater than 50% observed in the 100 nM estrogen environment. Thus, contrary to all expectations, increasing the concentration of estrogen administered to grade 1 and grade 2 organoids from 100 nM to 400 nM resulted in the IC50 dose of BSHE being even further synergistically augmented by the higher concentration of estrogen. This unexpected synergistic effect more than doubles the efficacy of an IC50 dose of CE for the organoids grown in normal media without excess, unopposed estrogen. In fact, this synergy shows about the same and in some cases better reduction than the combination of IC50 values of CE with a chemotherapeutic agent, except, however, in some instances where the chemotherapeutic agent was at the high end of the tested doses.

Thus, FIGS. 5A and 5B show that, as expected, the addition of estrogen alone provided the necessary foundation for growth of the cancer at a significantly higher rate than the control. Indeed, while CE was already shown to be effective in certain cancer treatments, the further refinement of the therapeutic protocol and/or treatments with estrogen further increase the efficacy of the treatment, which is shown to be unexpectedly superior to conventional front line therapies alone. We unexpectedly showed that when endometrial cancer is treated with CE in the presence of a high concentration of estrogen, a highly significant and synergistic response ensued, and that response was, frankly, counterintuitive to any normal/traditional therapeutic system.

The results shown in FIGS. 5A and 5B in combination with our observations in standard growth media indicate that CE may be effectively used in both environments to treat endometrial cancers, especially those that are type I/estrogen sensitive/ER+ such as grade 1 and grade 2 endometrial cancers. Further, the fact that CE efficacy is even greater in the presence of high estrogen than in standard media amounts indicates that CE treatment may prove to be a better first line/adjuvant therapy than anti-hormone treatments such as with progestins, progesterone, estrogen blockers, estrogen modulators, aromatase inhibitors, or combinations of the forgoing. Further, prophylactic use of CEs may even counteract symptoms/conditions arising from unopposed estrogen.

That the results we observed with grade 1 and grade 2 endometrial cancer are extremely surprising is the fact that when we tested a known ER+ ovarian cancer cell line, we obtained the results that we expected with low grade (grades 1 and 2) endometrial cancer. The expected results are shown in FIG. 5C. In this graph, cell viability is plotted as a function of estrogen concentration. The top line depicts cell viability with no estrogen (e.g., the vehicle), when treated with 100 nM estrogen, and when treated with 400 nM estrogen. As expected, viability of these ER+ cells is stimulated when treated with estrogen, where growth is dose dependent. The bottom line depicts cell viability when treated with an IC50 dose of CE alone (e.g., in standard media) and when treated with the IC50 dose of CE in the presence of high estrogen concentrations. The calculated IC50 dose of BSHE was not as robust as expected in this set of experiments, producing a diminished response in that cell viability was at about 74% compared to the control rather than the expected 50% viability. Nonetheless, the inhibition on cell viability observed by treating with CE alone in regular media was even more diminished when also treated with 100 nM estrogen and 400 nM estrogen. Thus, although treating ER+ ovarian cancer cells with an IC50 dose of CE reduced cell viability compared to estrogen-stimulated cell growth, the augmented synergistic response that we observed with low grade endometrial cancer organoids did not occur. Rather, the ovarian cancer cells responded as we expected, where CE treatment in a high estrogen environment diminished cell viability compared to being treated with the concentration of estrogen alone. We did not observe a synergistic inducement when these cells were treated with CE in the presence of high amounts of estrogen.

Accordingly, we successfully determined that CEs are effective in treating all grades EC cancer cells, including grades that are considered estrogen-sensitive/ER+ or estrogen insensitive/ER-. For example, endometrial endometrioid carcinomas are graded by FIGO as follows: grade 1 tumors exhibit <5% solid nonglandular, nonsquamous growth; grade 2 EC tumors show between 6% and 50% of solid nonglandular, nonsquamous growth; and grade 3 tumors exhibit >50% of solid nonglandular, nonsquamous growth. Per our work, regardless of EC grade and ER+ or ER− status, when treating with CE alone the efficacy of each of the materials was statistically insignificant among grades.

Furthermore, we successfully determined that the CEs are effective in treating EC cancers having various mutations and/or fit into one or more molecular groups. For example, the CNH molecular group is associated with TP53 mutations and amplification of ERBB2; the MSI molecular group is associated with PTEN, ARID1A, and PIK3R1 mutations; and the POLE molecular group is associated with POLE mutations. Thus, per known mutations, organoids from grade 2 patients P4, P5, and P7, and grade 3 P12 all had a TP53 mutation, and one or more mutations associated with the MSI molecular group. Only P7, however, had a known POLE mutation. Again, regardless of molecular group, we have shown that CE alone can be used to effectively treat endometrial cancer.

We confirmed our organoid results in mouse models, using patient derived xenografts. The xenograft studies confirm that CE dosing is consistent between organoids and mouse models and that systemic delivery of CE is successful at treating endometrial cancer. EC cells from P6 had ERBB3, PTEN, and TP53 mutations, which further confirms that EC treatment using CEs alone can be used successfully treat all grades and molecular groups of endometrial cancers.

We have also determined that, in complete contradiction to conventional treatment plans, increased estrogen when treating at least type 1, low grade (e.g., grade 1 or grade 2), estrogen sensitive, and/or ER+ endometrial cancers can actually improve the anticancer effects of CE. Because grade 1 and grade 2 organoids were dramatically responsive to CE treatment with increasing (e.g., 100, 400 nM) amounts estrogen, we have shown that CE therapies can lead to superior results when a patient either produces estrogen, is treated with estrogen, or both. Namely, we have shown that CE is effective to treat endometrial cancer in both organoids and in mice. The organoids used in the high estrogen experiments were not distinctively different in their response to CE than those previously tested, which is evidenced by the determined IC50 doses for CE, such as the BSHE used in the experiments, being in line with what we have observed before, including those identified herein. Thus, similar treatment of grade 1 and grade 2 endometrial cancers will align with what we have shown herein. An effective amount of estrogen may be achieved with endogenous estrogens, exogenous estrogens, or a combination of both endogenous and exogenous estrogens. An effective amount of estrogen required to produce a synergistic response (e.g., induced apoptosis, decreased cell viability) with CE treatment depends upon the patient, how much endogenous estrogen the patient is producing, route of administering an exogenous estrogen, other medications/treatments being used at the time. Generally, however, effective amounts of estrogen found in blood levels may be >10 µg/ml, more preferably >30 µg/ml, or >50 µg/ml, >100 µg/ml, >200 µg/ml, >300 µg/ml, >45,000 µg/ml, etc. including >100,000 µg/ml and all increments therebetween. Alternatively, estrogen may be administered either with a CE or separate therefrom. Again, an actual estrogen dose provided to a patient can depend upon various factors, but generally may be achieved by administering current therapeutic amounts of estrogen such as from less than or equal to 0.025 mg/day, 0.3 mg/day, 1.25 mg/day 10 mg/day, 25 mg/day to more than 30 mg/day, and all increments therebetween and without limitation. Of course, an actual effective amount of estrogen for a particular patient may be a combination of endogenous and exogenous estrogens. Furthermore, many women who are not candidates for chemotherapy, surgery, and/or who want to preserve fertility may opt for CE treatment in the presence of estrogen over, or addition to, other available treatments. It should be noted, however, that some anti-estrogen therapies may reduce or block additional beneficial effects of CE treatment in the presence of estrogen, including without limitation, aromatase inhibitors SERDs, SERMs, and the like.

Doses of CE used in our studies can also be converted to determine human equivalents. For example, doses used in organoids can be converted as follows: 1 µg/ml is a dose of approximately 20 mg a day of CBD, 10 µg/ml is approximately 200 mg a day, 25 µg/ml is approximately 500 mg a day, and 50 µg/ml is approximately 1000 mg a day, if provided as a human equivalent dose. Currently, for example, the prescribed CBD isolate is given at a dose of between 5 and 50 mg of CBD/kg and in the United States an average weight of between 65 and 85 kg, yields doses of between 325 to 4250 mg a day of CBD. Our actual tests, therefore, range from well below these doses to about 1% of the currently prescribed dose. We believe that the higher end of the human dosing range is fully appropriate for treating endometrial cancer well, which would replicate tests at 100 µg/ml or higher. This is especially true as the alternative to such higher CBD dose would almost always be chemotherapy, which will have a significantly worse side effect profile at virtually any concentration, than the highest doses of CBD.

Since many receptors and receptor-mediated events include proteins/protein changes and given the widespread presence of the ECS in the mammalian body, and particularly in the reproductive system, we examined the effects of a CE on gynecological cancer cell protein expression. Evaluating protein expression in untreated cells as compared to treated cells provides insight as to which proteins change expression in the endometrial cancer cells and which proteins remain the same. With this knowledge, additional, targeted research may ensue.

Referring to FIG. 6A, endometrial cancer cells (ECC) were either treated with a CE (1 µg/mL) or left untreated as a control (vehicle– DMSO). After treatment, proteins were extracted from the test cells and the control cells and digested for analysis by liquid chromatography (LC) tandem mass spectrometry (MS/MS). Referring to FIG. 6B, the Venn diagram shows the results of LC-MS/MS analysis which is that treated cells expressed 2,842 different proteins than untreated cells, untreated cells expressed 2,681 different proteins than treated cells, and treated and untreated both expressed 3,747 common proteins. Clearly, based on protein expression differences, treatment with as little as 1 µg/mL CE with CBD had a clear impact on proteins that were exclusively expressed and proteins that were no longer expressed. FIG. 6C compares the degree to which certain proteins were expressed (or not expressed) in untreated cells and treated cells.

Referring to FIG. 6D, of the thousands of proteins that were differentially expressed with treated and untreated cells, the top 20 upregulated (e.g., in treated cells only) and downregulated (e.g., in untreated cells only), are identified and enumerated. Now referring to FIG. 6E, the effect of treatment with CE with CBD on signaling and trafficking of various physiological and pathophysiological pathways is shown. As one example, proteins associated with Endocannabinoid Neuronal Synapse are shown to be upregulated in untreated cells and downregulated in treated cells. Interestingly, proteins associated with ER signaling do not show an appreciable difference in expression at this low dose of BSHE.

Figure 6G:
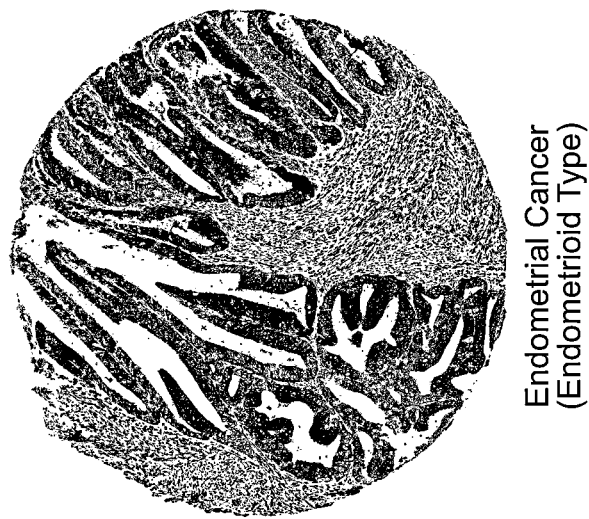
FIGS. 6F and 6G are histological samples from endometrial cancer patients showing cannabinoid receptor 1 protein expression and cannabinoid receptor 2 protein expression, respectively.
Figure 6F:

FIGS. 6F and 6G depict that cannabinoid receptors 1 and 2 have significant overlap with regard to the percentage of patients wherein the receptor is implicated in the cancer. That is, grades 1 and 2 of endometrioid endometrial cancer are associated with excess estrogen, and both CB1 and CB2 receptors are expressed in this cancer. Thus, the interplay between signaling systems in a high estrogen environment may help elucidate a mechanism by which the inhibitory effect of CE is pronounced in estrogen rich environments. That CE-induced apoptosis/decreased cell viability is synergistically augmented in the presence of higher amounts of estrogen may form a significant basis for treating estrogen sensitive disease.

Figure 7A:
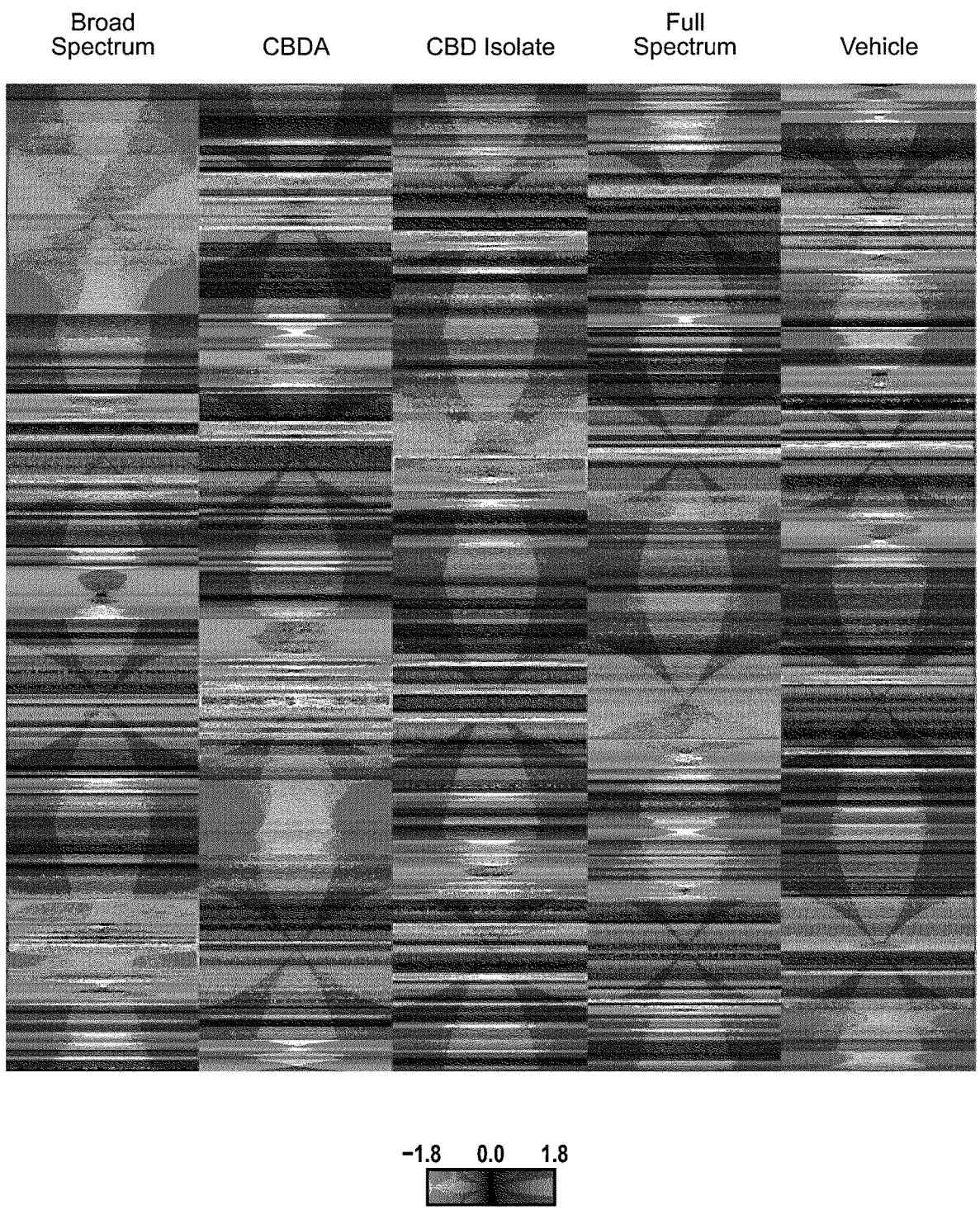
FIGS. 7A through 7F depict various proteomics aspects of grade 1 endometrial cancer organoids treated with IC50 doses of BSHE, FSHE, CBD isolate, and CBDA.
Figure 7B:
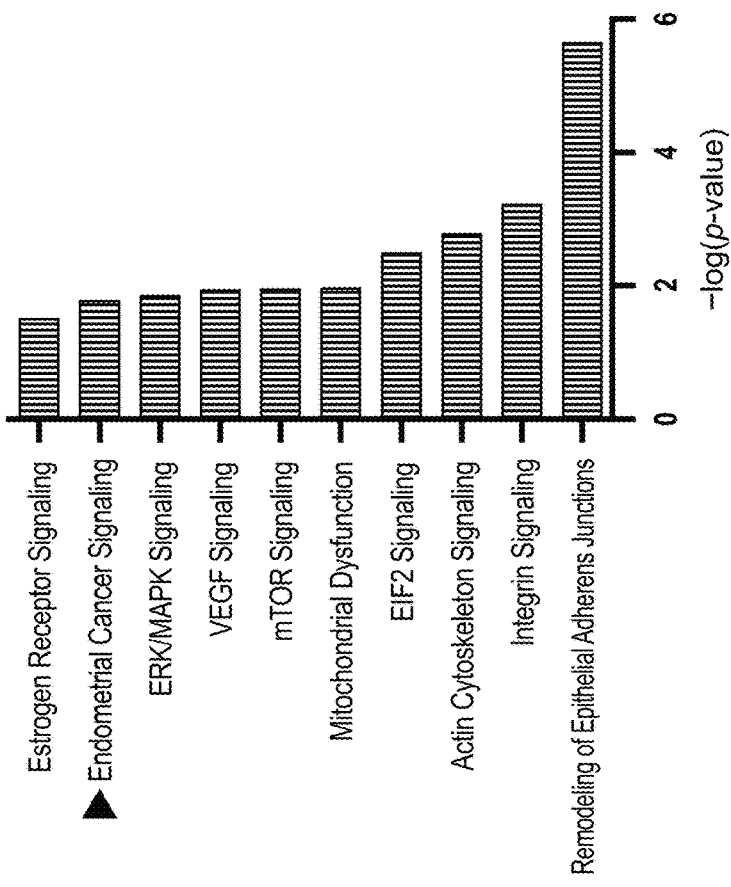
Figure 7C:
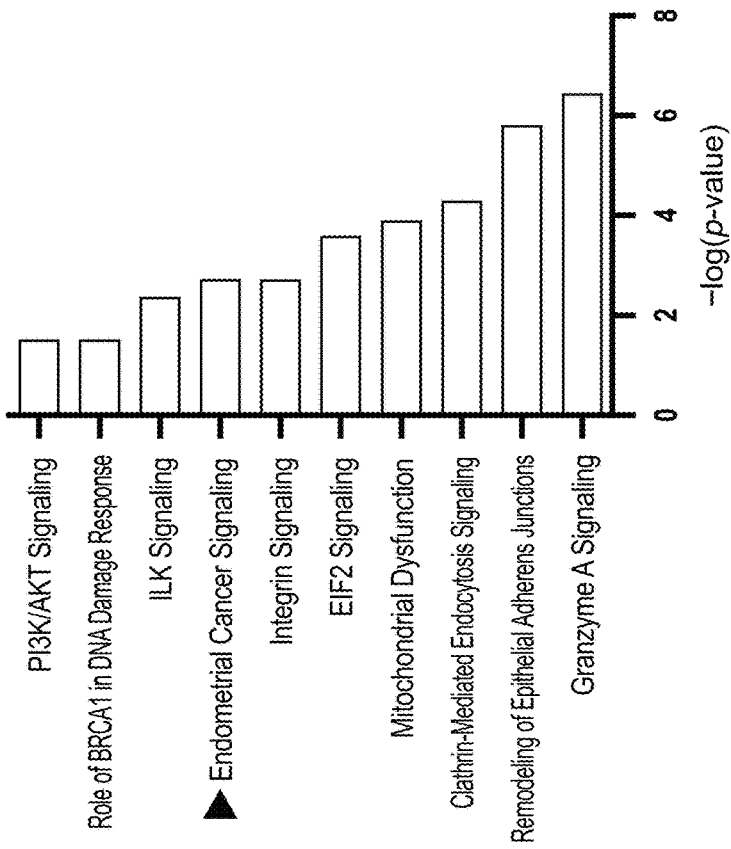
Figure 7D:
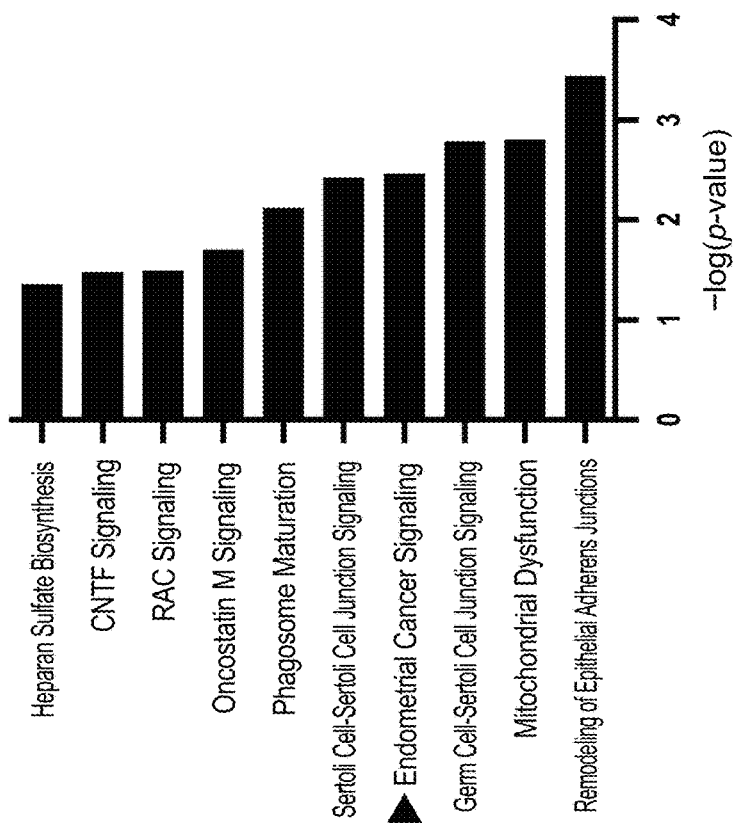
Figure 7E:
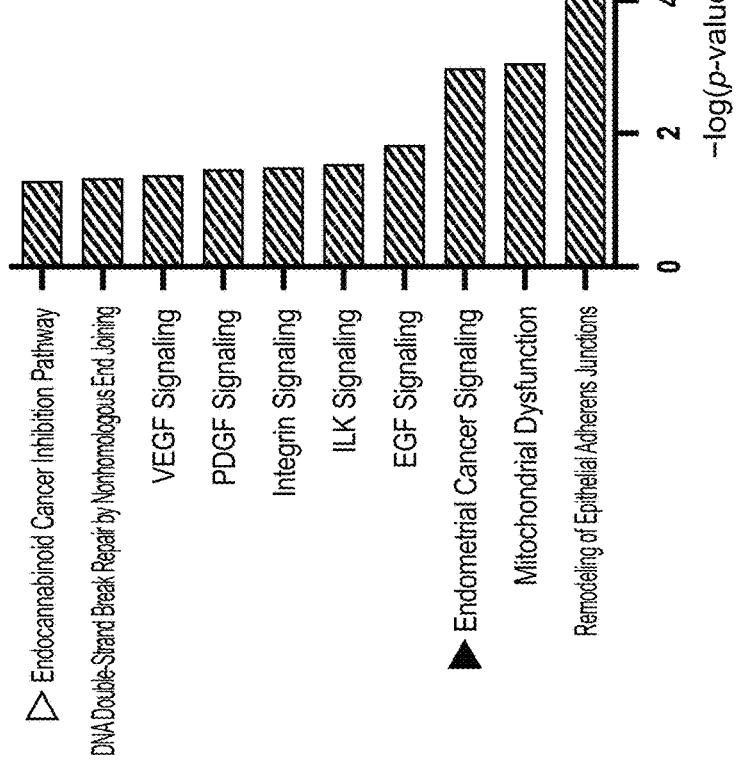

Using essentially the same proteomics methodology described above, we treated organoids from three different patients having grade 1 endometrioid carcinoma with IC50 doses of BSHE, FSHE, CBD isolate, and CBDA, which were calculated for each line of patient-derived organoids. After protein extraction, digestion, and labeling, the peptides were combined and subject to high pH fractionation and mass spectrometry. Results for treatment with IC50 doses of BS, CBDA, CBD isolate and FSHE, and the control are shown in the heatmap of FIG. 7A, from left to right. It is quite interesting that the protein expression profile for each CE treatment is different, which indicates that each CE modulates cellular response in a unique way. The differences in CE protein modulation may account, at least in part, for the varying degrees of induced apoptosis/decreased organoid viability that we have observed with different CE treatments.

We further determined which proteins were upregulated and downregulated in response to each CE IC50 treatment, and then grouped the upregulated proteins by signaling pathway. The results are shown in FIG. 7B through 7E. For each figure, the signaling or other pathway is named on the left and a bar representing the −log(p-value) is to the right. Signaling and other pathways are listed in order of probability from top to bottom, with the bottom pathways having the highest probability. That there is an increase in endometrial cancer signaling for each CE composition supports our observations that the CEs are modifying protein signaling within these cells. Other upregulated signal/other pathways of interest include the Role of BRCA1 in DNA damage response (BSHE), mitochondrial dysfunction and remodeling of epithelial adherens junctions, which are upregulated by all CE treatments. Upregulation of BRCA1 in DNA damage response is of interest at least because of the gene's association of tumor suppression, and the gene product's involvement with genomic stability. Upregulation of proteins associated with mitochondrial dysfunction are also of interest at least due to the role of mitochondria in apoptosis. Remodeling of epithelial adherens junctions in endometrial cancer cells is also of interest at least because these junctions have a special role in assembly/disassembly in uterine epithelial cells, and it will be interesting to find out what role they may have as a result of CE treatment. Thus, we have demonstrated that CE IC50 treatment of endometrial cancer can upregulate proteins associated with endometrial cancer signaling, mitochondrial dysfunction, remodeling of epithelial adherens junctions, among other upregulated proteins. It is believed that at least some of the upregulated proteins, such as those associated with mitochondrial dysfunction, may cause or be the result of apoptosis and/or decrease endometrial cell viability observed with CE treatment thereof. Since estrogen synergistically improves the anticancer effects of CE in certain endometrial cancers, it is believed the same/similar protein upregulation occurs.

Figure 7F:
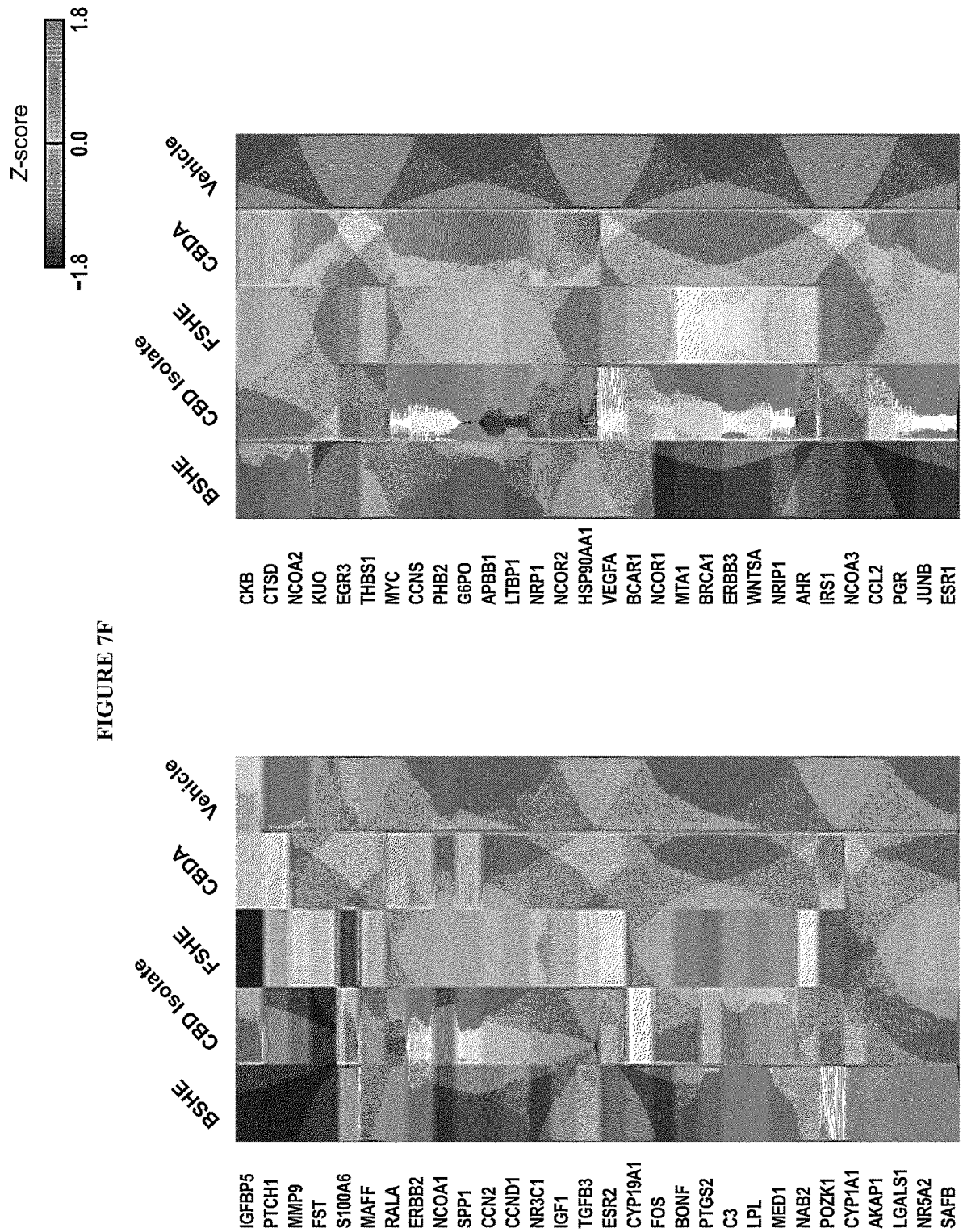
Figure 7G:
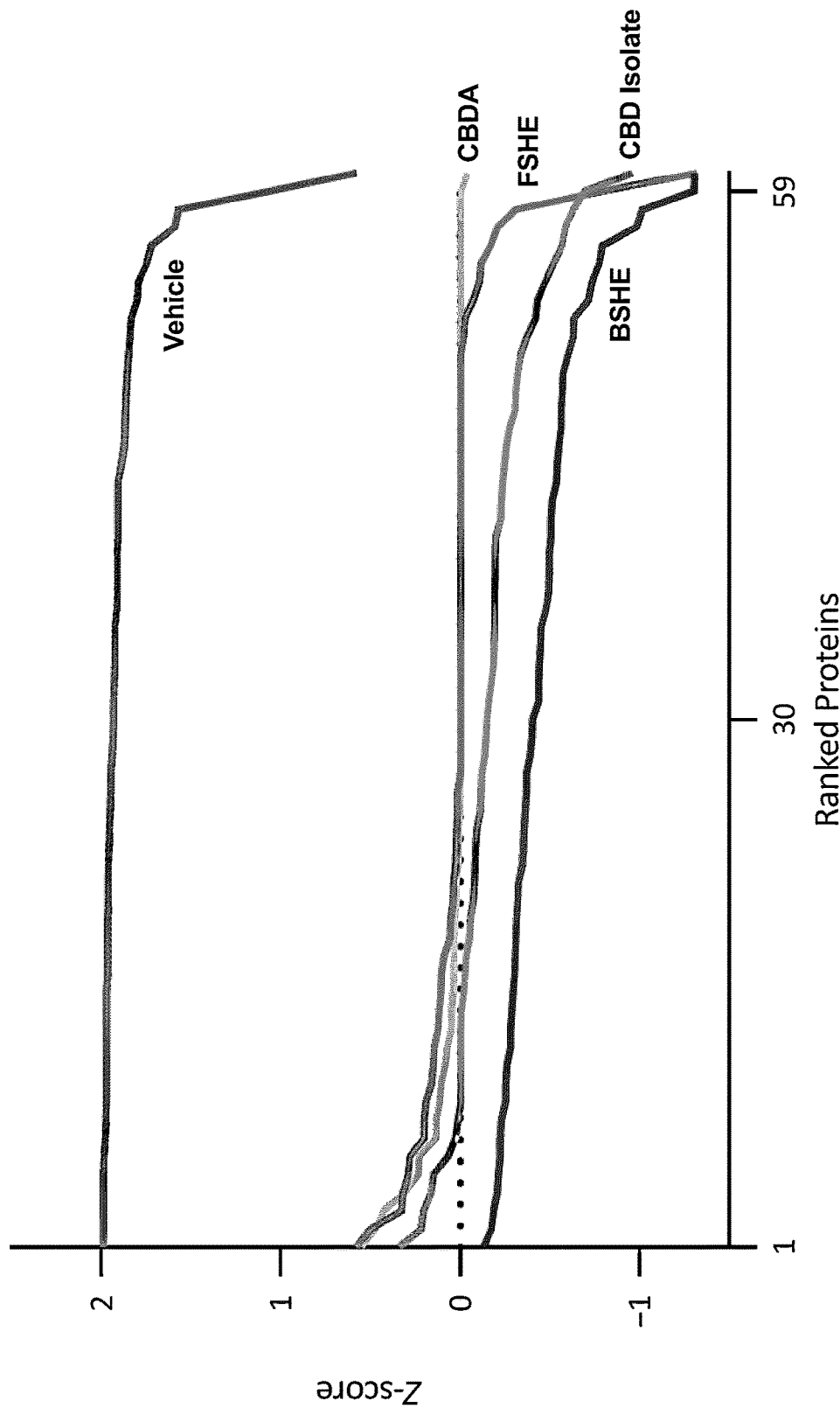
FIG. 7G shows the same as a plot of Z-score (y-axis) against protein (x-axis) from the protein with the highest Z-score to the protein with the lowest Z-score per CE treatment and the control.

In addition to categorizing upregulated proteins by signaling/other pathways, we examined the effects of the various CEs on proteins related to estrogen regulated genes. Interestingly, all proteins examined were downregulated by each CE IC50 treatment compared to the control. Referring to FIG. 7F, the list of estrogen regulated genes examined is to the left of the heatmap, with corresponding protein accumulation being shown to the right of the gene name. Z-scores were determined based on raw MS intensity values processed by Perseus software. Lower Z-scores correspond to downregulated proteins and higher Z-scores correspond to higher protein expression. Z-scores are graphically shown in FIG. 7G, where Z-score is plotted against protein expression. For each CE treatment, the protein with the highest Z-score is ranked as 1 and the protein with the lowest Z-score ranked as 59. Thus, FIGS. 7F and 7G both show that all examined protein products associated with estrogen regulation are dramatically downregulated when treated with an IC50 dose of CE. BSHE was the most effective at downregulating estrogen regulated genes whereas CBDA was the least. Nevertheless, all CE showed a dramatic decrease in protein abundance compared to protein abundance in untreated organoids.

In addition to genomic alterations such as PTEN, ARID1A, PIK3R1, KRAS, and other mutations, excessive estrogen signaling is believed to play a role in endometrial cancer formation. Estrogen signaling involves estrogen acting at ER receptors such as ERα. ERα is expressed in the uterus, ovary, and breast (and other tissues) and its expression is closely associated to cancers in these tissues. ERα activation is known to cause expression of factors such as coded by MYC and IFG1, both of which have oncogenic potential. ERα activation is also known to activate VEGF (vascular endothelial growth factor) transcription; VEGFs are known to be secreted by endometrial tumor cells. Interestingly, endometrial cell expression of proteins associated with the MYC, IFG1, and VEGF are all downregulated when treated with each of BSHE, FSHE, CBD isolate, and CBDA, suggesting that apoptosis/decreased viability induced by CE may be associated with counteracting the effects of ERα deregulation in endometrial, and perhaps other, estrogen-sensitive cancers.

Studies have shown that blocking or countering estrogen in endometrial cancers may be alternatives to other therapies such as chemotherapy and/or radiation therapy. Progestins have been the most widely used to counter the effects of estrogens. Other hormonal treatments include anti-estrogenic drugs such as SERMs, SERDs (down regulators), and aromatase inhibitors. Examples of SERMs and SERDs include, without limitation, tamoxifen, fulvestrant, raloxifene, and arzoxifene. Aromatase inhibitors include anastrozole, letrozole, and exemestane. When used alone, some of the aforementioned anti-estrogenic drugs produced a modest response in women with endometrial cancer accompanied by side effects such as thrombosis and nausea. Further, none of ER− patients seemed to respond to the anti-estrogenic drugs. Here, we have established that CEs are effective in treating all grades and various molecular types of endometrial cancers, regardless of ER status. We have also established that excess and/or unopposed estrogen actually increases the anti-cancer effects of the CE, thereby making it a superior choice for endometrial cancer treatment. As CEs have been demonstrated to alter protein expression in endometrial cancer, including downregulation of proteins associated with excess estrogen-mediated effects, it is believed that the downregulation of at least some of these proteins may lead to increased apoptosis/decreased cell viability. Treating endometrial cancer cells in the presence of higher amounts of estrogen may enhance the downregulatory effects of CEs at least in part to contribute to synergy observed with CE treatment.

Our experimental results are supported by observations in human patients. For instance, a 31-year old patient, suffering from metastatic, chemoresistant endometrial cancer, came to us for help. She had already underwent a total hysterectomy with bilateral salpingo-oophorectory followed by five rounds of chemotherapy with paclitaxel/carboplatin followed by Abemaciclib and then Atezolizumab. Organoids grown from her cancer were responsive to CE and partially responsive to gemcitabine/capecitabine (GemCap) in combination. After treatment with GemCap and with both oral mucosal and intravaginal CEs comprising CBD at about 130-135 mg/day, patient scans revealed a complete metabolic response to treatment. Notably, previously demonstrated metastatic lymph nodes, pulmonary metastases and peritoneal disease were barely perceptible on CT with complete metabolic response. Malignant ascites were nearly completely resolved and no new hypermetabolic disease. However, while the patient remained in cancer remission, she had significant damage to her organs from the several rounds of chemotherapy and she died from complications from the organ damage from chemotherapy, with an absence of cancerous growths at the time of death. Accordingly, even though the combined therapy of chemotherapy and *cannabis* extract proved to be highly effective in reducing this patient's tumor growth, pre-existing damage from the numerous rounds of chemotherapy proved to be fatal. There is no telling whether she could have achieved earlier remission and prevented extensive organ damage due to numerous unsuccessful rounds of chemotherapy, had she utilized CE treatment alone or in combination earlier rounds of chemotherapy. Nonetheless, this patient's last treatment of combined therapy with chemotherapy and CE having CBD proved to be effective.

To our knowledge, it has not been previously shown that therapeutic amounts of CE comprising CBD could be used to treat metastatic endometrial cancerous growths in a human patient. Based on our findings detailed above (e.g., FIGS. 1-7), we believe that treatment with oral, oral mucosal, and intravaginal application of CE such as BSHE and/or FSHE selectively reduced tumor size in this patient by inducing apoptosis/decreasing endometrial cancer cell growth. This is supported by the fact that in-patient treatment effectively reduced the prevalence of endometrial cancer, which had spread throughout the body. Administering intravaginal and oral mucosal CE comprising CBD showed a reduced sized/absent metastatic nodes having immeasurable metabolic activity. That is, metabolic activity is indicative of cancer cell viability, which was no longer measurable in the patient such as by PET, CT, or FDG-PET. Accordingly, an embodiment of a method of treating an endometrial cancer comprises administering to a patient in need thereof, an effective amount of a *cannabis* extract comprising CBD at a dose of between 5 mg to 5000 mg a day, wherein the dose is given via an oral, mucosal—such as intravaginal, oral mucosal, or other mucosa, dermally, or another form or combinations thereof. Furthermore, treatment can be repeated several times a day, wherein a total dose of CE/CBD may be between 50 and 500 mg a day. In preferred embodiments, a dose of between 25 and 250 mg of CBD from a FSHE or BSHE is given at least once a day. In a preferred embodiment, the FSHE or BSHE comprises a fat, oil, or other carrier for intravaginal application, and further comprises at least one terpene.

A similar response to treatment with CE was found with a patient having head and neck cancer. This patient had significant mucous formation in his throat, was not eating, and felt full all the time, probably due to the excessive mucous secretion by the cancer cells. The patient was diagnosed with esophageal adenocarcinoma signet ring type at GE junction. At the time of presentation, the esophageal cancer patient declined chemotherapy, resection surgery, and radiation therapy. Because of prior success with CE as a cancer treatment, it was suggested to the patient to take an oral mucosal/sublingual dose of a CE. This patient chose FSHE as the CE of choice taking between 80 and 120 mg a day. After three weeks of treatment, the patient reported that he was now able to eat and to resume normal life activities. Thereafter, patient maintained treatment with FSHE and was in remission for at least 12 months. We have not had an update on this patient's progress since then. Since this patient continued CE treatment (e.g., as FSHE) at the prescribed dose into and during remission (for the duration of the treatment), it may be suitable to maintain the CE administration for both the initial cancer treatment and also to maintain therapeutic efficacy over the cancerous growths.

Given the success of endometrial cancer organoid treatment with CE, and the successes with the two cancer patients, we investigated the efficacy of various forms of CE in combination with a chemotherapeutic agent. This is especially important as a first line/adjuvant therapies for estrogen sensitive cancers can be chemotherapy. It is well known that chemotherapy agents are highly toxic and even under the best circumstances, patients tend to have difficulty tolerating them. Moreover, chemotherapy is often given in progressive doses, meaning, as the disease progresses, more/higher doses of the chemotherapy drug may have to be given to the patient to obtain the same inhibitory response. In many cases, cancers become "chemoresistant" in that the cancer cells persist/grow despite the chemotherapy—even if the chemotherapy worked before. As such, we tested the combination of chemotherapy drugs with a *cannabis* extract to determine if the combination could reduce the amount of chemotherapy required to obtain therapeutic responses, namely reducing the growth of endometrial cancer tumors, and ultimately eradicating the tumors. We tested the combined treatment for efficacy in both patient derived organoids and mice models. Among these, applicant has further identified methods of treatment of estrogen-mediated cancers through administration of *cannabis* extracts and concurrently administering therapeutic molecules, such as a chemotherapeutic agent, to increase effectiveness of the chemotherapeutic agent.

A key metric in these experiments is to determine if we could generate an equivalent clinical response to the chemotherapy, while using a lower total amount of the chemotherapeutic agent. As a simplified example, a normal dose of chemotherapy agent X is 200 mg, resulting in a reduction of tumor size by 90%. If chemotherapy agent X is given at a dose of 100 mg and an IC50 dose of a CE is also given, will the tumor size also decrease size by 90%? In other words, can the two agents be used together to obtain the same or better result? If yes the patient could benefit from the dual treatment because, in addition to treatment effects on the tumor, secondary damage to healthy tissue and other known adverse impacts from the chemotherapeutic agent could be reduced. The results from our experiments show that by using an amount six times less than the normal chemotherapy dose (not just a 50% reduction), combined with an IC50 dose of a *cannabis* extract produces a therapeutic response that arrested tumor growth. In fact, the combined treatment of a chemo agent and an IC50 dose of CE was able to decrease endometrial cancer organoid viability and tumor volume in mice models.

Figure 8A:
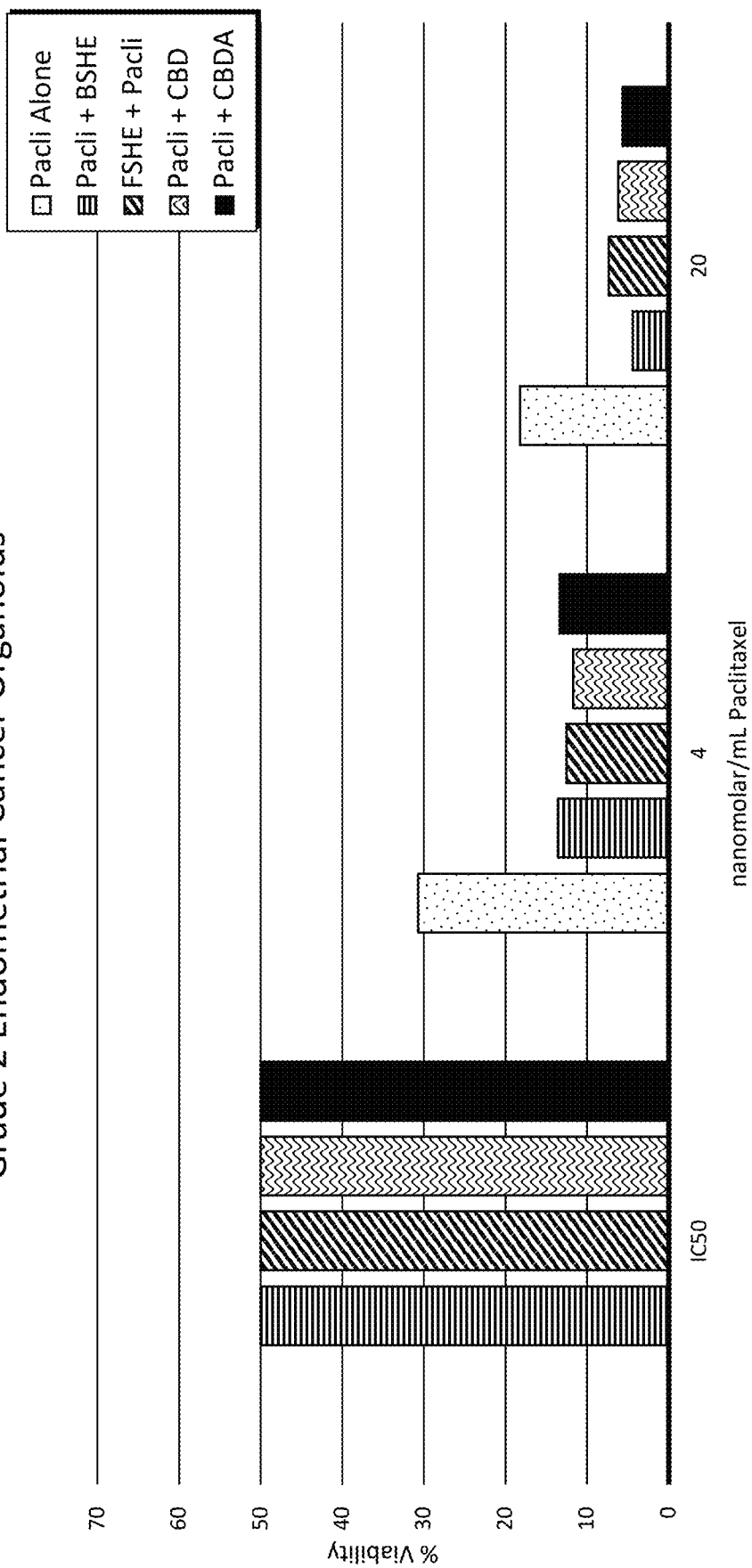

FIGS. 8A and 8B detail the effects of IC50 does of various CE alone and in combination with two different chemotherapeutic agents on grade 2 endometrial cancer organoids. FIG. 8A shows the effects of IC50 doses of BSHE, FSHE, CBD, and CBDA, alone and in combination with 4 nM/mL and 20 nM/mL of paclitaxel; FIG. 8B shows the same (except CBDA) in combination with 50 µM/mL, 100 µM/mL, and 250 µM/mL of carboplatin. The IC50 doses for the CEs on the organoids tested are about 1 µg/ml for the BSHE, 4 ug/ml for the FSHE, 3 µg/ml for CBD isolate and 12 µg/ml for the CBDA. Although not shown, paclitaxel was also tested at 8, 12, and 16 nM/ml, with only moderate changes in a linear fashion. Results shown in FIGS. 8A and 8B have been normalized against respective IC50 results.

What is striking about the results of FIG. 8A, is that taking the first dose of paclitaxel and increasing that dose by 5X, results in a relative reduction in viability of about 12% for the organoids. However, in view of the significant toxicity, such minimal gains, and a large multiplier of the dose, shows the weakness of the paclitaxel alone. The gains pale in comparison to what is evident from using the lowest dose of paclitaxel, with an IC50 dose of any of the *cannabis* extracts, reducing the viability by nearly 20% across all tests. Thus, it would be more advantageous to administer the lowest dose of paclitaxel with a dose of *cannabis* extract instead of increasing the dose of the paclitaxel. Accordingly, by taking an IC50 dose of any of the *cannabis* extracts and administering it concurrently with the paclitaxel, a surprising synergy was identified, which could dramatically reduce the amount of paclitaxel needed to achieve low to no viability for the endometrial cancer organoids.

As is shown in FIG. 8B, results with grade 2 endometrial cancer organoids treated with carboplatin generally follow the paclitaxel data. Indeed, carboplatin has a viability at 50 um/ml of only about 50%, virtually equivalent to the IC50 doses for CE. However, by combining the carboplatin with the *cannabis* extracts, a synergistic effect is seen, where at any dose, the combined effects are superior to either alone. The results for FSHE are particularly noteworthy at the lowest dose of carboplatin, yet each of the BSHE, FSHE, and the CBD isolate show virtually 0% organoid viability with the higher doses of carboplatin. By comparison, the carboplatin alone diminishes from about 50% viability at the lowest dose to about 32% viability for the highest dose. Again, by increasing the chemotherapeutic drug by 5X, a relative improvement of only about 18% is found. However, adding the lowest dose of carboplatin with an IC50 of CE yields the same or better result. Thus, the combined therapeutic is surprisingly much more effective than either alone.

Figure 8C:
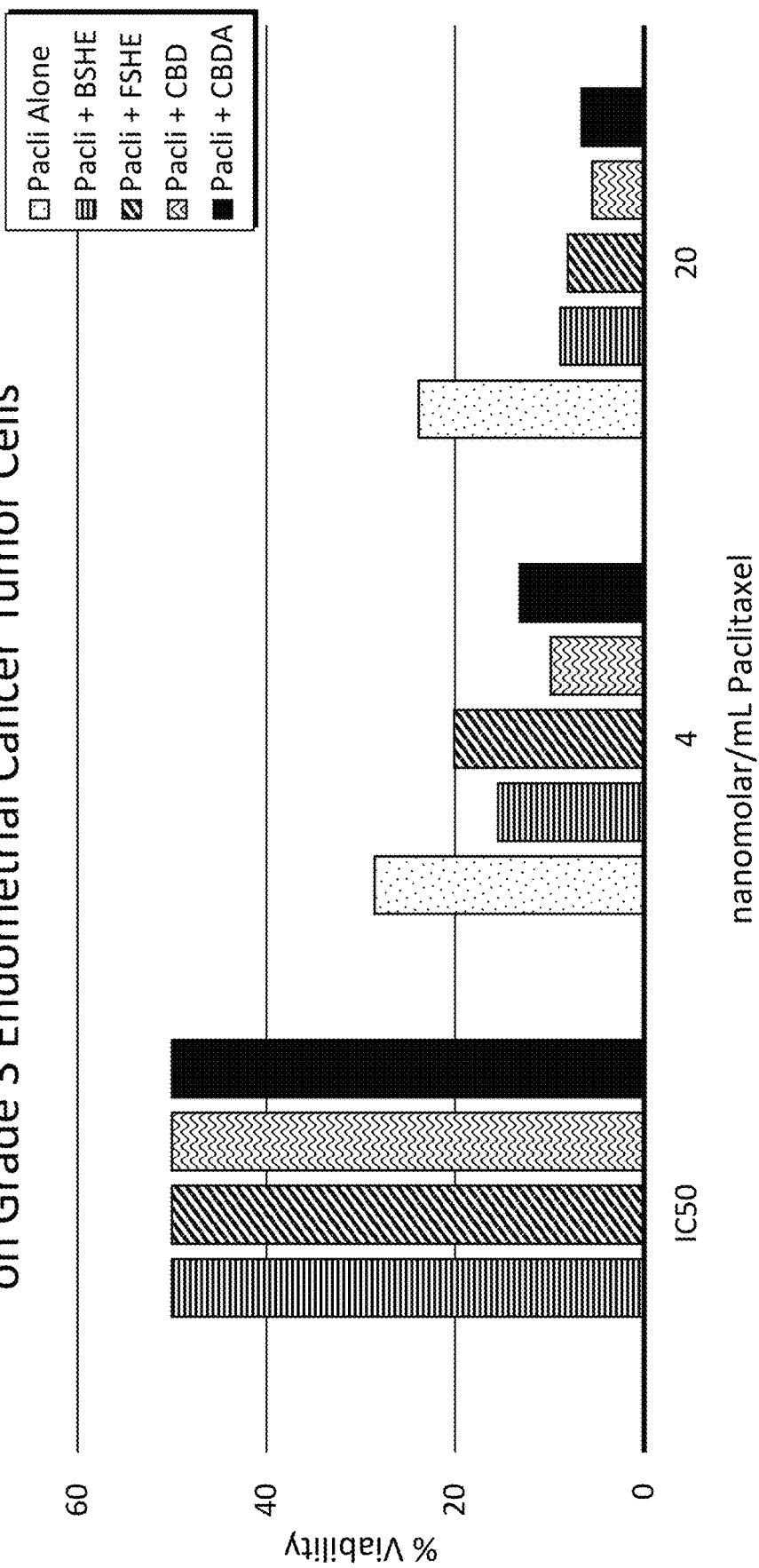

FIG. 8C shows the response of grade 3 endometrial cancer organoids to IC50 doses of various CE alone and in combination with paclitaxel at 4 nM/mL and 10 nM/mL. Approximate IC50 doses for the various CE are 6 µg/ml for BSHE, 4 µg/ml for FSHE, 3 µg/ml for CBD isolate, and 16 µg/ml for CBDA. If anything, the grade 3 endometrial organoids were somewhat less responsive than the grade 2 endometrial organoids. Nevertheless, in the presence of a CE, organoid viability was diminished by at least 6% and up to 20% when compared to treating with 4 nM/mL paclitaxel alone and by about 15% to 18% when compared to treating with 20 nM/mL paclitaxel alone. Thus, the same synergy between a chemotherapeutic agent and a CE was observed in grade 3 endometrial cancer organoids.

Thus, when looking at organoid examples, the addition of the *cannabis* extract with a chemotherapy agent provides for a dramatic reduction in the number of organoids when combined with paclitaxel or carboplatin. Accordingly, based on this result, a patient could take a greatly reduced amount of either of the chemotherapy drugs, combined with an effective amount of the *cannabis* extract comprising CBD to obtain a similar decrease in endometrial cancer viability, and even shows a much greater impact and higher rate of apoptosis than taking the chemotherapy agent alone, even at the highest effective doses. Furthermore, by testing the most common chemotherapy drugs utilized for EC, one being a plant based alkaloid and the other a platinum-based, we know that the results are translatable across different chemotherapeutic agents that function in different ways from one another.

To confirm the efficacy of this mode (i.e., CE+ chemo agent), mice were then grown with grade 2 endometrial tumor cells and treated with either a control vehicle, a chemotherapeutic agent alone, or a combination of the chemotherapeutic drug (paclitaxel) and the *cannabis* extract together. For the mice studies, the mice were given paclitaxel at 10 mg/kg body weight. This relates to a clinical dose of only 30 mg/m$^2$, which is dramatically lower than the 175 mg/m$^2$ that is given to human patients. Mice given any of the *cannabis* extracts were administered as detailed below, with a dose of 30 mg/kg body weight.

FIG. 8D details the results of mice tumor volume comparing paclitaxel alone to those treated with a combined paclitaxel and a *cannabis* extract. The control, or no treatment is not shown in FIG. 8, but results in more than 100% growth over the 21 days, as compared to the initial tumor volume. What is striking is what was seen in the organoid data and is then repeated here. Combining a low dose of paclitaxel with an effective dose of any of the *cannabis* extracts yields dramatically greater reduction in tumor volume as compared to the paclitaxel alone or even the *cannabis* extracts alone at the given dose. Thus, co-administering a *cannabis* extract with carboplatin or with paclitaxel was surprisingly more effective than their administration alone.

After the mice were treated, mice were sacrificed and histopathology taken from the mice models show that treating the mice with *cannabis* extracts does not damage the cells of the ovary, fallopian tube, the uterus, vagina, or the liver. This is critically important, as treatment with high doses of chemotherapy are indiscriminate and damage these cells, when given over time. Thus, reduction in the quantity of chemotherapy drugs, whether at lower doses or none, in combination with the *cannabis* extract can improve the outcome for patients by decreasing tumor volume at a greater rate, reducing the tumor volume to a greater total percentage than chemotherapy alone, and does not otherwise cause damage to the corresponding, healthy tissues of the reproductive tract and the liver as would occur from chemotherapy use.

Notably, grade 2 based cells are typically ER+ and sensitive to estrogen whereas grade 3 cells are not. Thus, in the existing studies, CE alone, or CE in combination with a chemotherapeutic agent was effective in treating estrogen sensitive cancers and those that are not sensitive to estrogen in a standard estrogen environment (e.g., what is present in standard media or what was being produced naturally by the mice). That is, except where specifically noted existing ERs were not modified, blocked, or provided with additional estrogen, again confirming that the impacts on the cancer treatments on the cancerous cells is not modified based on whether the cancer is ER+.

However, with increasing amounts of estrogen, grades 1 and 2 endometrial cancer cells were more responsive to CE treatment than was observed with standard amounts of estrogen. Increased amounts of estrogen in the endometrial cancer organoid model synergistically increased apoptosis, which was a complete surprise. The surprising nature of the CE in conjunction with increased estrogen synergy was supported by the discovery that ER+ ovarian cancer cells (i.e., PEO1 cell line) did not respond with the same synergistic effect of augmented apoptosis/decreased viability. Thus, tumor origin (e.g., ovarian vs. endometrial) and/or other factors (grade, stage, chemosensitivity, chemoresistance, etc.) may affect the appropriateness/outcome of CE treatment in the presence of high estrogen.

Additionally, by jointly administering a chemotherapeutic agent with a CE (with or without increased estrogen), would allow for at least two different paradigms. First, a standard dose of chemotherapy could be used and also treatment with CE. Preferably, the CE comprises between 20 and 4250 mg of CBD. This first dose (and subsequent doses to finish a chemotherapy cycle) would allow for an improved rate of kill of the cancerous cells, as compared to the chemotherapy alone, and thus improve the clinical treatment by removing or killing more cancerous cells, with the goal of killing all of the cancerous cells. This would then allow for a reduction in the number of chemotherapy rounds—where without the CE, a typical patient might undergo 2, 3, 4 or more rounds, preferably, the combined treatment with chemotherapeutic agent and CE would allow for a reduced number of chemotherapy rounds to eradicate the cancerous tissues.

In a second paradigm, instead of requiring a full, standard dose of chemotherapeutic agent, a reduced dose can be provided. For example, the data herein show that a 5× or 6× less dose of the chemotherapeutic agent was less effective than simply combining a lowest dose with a CE. Accordingly, a standard dose of chemotherapeutic agent could be determined and then reduced by 10%, 20%, 30%, 40%, 50%, 60%, 70%, etc. so long as combined with an effective amount of the CE. The results in all cases showed that this lower dose with the CE was more effective than the chemotherapeutic dose at the 5× or 6× alone. Accordingly, because of the known toxicity of the chemotherapeutic agent, this reduced chemotherapy amount, when combined with the CE could help to reduce the secondary tissue damages and toxicity to patients who are administered chemotherapy for cancer treatment. These two paradigms would be effective irrespective of the cancer genotype of ER+ or ER− and/or estrogen sensitivity, would be successful as a front line therapy or as an adjuvant to existing front line therapies. When compared, side-by-side, to know toxic drugs, including paclitaxel and carboplatin, our results are pretty striking. The use of CE as a treatment, whether alone or in combination with the chemotherapy agents is significant in treating all grades/types/stages of endometrial cancer.

Another paradigm includes treating estrogen sensitive endometrial cancer with CE in conjunction with an increased amount of estrogen (whether endogenous, exogenous, or a combination of the two), above serum levels of about 30 μg/ml, 100 μg/ml, and even about 300 μg/ml or more. Furthermore, increased amounts of estrogen and concomitant CE treatment may also be combined with a chemotherapeutic agent to increase efficacy of the chemotherapeutic agent. Comparing the estrogen+CE treatment to the CE treatment alone, or even chemo with CE showed significant changes in induced apoptosis/cell viability. Namely, unexpectedly, the presence of elevated estrogen actually increased the organoid kill rate, which was accelerated at an even higher estrogen dose. This would be in direct conflict to typical treatment plans, and which were shown without the CBD, that higher amounts of estrogen are effective in proliferating susceptible cancer cell growth. We are challenging that paradigm and have unexpectedly identified that treatments with CE for certain ER+/estrogen sensitive cancers, in the presence of estrogen or an estrogen agonist, and/or further in combination with a chemotherapeutic agent, provide dramatic improvements in the efficacy of the treatments, which is completely counterintuitive to current therapeutic dosing strategies.

Figure 9:
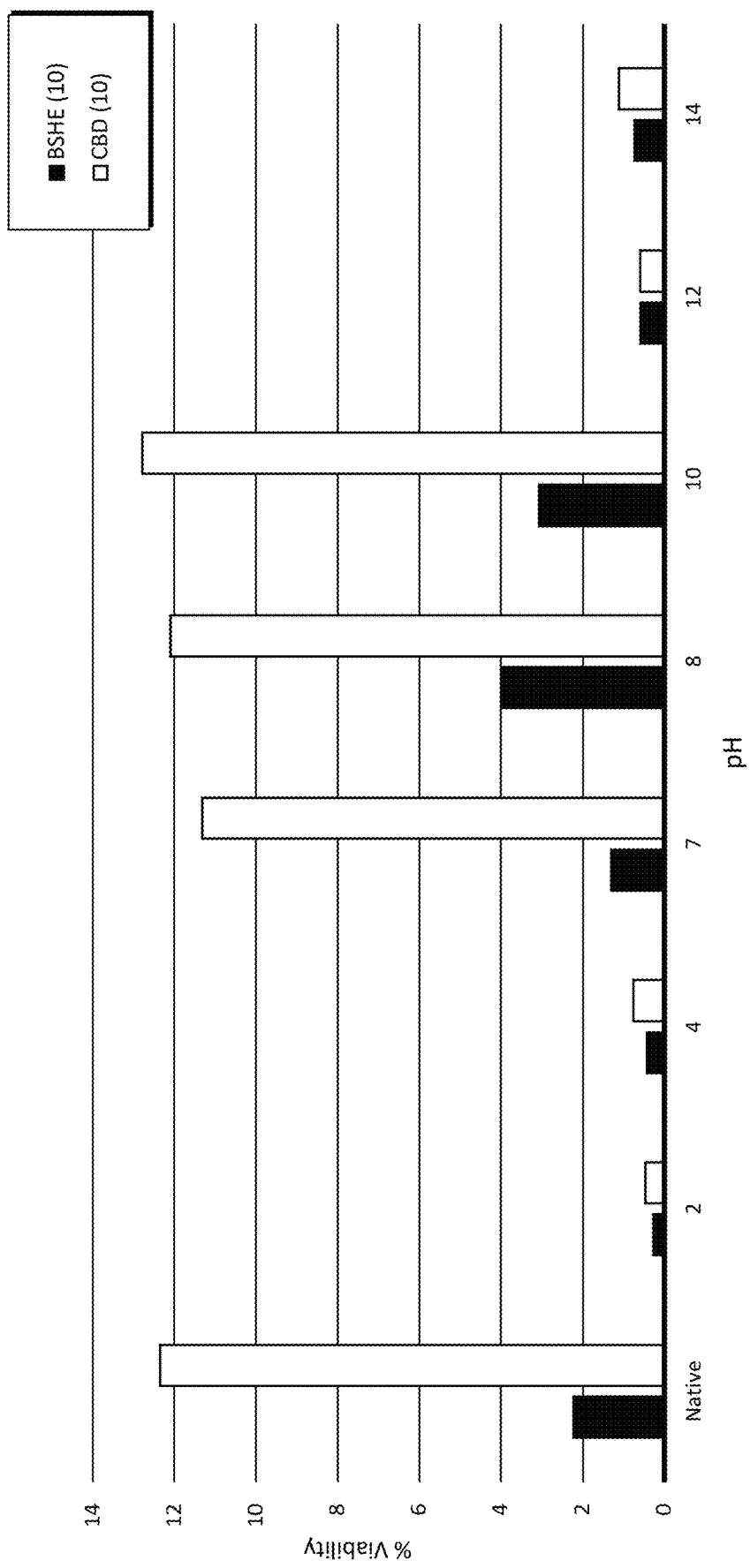
FIG. 9 depicts a chart showing the impacts of pH on therapeutic efficacy of the *cannabis* extracts.

A further interesting observation was determined by the impacts of pH on the efficacy of the *cannabis* extract on organoid viability. FIG. 9 shows that the native pH of the *cannabis* extracts provided for an approximately 2 or 12% viability for the organoids. However, increasing the pH led to substantial improvements in efficacy. However, a pH of 12 and certainly of 14 are highly corrosive, alkaline concentrations and are not suitable for therapeutic use. Indeed, such a pH would not be isotonic, nor would it be appropriate for intravaginal application. The vagina has an acidic pH, which is necessary to maintain the balance of bacteria. However, strong modifications of the pH may lead to denaturing of the proteins or other problems. What was immediately evident is that the first attempts to buffer, even slightly, the pH to be more acidic, yielded worse results. Indeed, each of the two *cannabis* extract materials had less efficacy by decreasing pH from 10.5 to pH of about 10. Furthermore, reducing the pH further to 8, again made the BSHE almost twice as weak at killing the organoids as the native pH, while the CBD isolate shows virtually no change. Even at pH of 7, a neutral pH, the changes are minimal at best.

In such a situation, decreasing the pH further would not likely lead to any further gains for therapeutic efficacy, as the changes were typically worse or virtually no change as compared to native pH. Instead, by further decreasing the pH to 4, a dramatic improvement in the % viability was seen for each of the BSHE and the CBD isolate, such that each were under a 1% viability, such result was unexpected based on the prior data trending toward a worse response or virtually unchanged response. Accordingly, when providing the *cannabis* extract, especially where the *cannabis* extract is provided intravaginally or oral mucosally, utilizing a buffer to modify pH to between 2 and 6, yields a superior response than giving the *cannabis* extract at its native pH. Preferably, the *cannabis* extract is provided in a carrier with a pH of between 3.5 and 5.5, and more preferably at between a pH of between 4 and 5.

We have identified that administering therapeutically effective doses of *cannabis* extracts (CE) are effective in treating gynecological cancers such as endometrial cancer. Most surprisingly, CE is effective in treating estrogen sensitive endometrial cancer when accompanied by higher than average amounts of estrogen. CE is also effective in treating estrogen sensitive endometrial cancer in combination with chemotherapeutics such as paclitaxel or carboplatin. In preferred embodiments, the CE comprises between about 50% to 100% by weight CBD and is provided in a composition, with the CE forming between 10 and 100% of the total weight of the composition. As one nonlimiting example, a 10 mg dose of BSHE or FSHE comprises between 5 to 9.9 mg of CBD, which can then be added to a carrier to form the composition or provided in a raw form as an oil/extract. The remaining components of the BSHE or FSHE comprise additional cannabinoids, terpenes, polyphenols, essential fatty acids, and phytonutrients. When provided in a pharmaceutical composition, the concentration of CBD is typically between 5 and 50 mg/mL of a pharmaceutical composition, however the concentration is not limiting. Certain compositions comprise additional excipients and ingredients, including but not limited to one or more of a fat, an oil, MCT oil, long chain triglyceride oils, or very long chain triglyceride oils. Terpene components including but not limited to β-myrcene, β-caryophyllene, linalool, apinene, citral, D-Limonene, Eucalyptol. Polyphenols may include, but are not limited to catechins, quercetin, cannflavin A/B/C, rutin, and chlorogenic acid. Omega 3, omega 6, and omega 9 fatty acids may be present, as well as additional phytonutrients such as sterols, carotene, aliphatic alcohols, and certain minerals. These components, including the carrier may make up to 90% by weight of the pharmaceutical composition, however, more preferably CBD comprises between 1 and 99.9% by weight of the pharmaceutical composition.

In view of the therapeutic efficacy of adding estrogen in certain applications, the composition may further comprise an exogenous estrogen or an estrogen receptor agonist. However, the administration may also be a first composition comprising the CBD and a second composition comprising the estrogen, estrogen receptor agonist, or a prodrug thereof. Estrogen dosing can depend on the type of estrogen, the route of administration, or both. Generally, estrogen doses may be from about 0.025 mg to 25 mg one or more times a day for the duration of the treatment. Exact dosages will depend upon the amount of endogenous estrogen being produced by the subject, if any, and any other medications that the subject may be taking. Routes of administration may be oral, dermal, transdermal, intravaginal, injection (intravenous, intramuscular) and mucosal, without limitation. In an embodiment estrogen may be administered as part a CE composition or treatment or separate therefrom.

Therefore, a preferred embodiment is related to a method of treatment of estrogen sensitive cancer such as type 1, grade 1, or grade 2 endometrial cancer comprising, administering to a patient an effective amount of a pharmaceutically acceptably composition comprising a CE having between 50 and 100% by weight CBD, wherein the CE is one of a BSHE, a FSHE, a CBD isolate, or CBDA. In preferred embodiments, an effective amount is one effective to generate an equivalent concentration of at least 10 μg/mL of the BSHE, FSHE, CBD isolate, or CBDA at the target tissue. In a further preferred embodiment, an effective dose is between 10 and 2500 mg a day of CBD, wherein said CBD is provided in the CE through an intravaginal application, oral application, oral mucosal application, or combinations thereof. In embodiments, the effect dose of CE is administered to a patient producing an effective amount of endogenous estrogen such as serum levels above about 30 μg/ml, or more preferably above 300 μg/ml. In other embodiments, the effective dose of CE may be administered to a patient being treated with an exogenous estrogen at from about 0.025 mg to about 25 mg at least one time per day. In an embodiment, the subject may produce a less than optimal amount of endogenous estrogen, which can be supplemented with an appropriate amount of exogenous estrogen.

In a further preferred embodiment, a method of treatment of estrogen sensitive cancer comprises administering to a patient an effective amount of CBD from a BSHE or FSHE. In preferred embodiments, an effective dose is one effective to generate a concentration of at least 10 μg/mL of BSHE or FSHE at the target tissue. In a further preferred embodiment, an effective dose is between 25 and 2500 mg of CBD, wherein said CBD is provided in a *cannabis* extract, and delivered through an intravaginal application. In certain embodiments, a patient is first tested for chemoresistance to their particular cancer, and upon confirmation of chemoresistance, treating with the effective amount of CBD from a *cannabis* extract. In certain embodiments the patient may also be treated with an effective amount of exogenous estrogen from about 0.25 mg to about 25 mg at least one time per day as part of a combined therapy with an effective amount of CE, chemotherapy, radiation treatment or combinations thereof. Such therapeutic coadministration may be suitable for increasing chemotherapeutic/radiation efficacy and/or decreasing the dose thereof and thus toxicity related to chemotherapeutic or radiation treatment.

In a further embodiment, a patient may be first tested for estrogen sensitivity, wherein a determination is made as to whether the patient has estrogen sensitive endometrial cancer. In a further embodiment, a patient may be tested for estrogen sensitivity and/or ER(+) endometrial cancer. Upon a confirmation of estrogen sensitivity or ER(+) grade 1 or 2 endometrial cancer, the method comprises administering to a patient an effective amount of an exogenous estrogen and concomitantly administering to said patient an effective amount of a CE.

In an embodiment the pH of a CE and/or composition comprising a CE may be adjusted to that of about 2 to about 6. Adjusting the pH has been demonstrated to increase efficacy of the CE. Thus, where appropriate, a preferred embodiment, the pH of the CE and/or composition including CE is less than a native pH.

We have also shown that gynecological tissues can be targeted by certain applications of CE, whether through oral, oral mucosal, vaginal mucosal, or other administration to treat EC and reduce tumor size. Because of the targeted approach toward gynecological tissues, those of ordinary skill in the art will recognize that certain therapeutics are able to pass through the vaginal mucosa and contact tissues both on the vaginal wall, but also tissues adjacent to the vaginal wall, including the entirety of the gynecological tract, including the uterus, cervix, ovaries, etc., as nonlimiting tissues. Indeed, while these tissues are generally connected, application into the vagina does not always ensure that a therapeutic will also travel to and impact the uterus or ovaries. However, there is an abundance of endocannabinoid receptors in the female reproductive tract to allow for possible therapeutic impact of administered cannabinoids to such tissues, as is demonstrated in FIGS. 6F and 6G. Furthermore, intervaginal delivery of cannabinoids may result in uptake via the inguinal lymph nodes, leading to additional systemic uptake from the reproductive tract.

Intravaginal delivery is well studied and considered safe, effective, and well tolerated. Intravaginal delivery avoids gastrointestinal absorption and bypasses first pass metabolism, while facilitating a localized effect and a steady, sustained therapeutic response. Absorption and systemic delivery via vaginal epithelium occurs rapidly with similar lipophilic compounds. Variances in thickness of the vaginal epithelium and vagina fluid characteristics, including pH, presence of cervical mucous, and microbiota, may influence absorption rates and bioavailability.

Because of the prevalence of endocannabinoid receptors in female reproductive organs and the central nervous system, intravaginal therapy will allow for uptake through the vaginal mucosa and deliver systemic levels of CBD to the body. Similarly, rectal applications are suitable, as rectal administration bypasses the GI tract and has faster rates of action and higher bioavailability. Furthermore, rectal administration results in higher systemic circulation of the drug, here, CBD, than oral GI administration. Specifically, rectal suppository delivery results in an increased bioavailability (51-60%) versus oral routes for CE. Data on oromucosal or sublingual delivery demonstrates that CBD has a maximum plasma concentration of 1.6 hours, but this can be delayed in some individuals. Oral CBD has a maximum plasma concentration of about 2.5-5 hours but can be delayed up to 6 hours for some individuals. Coadministration with high fat food has been shown to increase Cmax by up to 5-fold concentration. Delivery of CBD via highly vascularized nasal mucosa results in rapid uptake and a Tmax of approximately 10 minutes. The vaginal mucosa, however, has not yet been utilized for therapeutic treatments, with the exception of our treatments. Accordingly, CBD uptake through intravaginal absorption remains an opportunistic route for administration as detailed herein.

Accordingly, mucosal dosing, particularly intravaginal dosing, has a therapeutic efficacy that can allow for targeted treatment of EC cells, which will treat both localized tumors as well as metastasized tumors. This was confirmed by further testing within human patients, which showed that treatment with CE was effective in reducing chemoresistant EC, which had metastasized in the body. Full spectrum hemp extract, broad spectrum hemp extract, CBD isolate, and CBDA isolate are forms of *cannabis* extract utilized herein, as nonlimiting examples of the CE. Thus, whether through oral, oral mucosal, vaginal mucosal, or other routes of administration to treat gynecological cancers, CE was shown to be effective in complex cellular structured organoids as well as in mice models.

In certain situations, administration may be desirable within the sinus cavity, and thus delivery of CBD via highly vascularized nasal mucosa may be desirable. Studies have shown that CBD delivery via the nasal mucosa results in rapid uptake and a Tmax of approximately 10 minutes. Furthermore, as the material passes to the rear of the sinuses, it will pass through the throat and may serve as one of the best ways to reach certain metastases from the cancer, as well as the significant lymph system within the sinus and throat.

Application of CE to patients for estrogen sensitive cancer is specifically targeted at intravaginal application of the BSHE. Notably, intravaginal BSHE provided after surgery was able target remaining lesions and growths that were not completely removed by resection and to specifically to address metastatic disease by preventing the spread of metastatic cells or eliminate those which had already spread through the body. The intravaginal application is superior as it specifically targets the gynecological cancers and provides for rapid systemic uptake. This provides for direct application to the gynecological organs as well as for the systemic influence to reach both the localized cancers and metastatic cancers. Notably, compositions for oral dosing, or intravaginal dosing may comprise both the CE and the exogenous estrogen within a single composition, or the CE and the estrogen may be administered separately including through different routes of administration.

In preferred embodiments it is advantageous to modify the osmolality of the CE composition for therapeutic administration so as to be gentle for intravaginal bacteria by the addition of one or more common salts. In further preferred embodiments, it may be appropriate to modify the pH of the carrier so as to match the pH of the vagina more appropriately, which is typically acidic. A buffer, comprising the appropriate conjugate acid and base pair, can be utilized to select and maintain an appropriate pH. Preferably, oral mucosal administration or intravaginal administration of the compositions are provided at a pH of between 2 and 6.

Methods and Calculations
Patient-Derived Organoids

Patient derived organoids were created by collecting endometrial cancer tissue samples after surgery. The collected tissue was bathed, on ice, in Hank's Balanced Salt Solution (HBSS) (Hyclone, SH30031.02) with 1% Penicillin/Streptomycin (P/S) (Life Technologies, 15070-063). The tissue sample was washed three times with Dulbecco's phosphate-buffered saline (DPBS) and 1% P/S on a shaker (70 rpm) for 15 minutes each wash. Thereafter, the tissue sample was finely minced with a sterile blade while in a pre-sterilized cell-culture hood. All minced parts were enzymatically digested (Accumax™-Innovative Cell Technologies Inc., AM105-500) for about 2.5 hours at room temperature. After 2.5-hours, the whole digested tissue mince was transferred for further enzyme digestion with TrypLE™ express, (Gibco, 12604-021) for another 45 minutes in a 37° C. water bath. During this time, the solution was continuously agitated in 5 minutes intervals. Thereafter, the solution of digested tissue was passed through a 70 μm filter on a 50 mL falcon tube. The filter was removed and the flow-through with the cells was collected in 5% FBS AD+++ medium (comprising 1% ITS, 2% B27, 1% N2, 25% WRN, hegf-50 ng/mL, hfgf-10-100 ng/mL, Nicotinamide-1 mM, N-acetyl cysteine-1.25 mM, Primocin-0.2%, Estrogen-2 nm, $\Delta 8301$-0.5 uM, and Y27632). This cell suspension was centrifuged at 1000 rpm for 5 minutes at room temperature to get a cell pellet for counting. Upon checking under hemocytometer cell number was calculated and processed for organoid culture. Final cell suspensions were checked under a microscope for RBC contamination and if found, the RBCs were lysed used Red Blood Cell Lysis Buffer (Roche Diagnostics, 11814389001). The resultant endometrial cancer cells from a human patient were grown and maintained in a humidified chamber at 37° C. with 5% $CO_2$.

To culture patient-derived organoids, $2-3\times10^3$ cells were plated in a pre-warmed (37° C.) 96-well plate in 10 μL of Matrigel (5% FBS AD+++ medium) per well. Individual patient cell organoids were cultured separately in different plates. Individual patient cells were handled separately to reduce the chance of cross-contamination. After mixing cells with Matrigel, 10 μL droplets were placed in wells and put in a 37° C. incubator with 5% $CO_2$ for 30 minutes. Upon solidification of the Matrigel droplet with cells inside, the plate was placed inside a sterile hood and immersed the Matrigel droplet in 200 μL of organoid growth media. Cells were allowed to grow into mature organoids for 14 days. Treatment with individual CEs (Broad Spectrum, Full Spectrum, CBD Isolate, and CBDA), estrogen, or CE in combination with estrogen or CE in combination with chemotherapeutic agents (Paclitaxel or Carboplatin) was usually started on day 5, where the individual drug or drug combinations were added in the growth medium. All treatments were done in triplicate, including vehicle-only controls (Dimethyl sulfoxide in culture medium at the highest concentration used for drug treatments).

Some human equivalent doses were calculated using a standard formula: (M=m/MW *1/V where m=mass in grams, MW=molecular weight of the substance and V=volume of the diluent in liters). For example, if organoids are dosed with 54.35 μM CE, 0.0032 mg of CE are needed in 100 μL or 0.0001 L (V) of solute. That is equivalent to 0.00005435 M or 54.35 μM concentration, where the MW of CE=588.72 g/mol and m=0.0000032 g.

When using the 96 well plates, the following formula is used for translating the given dose to a human dosage. The surface area of a single well in a 96 well plates is 0.32 $cm^2$.

Thus, the clinical dose equivalent (mg/m$^2$) is 100 mg/m$^2$ by following the formula: Clinical Dosage (mg/m$^2$)=(PDO dosage in mg/culture plate surface area cm$^2$)×100$^2$. When comparing the two different methods of translating the organoid dose to the human dose, the two calculations show a similar human equivalent dose, for example of approximately 200 mg/day for the organoid equivalent of 10 µg/mL.

The IC50 is the 50% inhibitory concentration which is conventionally used to determine drug potency with cell-based cytotoxicity tests. To determine the IC50 for specific patient-derived organoids, individual patient organoids were treated with each of BSHE, FSHE, CBD Isolate, and CBDA as described above. Results of such treatment were used to find individual IC50s by using least squares regression (in Graphpad Prism 9) on inhibitor (i.e., a particular *cannabis* extract) vs normalized response-variable slopes. Thus, an IC50 was determined for each cannabinoid extract and selected patient-derived organoids. Thereafter, for each of the patient-derived organoids selected for testing a CE in combination with a chemotherapeutic agent or with estrogen, the organoids were treated with either the chemotherapeutic agent or estrogen alone, or the chemotherapeutic agent or estrogen in combination with a dosage of the CE equivalent to the calculated IC50 for the particular extract/organoid combination. The same IC50 dose was given with each incremental dose of chemotherapeutic agent or estrogen. Notably, the doses given for each chemotherapeutic agent in the organoids are below an equivalent of a maximal doses suitable for human administration. In this way, we could determine if a specific IC50 of a given CE and a reduced amount of chemotherapeutic agent (Paclitaxel, Carboplatin) could be used to obtain the same amount of cancer cell death as of a standard human dose of a chemotherapeutic agent.

Cell Viability Assay

To assess the cell viability in organoids after treatment, CellTiter-Glo® Luminescent Assay (Promega #G7572) was used. In brief, on day 14 of organoid culture, the Matrigel droplet in each well with organoid inside was immersed in 100 µL of fresh growth media and 100 µL of CellTiter-Glo® reagent following the manufacturer's guideline. Blank wells containing only media and CellTiter Glo® reagent (no cells) were also included in each plate. Then the plates were put on a shaker @110 rpm at room temperature for 5 minutes to induce cell lysis, followed by 25 minutes at room temperature to stabilize the luminescent signal. Each step after adding the CellTiter Glo® reagent was performed in the dark. Luminescence was measured on a FLUOstar OPTIMA plate reader (BMG Lab technologies, Offenburg, Germany). Analysis was performed by normalizing treatment values to the vehicle control and plotting them as a percentage of the vehicle control. Drug IC50 values were determined by inhibitor vs normalized response-variable slope using least squares regression in Graphpad Prism 9.

Patient-Derived Xenograft (PDX) Mouse Generation

Human patient cells from endometrial cancer were injected subcutaneously into female NOD/SCID gamma mice after resuspending in 100 µL solution. Once the tumor grew to a visible size all mice were intraperitoneally injected with single CE using the extract alone at 10-30 mg/kg body weight or the CE together with a given chemotherapeutics where the given *cannabis* extract was given at 10-30 mg/kg body weight, Paclitaxel was given at up to 20 mg/kg body weight or the vehicle thrice per week for up to 5 weeks. Tumor size was measured before treatment, followed by twice a week measurements. All treatment group mice were kept alive for up to 10 weeks after drug injection or until the tumor volume grows bigger than 2500 mm$^3$.

Tumor size was measured along with body weight at the time of tissue collection. All tumor tissues were removed carefully from the euthanized mouse body. Tumor tissue samples were kept for histology, proteomics, genomics, and other downstream processing. All downstream processing was completed following NCI Patient-Derived Models Repository SOPs.

Mouse PDX to Human Dose Conversion

The Food and Drug Administration (FDA) has suggested that the extrapolation of animal dose to human dose is correctly performed only through normalization to body surface area (BSA), which often is represented in mg/m$^2$. The human equivalent doses (HEDs) can be more appropriately calculated by using the formula: Human Equivalent Dosage in mg/kg=Mice Dosage (mg/kg)×(Mice $K_m$/Human $K_m$). The correction factor ($K_m$) is estimated by dividing the average body weight (kg) of species to its body surface area (m$^2$). For example, the average human body weight is 60 kg, and the body surface area is 1.62 m$^2$. Therefore, the $K_m$ factor for human is calculated by dividing 60 by 1.62, which is 37 and same way the mouse $K_m$ factor was calculated, which is 3. Now the interchange of unit (mg/kg to mg/m$^2$) of dose of animals or human is carried out using the $K_m$ factor as per BSA: Dosage for mg/m$^2$=$K_m$×dosage in mg/kg.

Protein Sample Preparation and TMTpro 16 plex Labelling and Processing.

Grade 1 endometrial cancer organoids from human patients (n=3) treated with BSHE, FSHE, CBDA, CBD isolate, and vehicle (control) were subjected to protein isolation. Cells were resuspended in 100 µl of ice-cold lysis buffer (0.1 M sodium carbonate, pH 11.3) supplemented with protease (Sigma) and phosphatase inhibitors (Roche). Sonication of cells were performed by using a probe tip sonication (Hielscher Ultrasound Technology). Protein lysate, which contained 150 µg of proteins, were dissolved in urea buffer (6M urea and 2M thiourea), reduced with 10 mM dithiothreitol (Sigma) at room temperature for 30 mins. Proteins were then alkylated with 20 mM iodoacetamide (Sigma) in the dark at room temperature for 30 mins. The samples were then digested with Lys-C/trypsin (1:25, enzyme: protein) for 3 hours at room temperature. The digests were diluted to less than 0.75 M by the addition of 50 mM triethylammonium bicarbonate, pH 7.8 (Sigma) and digested overnight at 37° C. Following digestion, trypsin was inactivated by acidifying the samples to a pH 2 using 1% trifluoroacetic acid (TFA; Sigma). Peptides were desalted using the solid phase extraction (SPE) columns (Oasis PRIME HLB, Waters, Australia), eluted into protein LoBind tubes with gradients 60%, 80%, 100% acetonitrile containing 0.1% TFA. Peptide concentrations were determined using Qubit 2.0 Fluorometer assay (Invitrogen, USA). Each TMTpro Label Reagent (ThermoFisher Scientific) was dissolved in 20 µl of anhydrous acetonitrile and added to the respective peptide mixture for labelling. The TMTpro 16 plex labelling of the four treatments (BSHE, FSHE, CBDA, CBD isolate) and vehicle control sample from each of the three patients were performed for 1 hour at room temperature as per manufacturer's protocol. Labelled peptides were pooled into a single tube and vacuum dried. TMTpro 16 plex labelled peptides were fractionated using the Pierce™ High pH Reversed-Phase Peptide Fractionation Kit (ThermoFisher Scientific). A total of 8 fractions were collected, vacuum dried and reconstituted in 10 µl of 2% acetonitrile and 0.1% TFA. Each fraction was subjected to liquid chromatography tandem mass spectrometry (LC-MS/MS).

Mass Spectrometry and Data Analysis

LC-MS/MS was performed using a Thermo Orbitrap Exploris 480 mass spectrometer, coupled to a Dionex Ultimate 3000 nanoLC system as described [1, 2]. The raw MS data were processed with Proteome Discoverer software package, version 2.5 (Thermo Fisher Scientific). Proteins and peptides were identified by searching against the Uniprot Human reference proteome database. The parameters were set as follows: trypsin digestion; two missed cleavages; 6 minimum peptide length; fixed modifications of cysteine (carbamidomethylation) (+57.021 Da); variable modifications of oxidation (+15.995 Da), lysine acetylation (+42.011 Da) and TMTpro of lysine (+304.207 Da). A precursor mass tolerance was set to 10 ppm and fragmentation mass tolerance was 0.02 Da. All other parameters were used as default settings. A fixed false discovery rate threshold was set to 1% for positive identifications of proteins and peptides. Analysis of the TMTpro 16 plex data was visualized in heat maps and volcano plots using Perseus 1.6.7.0 software and protein abundances were normalized by z-score transformation. For pathway analysis were further analyzed using QIAGEN's Ingenuity Pathway Analysis (IPA, QIAGEN Redwood City, CA, USA) to interpret the differentially expressed proteins in the context of predominant canonical pathways and networks.

Human patient sample cells from ovarian cancer cases were grown and maintained as organoids in a three-dimensional matrigel droplet. The effect of different CEs was then tested on patient-derived organoids.

For organoid drug treatment assays, cells were cultured for 24 hours before adding drug treatments of CEs, or their IC50 concentrations in combination estrogen. All treatments were done in triplicate, including vehicle only controls (Dimethyl sulfoxide in media at the highest concentration used for drug treatments).

For post drug treatments, organoids were cultured for another 14 days, with drug treatments and media refreshed every 3-4 days. At day 14, organoids were imaged using a Cell 3 Imager Duos 2 (Screen Holdings Cp., Ltd) which takes whole-well magnified images and is being trained to perform automated quantification of organoids.

Evaluation of cell viability was determined using a CellTiter-Glo® Luminescent Assay (Promega #G7572). Analysis was performed by normalising treatment values to the vehicle control and plotting as a percentage of the vehicle control.

To determine drug potency, dose-response curves were generated then the $IC_{50}$ value determined for each CE by nonlinear regression analysis using Graphpad Prism 9.

It will be appreciated that the embodiments and illustrations described herein are provided by way of example and that the present invention is not limited to what has been particularly disclosed. Rather, the scope of the present invention includes both combinations and sub combinations of the various features described above, as well as variations and modifications thereof that would occur to persons skilled in the art upon reading the forgoing description and that are not disclosed in the prior art. Therefore, the various compositions and methods may include one or all of the limitations of an embodiment, be performed in any order, or may combine limitations from different embodiments, as would be understood by those implementing the various methods and systems detailed herein.

What is claimed is:

1. A composition comprising a *cannabis* extract and an estrogen; wherein the *cannabis* extract comprises between 50% and 100% by weight of cannabidiol; and wherein the estrogen is provided as estrone, 17β-estradiol, estriol, estetrol, ethinylestradiol, estradiol valerate, mestranol, estropipate, or combinations thereof.

2. The composition of claim 1 further comprising between 0.025 mg and 25 mg of estrogen.

\* \* \* \* \*